United States Patent
Xu et al.

(10) Patent No.: US 11,827,645 B2
(45) Date of Patent: Nov. 28, 2023

(54) SPIRO-γ-LACTAMS, AND PREPARATION METHOD AND USE THEREOF

(71) Applicant: Chongqing University of Arts and Sciences, Chongqing (CN)

(72) Inventors: Zhigang Xu, Chongqing (CN); Zhongzhu Chen, Chongqing (CN); Dianyong Tang, Chongqing (CN)

(73) Assignee: CHONGQING UNIVERSITY OF ARTS AND SCIENCES, Chongqing (CN)

( * ) Notice: Subject to any disclaimer, the term of this patent is extended or adjusted under 35 U.S.C. 154(b) by 188 days.

(21) Appl. No.: 17/305,579

(22) Filed: Jul. 9, 2021

(65) Prior Publication Data

US 2022/0009942 A1    Jan. 13, 2022

Related U.S. Application Data

(60) Provisional application No. 63/050,823, filed on Jul. 12, 2020.

(51) Int. Cl.
*C07D 491/20* (2006.01)
*A61P 35/00* (2006.01)

(52) U.S. Cl.
CPC ............ *C07D 491/20* (2013.01); *A61P 35/00* (2018.01)

(58) Field of Classification Search
CPC ............................... C07D 491/20; A61P 35/00
See application file for complete search history.

(56) References Cited

FOREIGN PATENT DOCUMENTS

CN    113024572 A  *  6/2021  .............. A61P 35/00

OTHER PUBLICATIONS

Blatt; World Applied Sciences Journal 2013, 23, 315-325. DOI: 10.5829/idosi.wasj.2013.23.03.13064 (Year: 2013).*
Ghandi; Org. Biomol. Chem., 2015,13, 8211-8220. https://doi.org/10.1039/C5OB01095K (Year: 2015).*
Xu; Chem. Eur. J. 2018, 24, 6732-6736. https://doi.org/10.1002/chem.201801081 (Year: 2018).*
Arun et al., "Facile one-pot synthesis of novel dispirooxindole-pyrrolidine derivatives and their antimicrobial and anticancer activity against A549 human lung adenocarcinoma cancer cell line", Bioorganic & Medicinal Chemistry Letters, 2013, 23: 1839-1845.
Jin et al., "Self [3+4] Cycloadditions of Isatin N,N'-Cyclic Azomethine Imine 1,3-Dipole with N-(o-Chloromethyl)aryl Amides", J. Org. Chem., 2018, 83: 841-8416.
Lei et al., "Solvent-Dependent Chemoselective and Stereoselective Approach to Synthesis of Spiro-gamma-Lactams with Potent Anti-cancer Activity", Adv. Synth. Catal., 2021, 363: 2996-3000.
Li et al., "Ligand-controlled product selectivity in palladium-catalyzed domino post-Ugi construction of (spiro) polyheterocycles", Chem. Commun., 2016, 52(32): 5485-5646.
Li et al., "Copper-Catalyzed Trifluoromethylation of Ynones Coupled with Dearomatizing Spirocyclization of Indoles: Access to CF3-Containing Spiro[cyclopentane-1,3'-indole]", Org. Lett., 2020, 22: 3291-3296.

* cited by examiner

*Primary Examiner* — Daniel R Carcanague
(74) *Attorney, Agent, or Firm* — Vorys, Sater, Seymour and Pease LLP; Mih Suhn Koh

(57) ABSTRACT

Disclosed is a compound of Formula I or a pharmaceutically acceptable salt thereof, preparation methods thereof, pharmaceutical composition comprising the same, and use thereof in the treatment of diseases such as pancreatic cancer.

Formula I

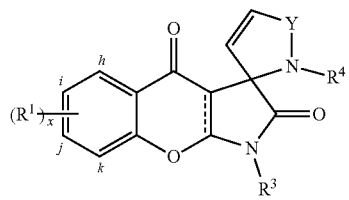

21 Claims, 1 Drawing Sheet

SPIRO-γ-LACTAMS, AND PREPARATION METHOD AND USE THEREOF

CROSS-REFERENCE TO RELATED APPLICATIONS

The present regular United States patent application claims priority to and the benefits of U.S. Provisional Application No. 63/050,823 filed on Jul. 12, 2020, the entire content of which is hereby incorporated by reference.

TECHNICAL FIELD

The present disclosure relates to Spiro-γ-Lactams, and preparation method and use thereof in the treatment of diseases, especially in the treatment of cancers.

BACKGROUND ART

Spiro-γ-lactams are privileged building blocks for construction of natural product, owing to their potent bioactivities, which widely spread a number of biologically active in natural and synthetic products. The spiro-γ-lactam ring system is a frequently encountered structural moiety in many pharmacologically relevant alkaloids, such as MI-888, coerulescine, hosfiline, elacomine, spirotryprostatin A and B, pteropodine, and didemnin analogues with spiro-quaternary carbon center, these alkaloids display potential activity against multi-drug resistant (MDR) cancer cell lines. Due to the unique three-dimensional structure and potential biological activity of spiro-γ-lactams, the development of an new efficient synthesis of this spiro structure and investigation of its bioactivities is of continued interest in the pharmaceutical field.

SUMMARY

In one aspect, the present application provides a compound of Formula I or a pharmaceutically acceptable salt thereof,

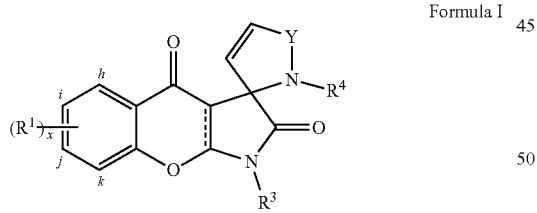

Formula I each $R^1$ is independently selected from the group consisting of H and halo, and $R^1$ is on at least one position selected from h-, i-, j- and k-positions;
x is a integer selected from 1, 2, 3 or 4;
$R^3$ is selected from the group consisting of optionally substituted alkyl and optionally substituted aryl;
===== represents a single or double bond;
Y is selected from the group consisting of C=O and C;
$R^4$ is selected from the group consisting of $R^2$ and —C(=O)—$R^2$;
with the proviso that when Y is C=O, $R^4$ is $R^2$; and when Y is C, $R^4$ is —C(=O)—$R^2$;
and with the further proviso that when ===== represents a double bond, Y is C, and $R^4$ is —C(=O)—$R^2$;

$R^2$ is selected from the group consisting of optionally substituted aryl and optionally substituted heteroaryl.

In another aspect, the present application provides a compound selected from the following structures:

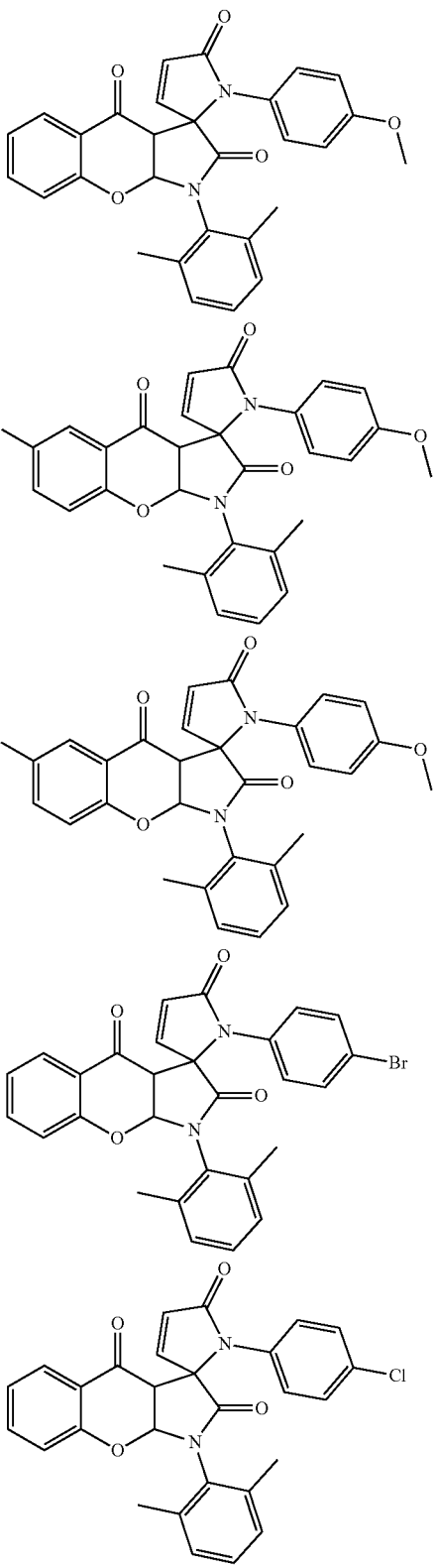

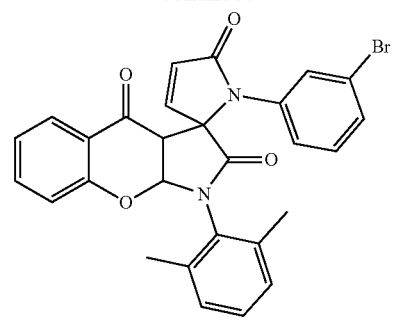
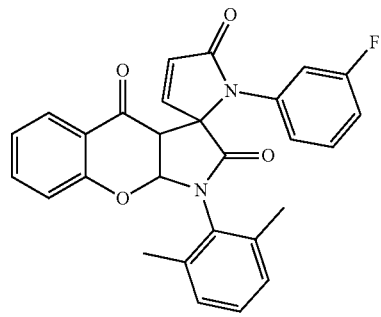
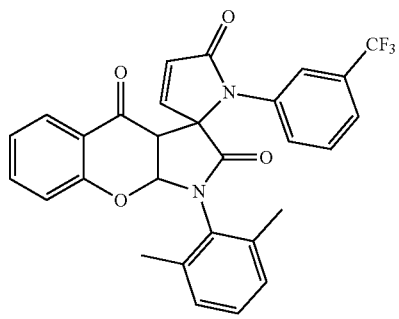
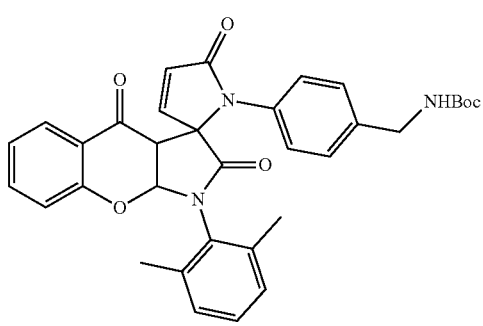
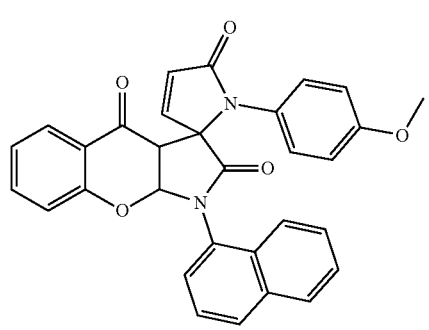
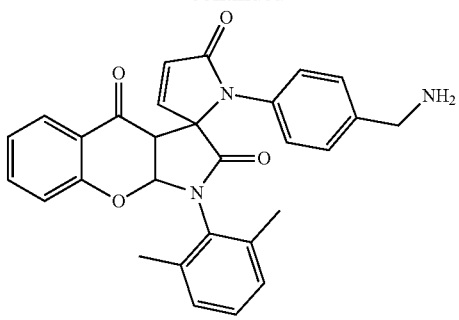
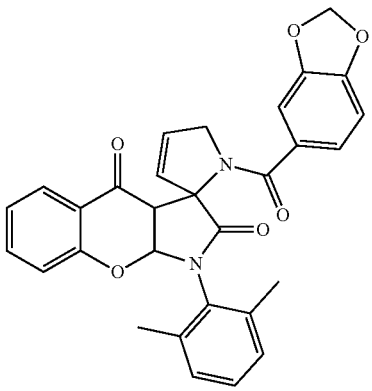
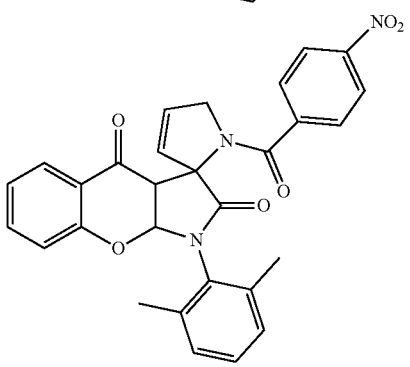
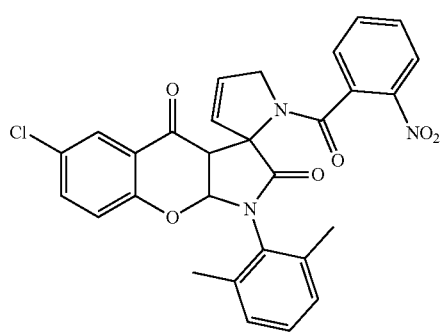
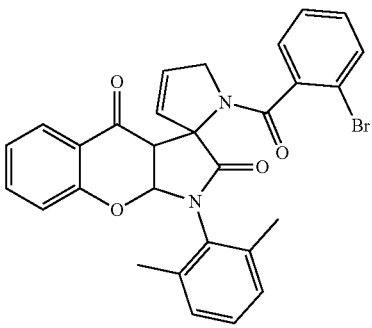

5
-continued
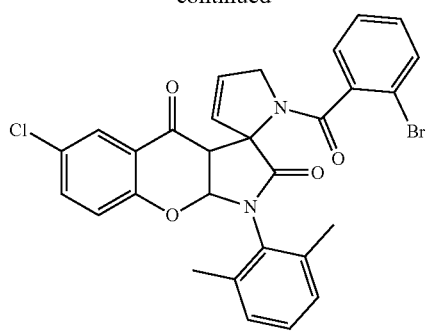
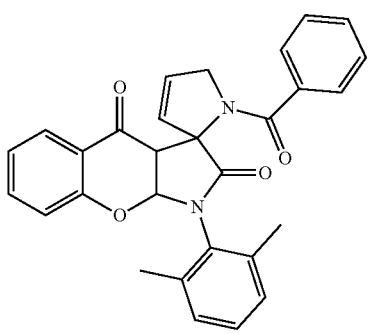
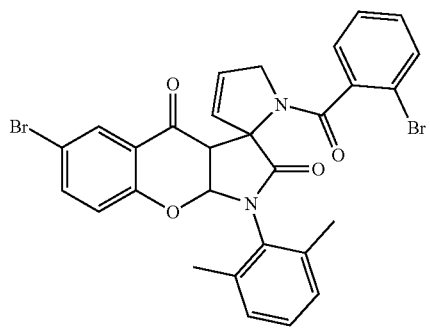
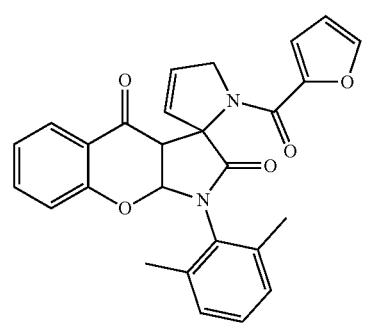
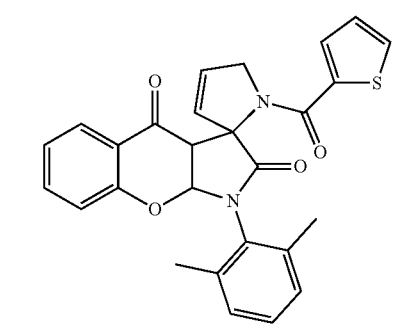
6
-continued
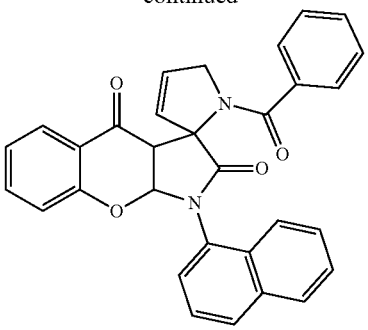
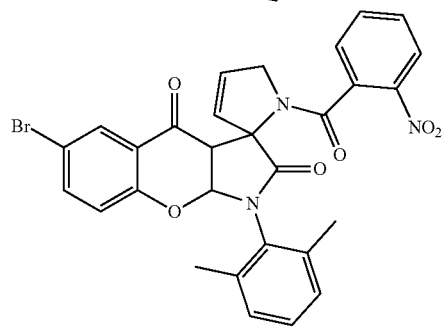
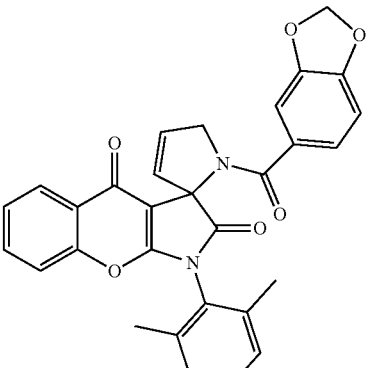
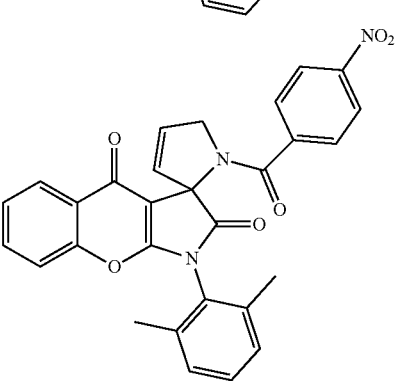
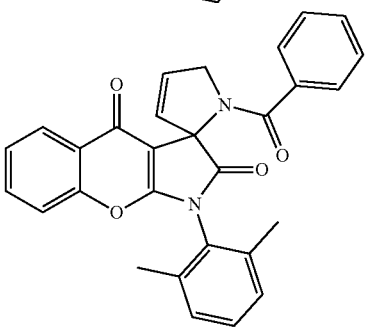

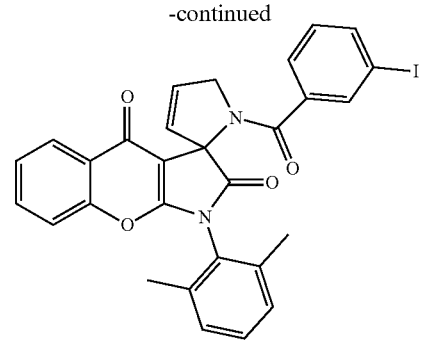
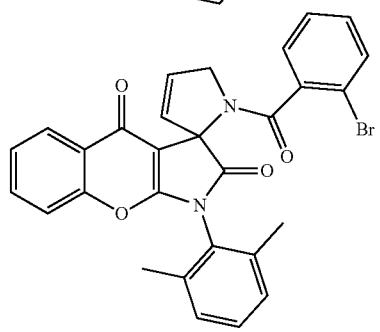
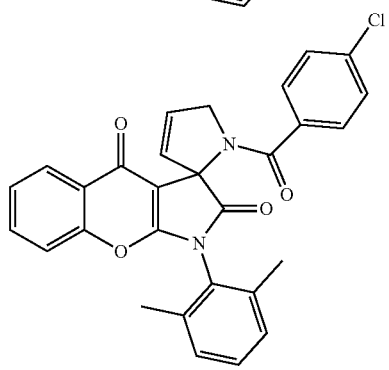
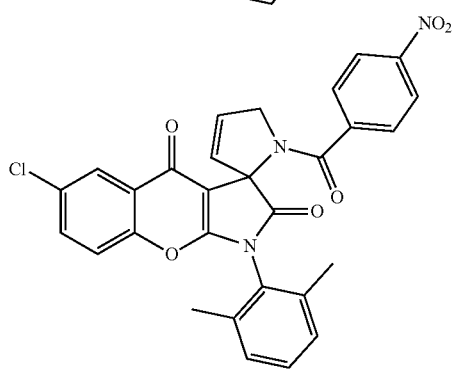
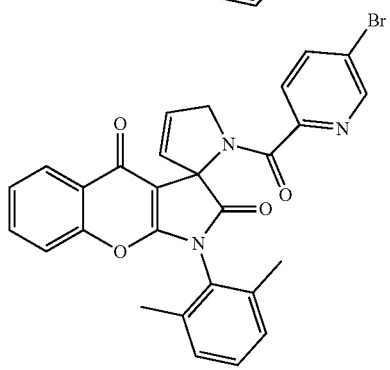
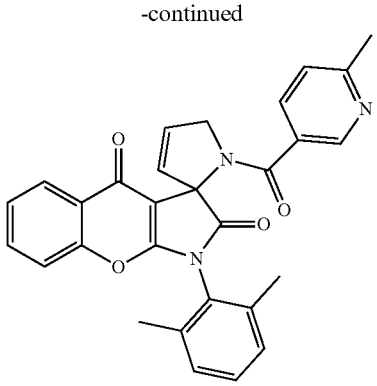
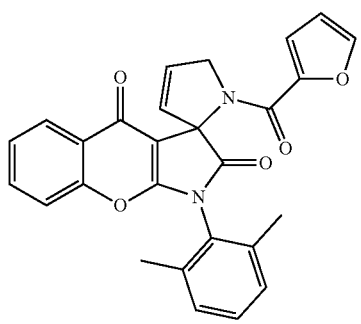
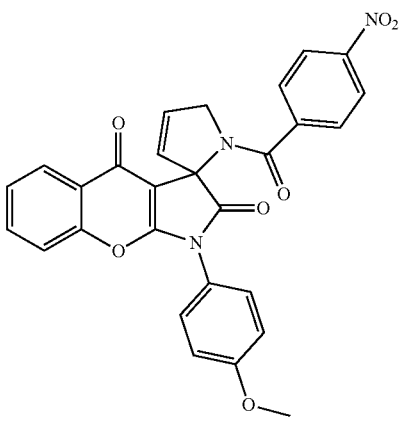
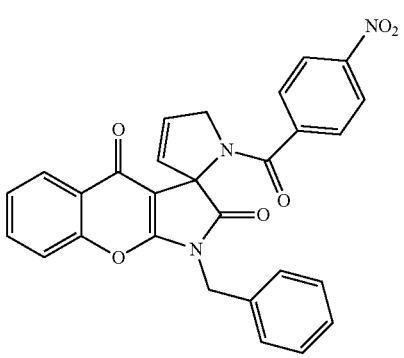

-continued

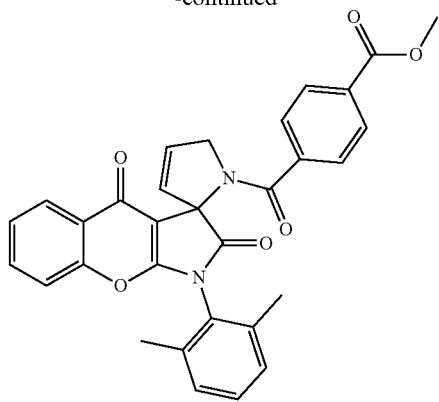

In a further aspect, the present application provides a method for preparing a compound of Formula Ia or a pharmaceutically acceptable salt thereof, comprising Step 1 and Step 2 below Step 1: performing a Ugi four-component reaction of Compounds 1, 2, 3 and 4 to obtain Compound 5;

Step 2: reacting Compound 5 to obtain the compound of Formula Ia;

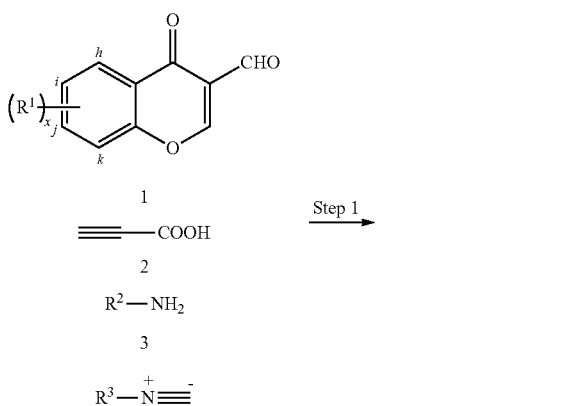

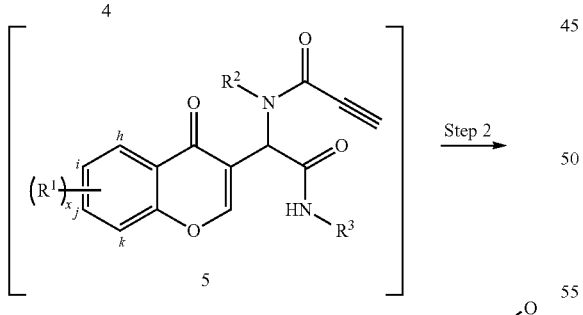

Formula Ia wherein, $R^1$, x, $R^2$, and $R^3$ are as defined in the above.

In still another aspect, the present application provides a method for preparing a compound of Formula Ib or a pharmaceutically acceptable salt thereof, comprising Step 1 and Step 2 below:

Step 1: performing a Ugi four-component reaction of Compounds 1, 4, 7 and 8 to obtain Compound 9;

Step 2: reacting Compound 9 to obtain the compound of Formula Ib;

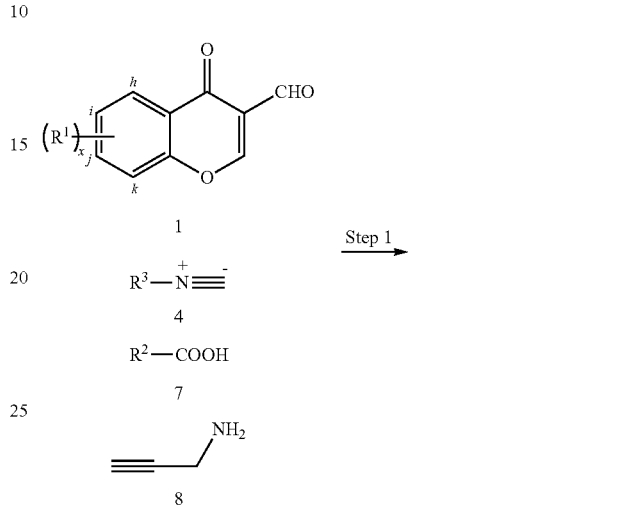

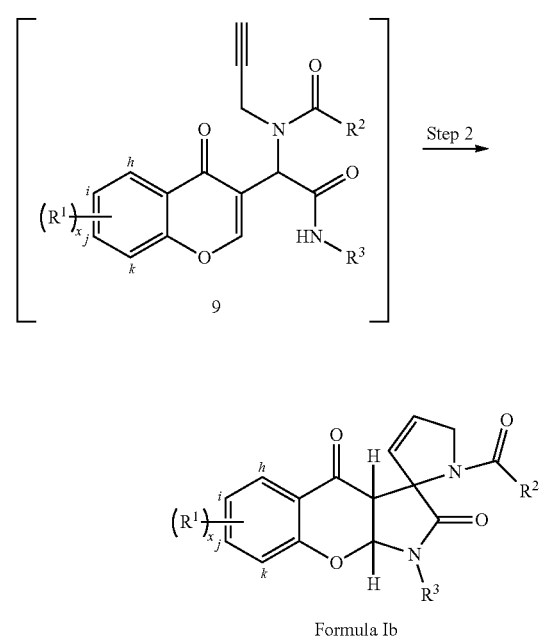

Formula Ib wherein, $R^1$, x, $R^2$, and $R^3$ are as defined in the above.

In another aspect, the present application provides a method for preparing a compound of Formula Ic or a pharmaceutically acceptable salt thereof, comprising Step 1 and Step 2 below:

Step 1: performing a Ugi four-component reaction of Compounds 1, 4, 7 and 8 to obtain Compound 9;

Step 2: reacting Compound 9 to obtain the compound of Formula Ic;

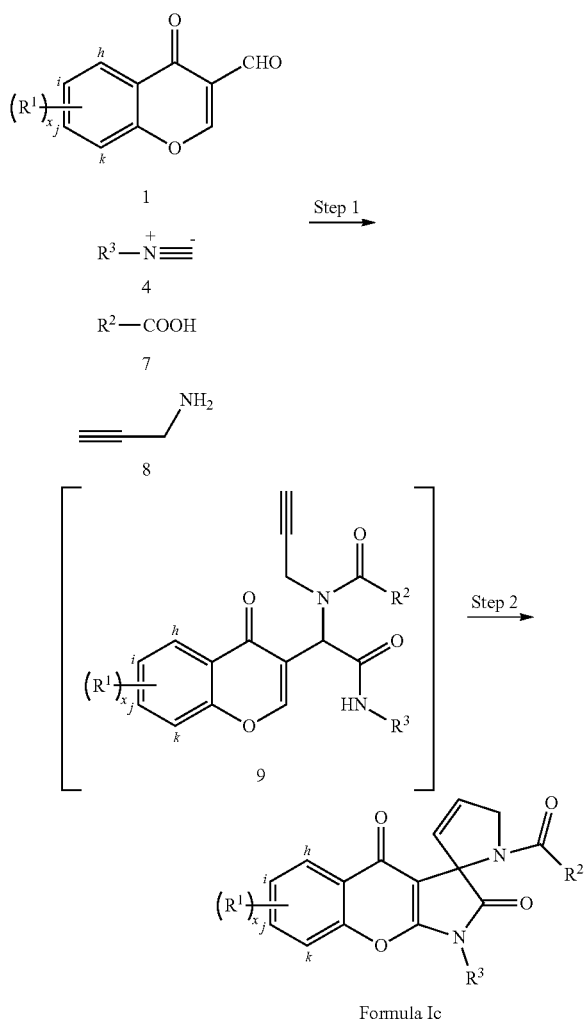

wherein, $R^1$, x, $R^2$, and $R^3$ are as defined in the above.

In still another aspect, the present application provides a pharmaceutical composition comprising the compound of formula I or a pharmaceutically acceptable salt thereof according to the present application.

In a further aspect, the present application provides a method for treating a cancer, comprising administering to a subject in need thereof a therapeutically effective amount of a compound of Formula I or a pharmaceutically acceptable salt thereof according to the present application.

BRIEF DESCRIPTION OF THE DRAWINGS

FIG. 1A shows screening and activity analysis of synthesized compounds in cancer cells PANC and U87 using MTT assay. The concentration of compound was 20 μM; FIG. 1B shows the $IC_{50}$ values of compounds 6a-6j against cancer cell line PANC and U87 measured using MTT.

DETAILED DESCRIPTION OF THE INVENTION

Definitions

Figure 1A:
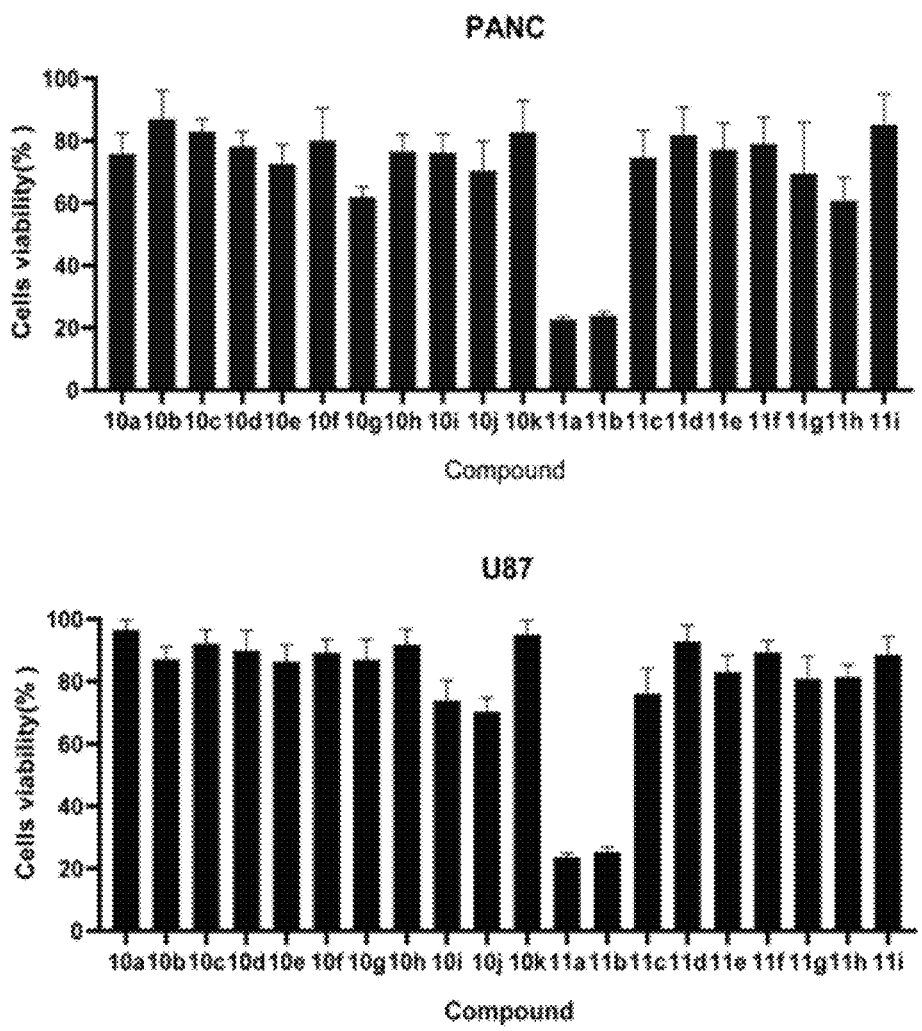
FIGS. 1A-1B.

Unless stated otherwise, the following terms used herein have the following meanings. A specific term shall not be considered unclear or indefinite when it is not specially defined. It should be understood according to its general meaning. A trade name used herein refers to a corresponding product or an active ingredient thereof.

The term "substituted" means that one or more hydrogen atoms on a given atom are replaced with a substituent, provided that the given atom has a normal valence state and the compound after substitution is stable. When the substituent is an oxo (i.e., =O), which means that two hydrogen atoms are replaced, the oxo substitution will not occur on an aromatic group.

The term "optional" or "optionally" means that the subsequently described event or circumstance may or may not occur, and that the description includes instances where said event or circumstance occurs and instances where said event or circumstance does not occurs. For example, ethyl group is "optionally" substituted with one or more fluorine or chlorine atoms, which means that ethyl group may be unsubstituted ($CH_2CH_3$), mono-substituted (such as $CH_2CH_2F$, $CHClCH_3$), multiple-substituted (such as $CHFCH_2F$, $CHClCHF_2$, $CH_2CHF_2$, and so on) or fully substituted ($CCl_2CF_3$, $CF_2CF_3$). A person skilled in the art will understand that in respect to any group containing one or more substituents, any substitution or substitution mode that is spatially impossible and/or not synthesizable will not be introduced.

The term "optionally substituted" as used herein means that a group can be optionally substituted by one or more substituents independently selected from the group consisting of alkyl, alkenyl, halo, haloalkyl, haloalkenyl, alkoxy, alkylthio, cyano, nitro, hydroxy, mercapto, —C(=S)OH, —C(=S)O-alkyl, —C(=S)—H, —C(=S)-alkyl, aryl, aryloxy, aralkyl, cycloalkyl, cycloalkyloxy, cycloalkylalkyl, cycloalkenyl, cycloalkenyloxy, cycloalkenylalkyl, heterocycloalkyl, heterocycloalkyloxy, heterocycloalkylalkyl, heteroaryl, heteroaryloxy, heteroarylalkyl, hydroxyamino, alkoxyamino, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t R^{16}$) (wherein t is 1 or 2), —S(O)$_t$O$R^{16}$ (wherein t is 1 or 2), —S(O)$_t R^{16}$ (wherein t is 0, 1, or 2) and —S(O)$_t$N($R^{14}$)$_2$ (wherein t is 1 or 2), wherein in each $R^{14}$ and each $R^{16}$ are independently hydrogen, alkyl, cycloalkyl, cycloalkenyl, aryl, arylalkyl, heterocycloalkyl, heterocycloalkylalkyl, heteroaryl, or heteroarylalkyl. For example, the substituents may be independently selected from the group consisting of alkyl, halo and hydroxy.

The expression $C_{m-n}$ as used herein means that this moiety has an integer number of carbon atoms within a given range. For example, "$C_{1-6}$" means that this group may have 1 carbon atom, 2 carbon atoms, 3 carbon atoms, 4 carbon atoms, 5 carbon atoms or 6 carbon atoms.

When any variant (such as, R) occurs more than one times at the composition or structure of a compound, it is defined independently in each case. Therefore, for example, if a group is substituted with two Rs, then each R has an independent option.

The term "halogen" or "halo" refers to fluoro, chloro, bromo and iodo.

The term "hydroxy" refers to —OH group.

The term "cyano" refers to —CN group.

The term "amino" refers to —$NH_2$ group.

The term "nitro" refers to —$NO_2$ group.

The term "alkyl" refers to a hydrocarbyl group of Formula $C_nH_{2n+1}$. The alkyl group can be straight or branched. For example, the term "$C_{1-6}$ alkyl" refers to an alkyl group having 1 to 6 carbon atoms, such as 1 carbon atom, 2 carbon atoms, 3 carbon atoms, 4 carbon atoms, 5 carbon atoms and 6 carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moiety (i.e., alkyl) in an alkoxy group, a monoalkylamino group, a dialkylamino group, an alkylsulfonyl group, an alkoxycarbonyl group, and an alkylthio group has the same definition as defined above.

The term "alkenyl" refers to a linear or branched unsaturated aliphatic hydrocarbyl group consisting of carbon and hydrogen atoms, which has at least one carbon carbon double bond.

The term "alkoxy" refers to —O-alkyl.

The term "cycloalkyl" refers to an all-carbon ring that is fully saturated and can exist in the form of a monocyclic ring, bicyclic ring, tricyclic ring, or polycyclic ring, fused ring, bridged ring or spirocyclic ring. Unless otherwise indicated, the carbocycle is typically a 3- to 10-membered ring, such as 3-membered ring, 4-membered ring, 5-membered ring, 6-membered ring, 7-membered ring, 8-membered ring, 9-membered ring, and 10-membered ring. Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl etc.

The term "heterocycloalkyl" refers to a fully saturated or partially unsaturated (but not fully unsaturated heteroaromatic) non-aromatic ring that can be exist in the form of a monocyclic ring, bicyclic ring, tricyclic ring, or polycyclic ring, fused ring, bridged ring or spirocyclic ring. Unless otherwise indicated, the heterocyclyl is typically a 3- to 10-membered ring (such as 3-membered ring, 4-membered ring, 5-membered ring, 6-membered ring, 7-membered ring, 8-membered ring, 9-membered ring, and 10-membered ring) containing 1 to 4 heteroatoms (such as 1, 2, 3 or 4 heteroatoms) independently selected from sulfur, oxygen, and/or nitrogen. Non-limiting examples of heterocycloalkyl include, but are not limited to oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl, etc.

The term "aryl" refers to a group of an all-carbon monocyclic or fused polycyclic aromatic ring having a conjugated π-electron system. For example, an aryl may have 6 to 20, 6 to 14, or 6 to 12 carbon atoms. Aryl may have at least one aromatic ring, and non-limiting examples thereof include, but are not limited to, phenyl, naphthyl, anthryl and 1,2,3,4-tetrahydronaphthalene, etc.

The term "heteroaryl" refers to a monocyclic or fused polycyclic system containing at least one ring atom (such as 1, 2, 3, 4 or 5 ring atoms) selected from N, O, and S with remaining ring atoms being C, and having at least one aromatic ring. Preferred heteroaryl has a single 4- to 8-membered ring (such as 4-membered ring, 5-membered ring, 6-membered ring, 7-membered ring, or 8-membered ring), especially single 5- to 8-membered ring, or has a fused polycyclic ring containing 6 to 14 (such as 6-membered ring, 7-membered ring, 8-membered ring, 9-membered ring, 10-membered ring, 11-membered ring, 12-membered ring, 13-membered ring, and 14-membered ring), especially 6 to 10 rings atoms. Non-limiting examples of heteroaryl include, but are not limited to, pyrrolyl, furyl, thienyl, thiazolyl imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, etc.

The term "treatment" or "treating" refers to the administration of the compounds or preparations of the present application for ameliorating or eliminating diseases or one or more symptoms associated with the diseases, comprising:
  (i) inhibition of diseases or conditions, i.e. restraining their development; or
  (ii) relief of diseases or conditions, i.e. recovering from the diseases or conditions.

The term "therapeutically effective amount" means an amount of a compound of the present application that (i) treats or prevents a particular disease, condition, or disorder, (ii) attenuates, ameliorates, or eliminates one or more symptoms of a particular disease, condition, or disorder, or (iii) prevents or retards the onset of one or more symptoms of a particular disease, condition, or disorder as described herein. The amount of the compounds of the present application constituting so-called "therapeutically effective amount" depends on the compound, disease condition and severity thereof, the way of administration and age of the mammal to be treated, but can be routinely determined by those skilled in the art on the basis of their knowledge and the disclosure herein.

The term "pharmaceutical composition" refers to a formulation, which comprises one or more compounds of the present application, or the salts thereof, along with the carriers, excipients and/or media generally accepted in the field for delivering the biologically active compounds to the organisms (such as humans). The purpose of pharmaceutical composition is to facilitate the administration of the compound of the present application to the organisms.

The term "pharmaceutically acceptable" refers to a compound, material, composition and/or dosage form that is applicable to the contact with human and animal tissues without an excessive toxicity, irritation, allergic reaction or other problems or complications in the scope of reliable medical judgment, and is commensurate with an acceptable benefits/risk ratio.

The term "pharmaceutically acceptable salt" includes, but is not limited to, an acid addition salt formed from the compound of Formula I and an inorganic acid, an acid addition salt formed from the compound of Formula I and an organic acid, or an addition salt formed from the compound of Formula I and an acidic amino acid, etc. The term "pharmaceutical composition" refers to a mixture of one or more compounds of the present application or pharmaceutically acceptable salts thereof and a pharmaceutically acceptable excipient. The purpose of pharmaceutical composition is to facilitate the administration of the compounds of the present application to the organism.

The term "pharmaceutically acceptable carrier" refers to those carriers which have no significant irritation and do not impair the bioactivity and property of the active compound. The "pharmaceutically acceptable carrier" refers to inert substance which is administered with active ingredient and is beneficial to the administration thereof, and comprises but not limited to any of the following substances approved by State Food and Drug Administration for use in human or animal (e.g. livestock): glidant, sweetening agent, diluent, preservative, dye/colorant, flavoring agent, surfactant, wetting agent, dispersant, disintegrant, suspending agent, stabilizing agent, isotonic agent, solvent or emulsifying agent. Non-limiting examples of the carriers comprise calcium carbonate, calcium phosphate, various sugars and starches, cellulose derivative, gelatine, vegetable oil and polyethylene glycol or the like. Other information regarding the carriers may be found in Remington: The Science and Practice of Pharmacy, 21st Ed., Lippincott, Williams & Wilkins (2005), of which the contents are incorporated herein by reference.

The term "excipient" generally refers to the carrier, diluent and/or medium used to formulate effective pharmaceutical composition.

The pharmaceutical composition of the present application can be prepared through combining the compounds of the present application and suitable pharmaceutical acceptable carriers or excipients. For example, it can be prepared as solid, semi-solid, liquid or gaseous formulations, such as tablets, pills, capsules, powder, granules, ointments, emulsions, suspensions, solutions, suppositories, injections, inhalants, gels, microspheres and aerosol, etc.

The typical routes for the administration of the compounds of the present application or the pharmaceutically acceptable salts thereof or the pharmaceutical composition thereof include, but are not limited to oral, rectal, transmucosal, enteral administration, or topical, percutaneous, inhalational, parenteral, sublingual, intravaginal, intranasal, intraocular, intraperitoneal, intramuscular, subcutaneous, intravenous administration. The preferred administration route is oral administration.

The pharmaceutical composition of the present application can be manufactured through the well-known methods in the art, such as the mix, dissolving, granulation, sugar coating, grinding, emulsification, freeze-drying, etc.

In an embodiment, the pharmaceutical composition is in the form for oral use. For oral administration, the active compounds can be mixed with the pharmaceutically acceptable carriers known in the art, to prepare the pharmaceutical composition. With these carriers, the compounds of the present application can be formulated into tablets, pills, lozenges, sugar-coated tablets, capsules, liquid, gels, syrup, suspensions and the like, for oral administration to the patients.

The solid oral use composition can be prepared through conventional mixing, filling or compressing methods. For example, it can be obtained through the following method: the active compounds are mixed with the solid excipients; optionally the resulting mixture is ground, and other suitable adjuvants are added if necessary; then the mixture is processed into granules, so that the core of the tablets or sugar-coated tablets is obtained. Suitable adjuvants include, but are not limited to, adhesives, diluents, disintegrants, lubricants, glidants, sweeteners or flavoring agents, etc., such as microcrystalline cellulose, glucose solution, mucilage of gum arabic, gelatin solution, sucrose and starch paste; talc, starch, magnesium stearate, calcium stearate or stearic acid; lactose, sucrose, starch, mannitol, sorbitol or dicalcium phosphate; silica; crosslinked sodium carboxymethylcellulose, pre-gelatinized starch, sodium starch glycolate, alginic acid, corn starch, potato starch, methyl cellulose, agar, carboxymethyl cellulose, crosslinked polyvinylpyrrolidone, etc. Optionally, the core of the tablet can be coated through the well-known methods in general pharmaceutical practice, and enteric coating is particularly used.

The pharmaceutical composition is also suitable for parenteral administration, such as sterile solutions, suspensions or freeze-dried products in adequate unit dose form. The suitable excipients, such as fillers, buffers or surfactants, can also be used.

In all the methods for applying the compound of Formula I according to the disclosure, the daily administered dosage is, for example, 0.01-200 mg/kg body weight.

The phrase "comprise" and English variations thereof, such as "comprises" and "comprising", should be construed in an open and inclusive sense, that is as, "including, but not limited to".

In one aspect, the present application provides a compound of Formula I or a pharmaceutically acceptable salt thereof,

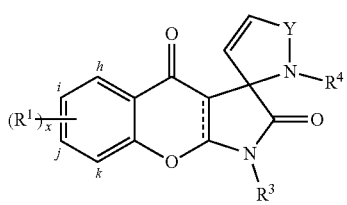

Formula I each $R^1$ is independently selected from the group consisting of H and halo, and $R^1$ is on at least one position selected from h-, i-, j- and k-positions;

x is a integer selected from 1, 2, 3 or 4;

$R^3$ is selected from the group consisting of optionally substituted alkyl and optionally substituted aryl;

===== represents a single or double bond;

Y is selected from the group consisting of C=O and C;

$R^4$ is selected from the group consisting of $R^2$ and —C(=O)—$R^2$;

with the proviso that when Y is C=O, $R^4$ is $R^2$; and when Y is C, $R^4$ is —C(=O)—$R^2$;

and with the further proviso that when ===== represents a double bond, Y is C, and $R^4$ is —C(=O)—$R^2$;

$R^2$ is selected from the group consisting of optionally substituted aryl and optionally substituted heteroaryl.

In some embodiments, wherein $R^1$ is on at least one position selected from i- and j-positions.

In some embodiments, each $R^1$ is independently selected from the group consisting of H, Cl and Br.

In some embodiments, wherein $R^3$ is selected from the group consisting of alkyl and aryl, each of which is independently optionally substituted with one or more substituents selected from alkyl, alkoxy, and aryl.

In some embodiments, $R^3$ is selected from the group consisting of $C_{1-6}$ alkyl and $C_{6-20}$ aryl, each of which is independently optionally substituted with one or more substituents selected from $C_{1-6}$ alkyl, $C_{1-6}$ alkoxy, and $C_{6-20}$ aryl.

In some embodiments, $R^3$ is selected from the group consisting of $C_{1-6}$ alkyl and $C_{6-15}$ aryl, each of which is independently optionally substituted with one or more substituents selected from $C_{1-6}$ alkyl, $C_{1-6}$ alkoxy, and $C_{6-15}$ aryl.

In some embodiments, $R^3$ is selected from the group consisting of $C_{1-6}$ alkyl and $C_{6-12}$ aryl, each of which is independently optionally substituted with one or more substituents selected from $C_{1-6}$ alkyl, $C_{1-6}$ alkoxy, and $C_{6-12}$ aryl.

In some embodiments, $R^3$ is selected from the group consisting of: alkyl optionally substituted with aryl; and aryl optionally substituted with one or more substituents selected from alkyl and alkoxy.

In some embodiments, said aryl in the definition of $R^3$ is selected from the group consisting of phenyl and naphthyl.

In some embodiments, $R^3$ is selected from the group consisting of benzyl, 2,6-dimethylphenyl, 4-methoxyphenyl and naphthyl.

In some embodiments, $R^2$ is selected from the group consisting of aryl and heteroaryl, each of which is independently optionally substituted with one or more substituents selected from: halo; alkoxy; nitro; alkoxycarbonyl; and alkyl optionally substituted with one or more substituents selected from halo and NR'R", wherein R' and R" are each independently selected from the group consisting of H and Boc.

In some embodiments, $R^2$ is selected from the group consisting of $C_{6-20}$ aryl and 5- to 20-membered heteroaryl, each of which is independently optionally substituted with one or more substituents selected from: halo; $C_{1-6}$ alkoxy; nitro; $C_{1-6}$ alkoxycarbonyl; and $C_{1-6}$ alkyl optionally substituted with one or more substituents selected from halo and NR'R", wherein R' and R" are each independently selected from the group consisting of H and Boc.

In some embodiments, $R^2$ is selected from the group consisting of $C_{6-15}$ aryl and 5- to 15-membered heteroaryl, each of which is independently optionally substituted with one or more substituents selected from: halo; $C_{1-6}$ alkoxy; nitro; $C_{1-6}$ alkoxycarbonyl; and $C_{1-6}$ alkyl optionally substituted with one or more substituents selected from halo and NR'R", wherein R' and R" are each independently selected from the group consisting of H and Boc.

In some embodiments, $R^2$ is selected from the group consisting of $C_{6-12}$ aryl and 5- to 12-membered heteroaryl, each of which is independently optionally substituted with one or more substituents selected from: halo; $C_{1-6}$ alkoxy; nitro; $C_{1-6}$ alkoxycarbonyl; and $C_{1-6}$ alkyl optionally substituted with one or more substituents selected from halo and NR'R", wherein R' and R" are each independently selected from the group consisting of H and Boc.

In some embodiments, said aryl in the definition of $R^2$ is selected from the group consisting of phenyl and 1,3-benzodioxolyl.

In some embodiments, said heteroaryl in the definition of $R^2$ is selected from the group consisting of furyl, thienyl and pyridyl.

In some embodiments, $R^2$ is selected from the group consisting of 1,3-benzodioxolyl; furyl; thienyl; pyridyl optionally substituted with halo or $C_{1-4}$ alkyl; and phenyl optionally substituted with one or more substituents selected from the group consisting of halo, $C_{1-6}$ alkoxy, nitro, $C_{1-6}$ alkoxycarbonyl, and $C_{1-6}$ alkyl optionally substituted with one or more substituents selected from halo and NR'R", wherein R' and R" are each independently selected from the group consisting of H and Boc.

In some embodiments, $R^2$ is selected from the group consisting of 1,3-benzodioxolyl; furyl; thienyl; pyridyl optionally substituted with Br or methyl; and phenyl optionally substituted with F, Cl, Br, I, methoxy, nitro, methoxycarbonyl, $CF_3$, —$CH_2NH_2$ or —$CH_2NHBoc$.

In some embodiments, said Formula I is Formula Ia, Ib, or Ic,

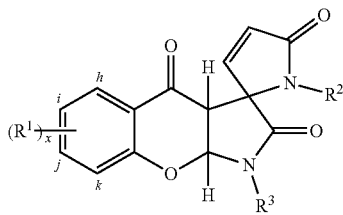

Formula Ia

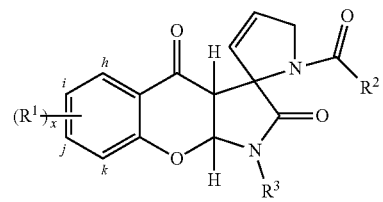

Formula Ib

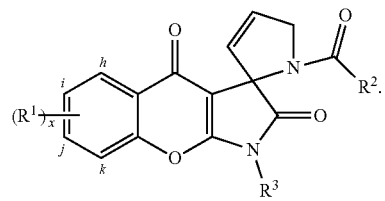

Formula Ic

In some embodiments, in said Formula Ia, $R^3$ is optionally substituted aryl.

In some embodiments, in said Formula Ia, $R^3$ is aryl optionally substituted with one or more substituents selected from alkyl.

In some embodiments, in said Formula Ia, $R^3$ is $C_{6-20}$ aryl optionally substituted with one or more substituents selected from $C_{1-6}$ alkyl.

In some embodiments, in said Formula Ia, $R^3$ is $C_{6-15}$ aryl optionally substituted with one or more substituents selected from $C_{1-6}$ alkyl.

In some embodiments, in said Formula Ia, $R^3$ is $C_{6-12}$ aryl optionally substituted with one or more substituents selected from $C_{1-6}$ alkyl.

In some embodiments, in said Formula Ia, $R^3$ is selected from the group consisting of phenyl and naphthyl, each of which is optionally substituted with one or more substituents selected from $C_{1-4}$ alkyl.

In some embodiments, in said Formula Ia, $R^3$ is selected from the group consisting of phenyl and naphthyl, each of which is optionally substituted with one or more methyl groups.

In some embodiments, in said Formula Ia, $R^3$ is selected from the group consisting of 2,6-dimethylphenyl and naphthyl.

In some embodiments, in said Formula Ia, $R^2$ is optionally substituted aryl.

In some embodiments, in said Formula Ia, $R^2$ is aryl optionally substituted with one or more substituents selected from: halo; alkoxy; and alkyl optionally substituted with one or more substituents selected from halo and NR'R", wherein R' and R" are each independently selected from the group consisting of H and Boc.

In some embodiments, in said Formula Ia, $R^2$ is $C_{6-20}$ aryl optionally substituted with one or more substituents selected from: halo; $C_{1-6}$ alkoxy; and $C_{1-6}$ alkyl optionally substituted with one or more substituents selected from halo and NR'R", wherein R' and R" are each independently selected from the group consisting of H and Boc.

In some embodiments, in said Formula Ia, $R^2$ is $C_{6-15}$ aryl optionally substituted with one or more substituents selected from: halo; $C_{1-6}$ alkoxy; and $C_{1-6}$ alkyl optionally substituted with one or more substituents selected from halo and NR'R", wherein R' and R" are each independently selected from the group consisting of H and Boc.

In some embodiments, in said Formula Ia, $R^2$ is $C_{6-12}$ aryl optionally substituted with one or more substituents selected from: halo; $C_{1-6}$ alkoxy; and $C_{1-6}$ alkyl optionally substituted with one or more substituents selected from halo and NR'R", wherein R' and R" are each independently selected from the group consisting of H and Boc.

In some embodiments, in said Formula Ia, $R^2$ is phenyl optionally substituted with one or more substituents selected from: F; Cl; Br; $C_{1-4}$ alkoxy; and $C_{1-4}$ alkyl optionally substituted with one or more substituents selected from F and NR'R", wherein R' and R" are each independently selected from the group consisting of H and Boc.

In some embodiments, in said Formula Ia, $R^2$ is phenyl optionally substituted with one or more substituents selected from the group consisting of F, Cl, Br, methoxy, —$CF_3$, —$CH_2NH_2$ or —$CH_2NHBoc$.

In some embodiments, in said Formula Ib, $R^3$ is optionally substituted aryl.

In some embodiments, in said Formula Ib, $R^3$ is aryl optionally substituted with one or more substituents selected from alkyl.

In some embodiments, in said Formula Ib, $R^3$ is $C_{6-20}$ aryl optionally substituted with one or more substituents selected from $C_{1-6}$ alkyl.

In some embodiments, in said Formula Ib, $R^3$ is $C_{6-15}$ aryl optionally substituted with one or more substituents selected from $C_{1-6}$ alkyl.

In some embodiments, in said Formula Ib, $R^3$ is $C_{6-12}$ aryl optionally substituted with one or more substituents selected from $C_{1-6}$ alkyl.

In some embodiments, in said Formula Ib, $R^3$ is selected from the group consisting of phenyl and naphthyl, each of which is optionally substituted with one or more substituents selected from $C_{1-4}$ alkyl.

In some embodiments, in said Formula Ib, $R^3$ is selected from the group consisting of phenyl and naphthyl, each of which is optionally substituted with one or more methyl groups.

In some embodiments, in said Formula Ib, $R^3$ is selected from the group consisting of 2,6-dimethylphenyl and naphthyl.

In some embodiments, in said Formula Ib, $R^2$ is selected from the group consisting of aryl and heteroaryl, each of which is independently optionally substituted with one or more substituents selected from the group consisting of halo and nitro.

In some embodiments, in said Formula Ib, $R^2$ is selected from the group consisting of $C_{6-20}$ aryl and 5- to 20-membered heteroaryl, each of which is independently optionally substituted with one or more substituents selected from the group consisting of halo and nitro.

In some embodiments, in said Formula Ib, $R^2$ is selected from the group consisting of $C_{6-15}$ aryl and 5- to 15-membered heteroaryl, each of which is independently optionally substituted with one or more substituents selected from the group consisting of halo and nitro; In some embodiments, in said Formula Ib, $R^2$ is selected from the group consisting of $C_{6-12}$ aryl and 5- to 12-membered heteroaryl, each of which is independently optionally substituted with one or more substituents selected from the group consisting of halo and nitro.

In some embodiments, in said Formula Ib, said aryl in the definition of $R^2$ is selected from the group consisting of phenyl and 1,3-benzodioxolyl.

In some embodiments, in said Formula Ib, said heteroaryl in the definition of $R^2$ is selected from the group consisting of furyl, thienyl and pyridyl.

In some embodiments, in said Formula Ib, $R^2$ is selected from the group consisting of 1,3-benzodioxolyl; furyl; thienyl; and phenyl optionally substituted with one or more substituents selected from the group consisting of halo and nitro.

In some embodiments, in said Formula Ib, $R^2$ is selected from the group consisting of 1,3-benzodioxolyl, furyl, thienyl, 4-nitrophenyl, 2-nitrophenyl, and 2-bromophenyl.

In some embodiments, in said Formula Ic, $R^3$ is selected from the group consisting of alkyl and aryl, each of which is independently optionally substituted with one or more substituents selected from alkyl, alkoxy, and aryl.

In some embodiments, in said Formula Ic, $R^3$ is selected from the group consisting of $C_{1-6}$ alkyl and $C_{6-20}$ aryl, each of which is independently optionally substituted with one or more substituents selected from $C_{1-6}$ alkyl, $C_{1-6}$ alkoxy, and $C_{6-20}$ aryl.

In some embodiments, in said Formula Ic, $R^3$ is selected from the group consisting of $C_{1-6}$ alkyl and $C_{6-15}$ aryl, each of which is independently optionally substituted with one or more substituents selected from $C_{1-6}$ alkyl, $C_{1-6}$ alkoxy, and $C_{6-15}$ aryl.

In some embodiments, in said Formula Ic, $R^3$ is selected from the group consisting of $C_{1-6}$ alkyl and $C_{6-12}$ aryl, each of which is independently optionally substituted with one or more substituents selected from $C_{1-6}$ alkyl, $C_{1-6}$ alkoxy, and $C_{6-12}$ aryl.

In some embodiments, in said Formula Ic, $R^3$ is selected from the group consisting of: alkyl optionally substituted with aryl; and aryl optionally substituted with one or more substituents selected from alkyl and alkoxy.

In some embodiments, in said Formula Ic, $R^3$ is selected from the group consisting of: $C_{1-4}$ alkyl optionally substituted with $C_{6-12}$ aryl; and $C_{6-12}$ aryl optionally substituted with one or more substituents selected from $C_{1-4}$ alkyl and $C_{1-4}$ alkoxy.

In some embodiments, in said Formula Ic, said aryl in the definition of $R^3$ is selected from the group consisting of phenyl and naphthyl.

In some embodiments, in said Formula Ic, said aryl in the definition of $R^3$ is phenyl; In some embodiments, in said Formula Ic, $R^3$ is selected from the group consisting of benzyl, 2,6-dimethylphenyl, and 4-methoxyphenyl.

In some embodiments, in said Formula Ic, $R^2$ is selected from the group consisting of aryl and heteroaryl, each of which is independently optionally substituted with one or more substituents selected from the group consisting of halo, nitro, alkoxycarbonyl, and alkyl.

In some embodiments, in said Formula Ic, $R^2$ is selected from the group consisting of $C_{6-20}$ aryl and 5- to 20-membered heteroaryl, each of which is independently optionally substituted with one or more substituents selected from the group consisting of halo, nitro, $C_{1-6}$ alkoxycarbonyl, and $C_{1-6}$ alkyl.

In some embodiments, in said Formula Ic, $R^2$ is selected from the group consisting of $C_{6-15}$ aryl and 5- to 15-membered heteroaryl, each of which is independently optionally substituted with one or more substituents selected from the group consisting of halo, nitro, $C_{1-6}$ alkoxycarbonyl, and $C_{1-6}$ alkyl.

In some embodiments, in said Formula Ic, $R^2$ is selected from the group consisting of $C_{6-12}$ aryl and 5- to 12-membered heteroaryl, each of which is independently optionally substituted with one or more substituents selected from the group consisting of halo, nitro, $C_{1-6}$ alkoxycarbonyl, and $C_{1-6}$ alkyl.

In some embodiments, in said Formula Ic, said aryl in the definition of $R^2$ is selected from the group consisting of phenyl and 1,3-benzodioxolyl.

In some embodiments, in said Formula Ic, said heteroaryl in the definition of R² is selected from the group consisting of furyl, thienyl and pyridyl.

In some embodiments, in said Formula Ic, R² is selected from the group consisting of 1,3-benzodioxolyl; furyl; pyridyl optionally substituted with halo or C$_{1-4}$ alkyl; and phenyl optionally substituted with one or more substituents selected from the group consisting of halo, nitro, and C$_{1-4}$ alkoxycarbonyl.

In some embodiments, in said Formula Ic, R² is selected from the group consisting of 1,3-benzodioxolyl, furyl, 4-bromopyridyl, 4-methylpyridyl, 4-nitrophenyl, 4-chlorophenyl, 2-bromophenyl, 3-iodophenyl, 4-methoxylcarbonylphenyl.

In another aspect, the present application provides a compound selected from the following structures:

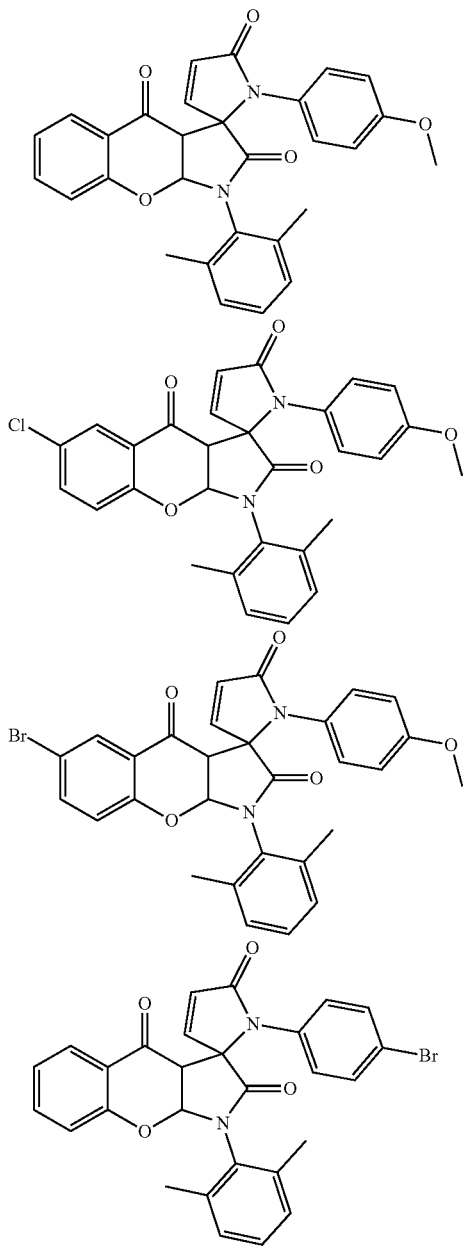

-continued

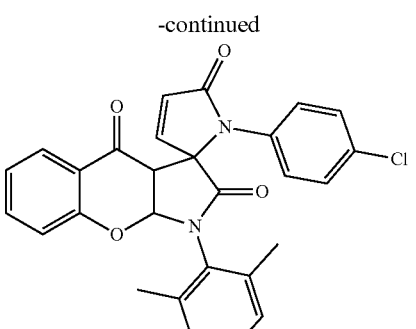

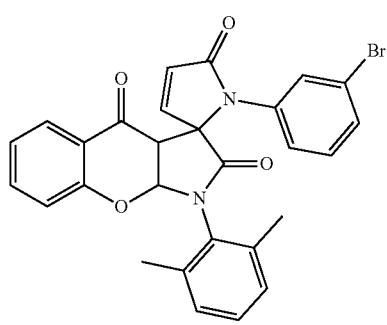

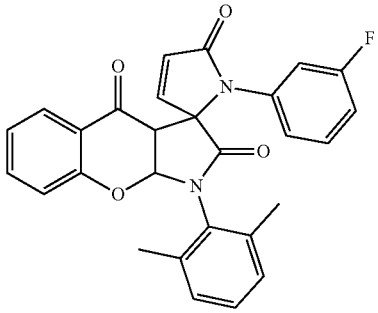

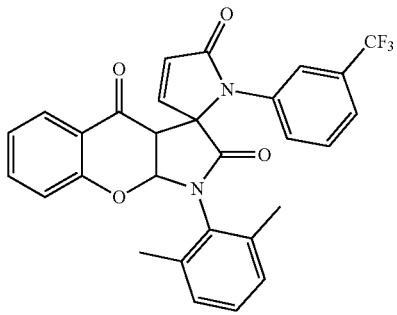

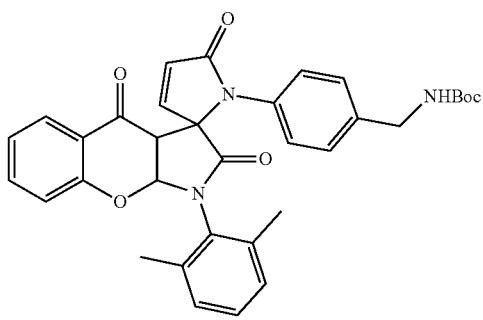

-continued
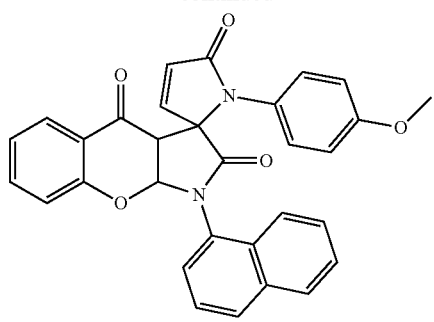
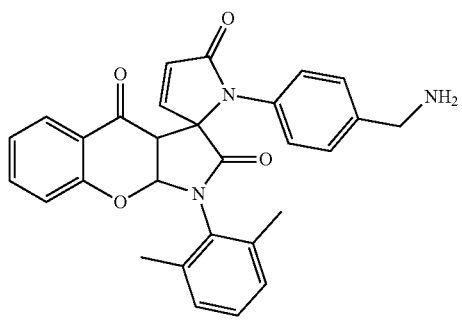
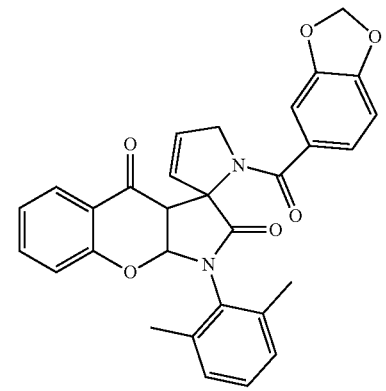
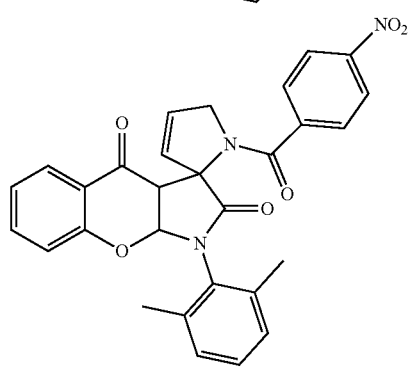
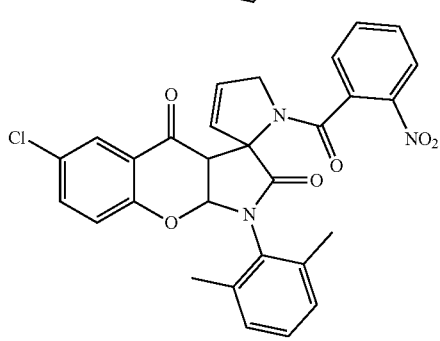
-continued
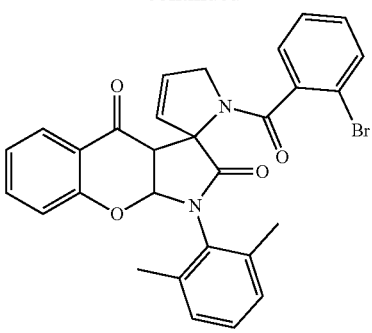
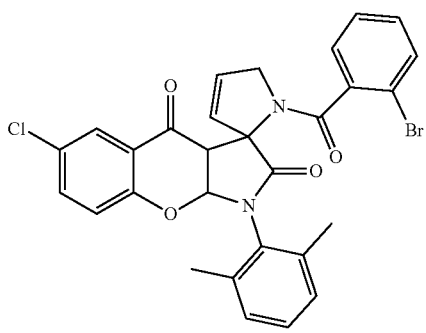
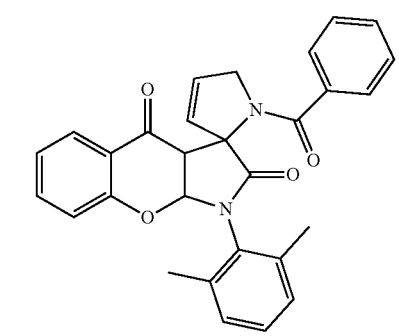
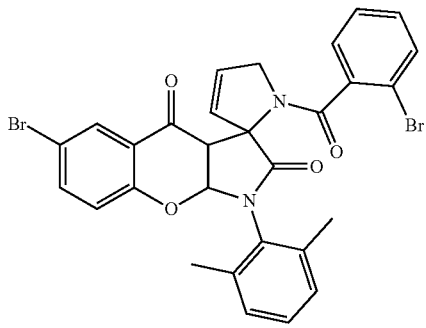
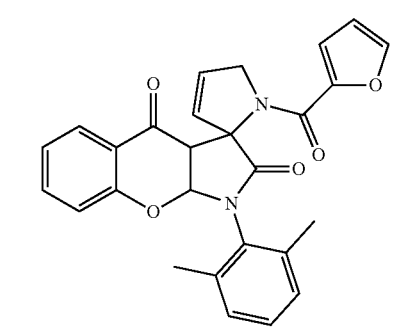

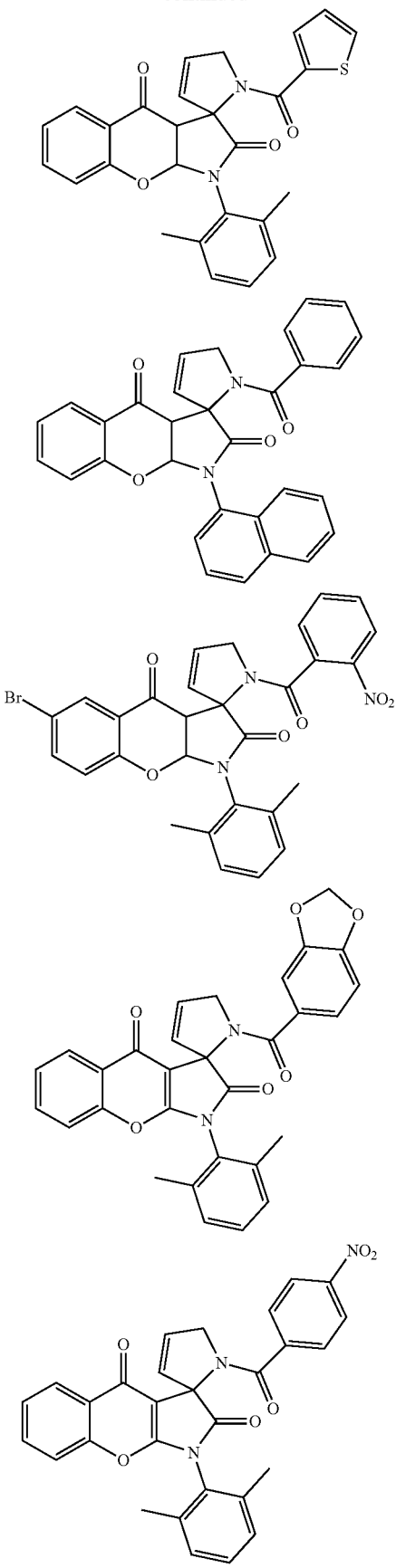
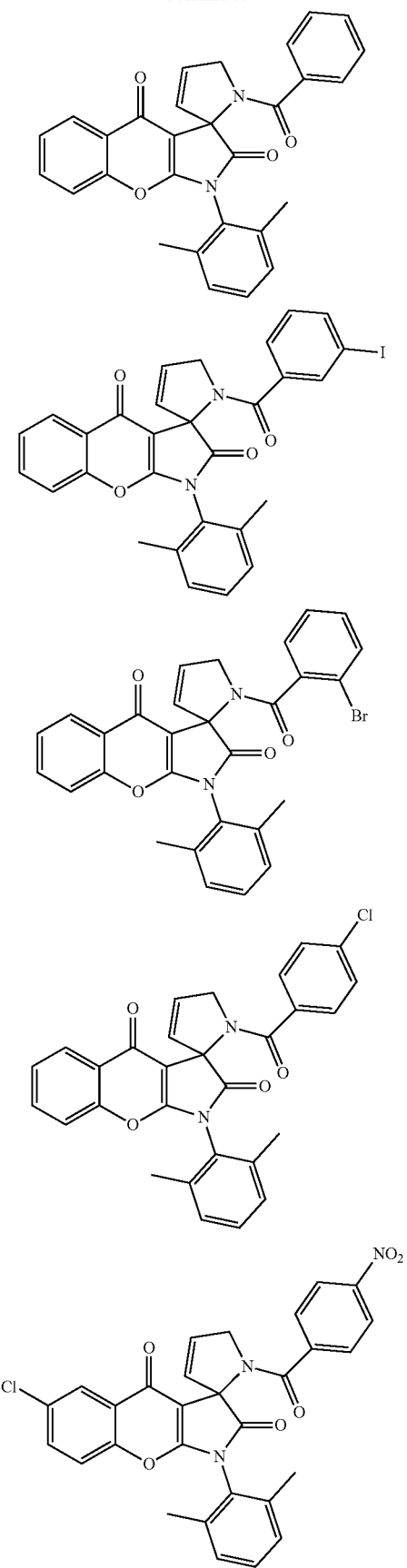

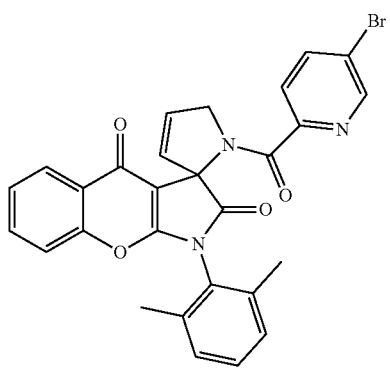
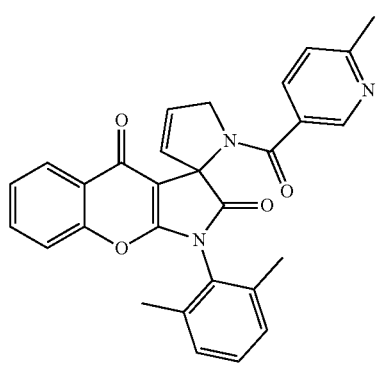
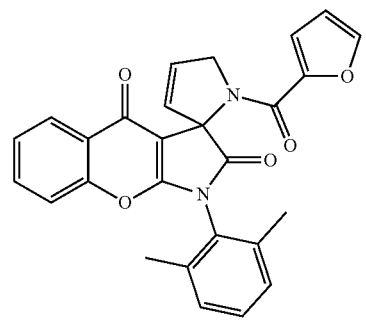
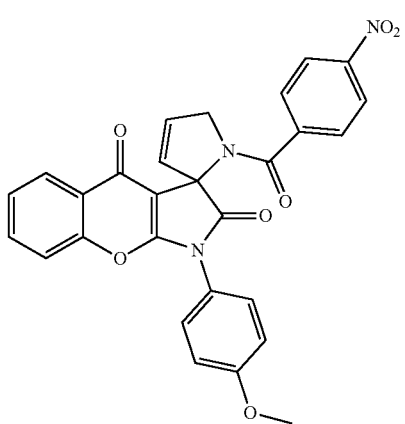
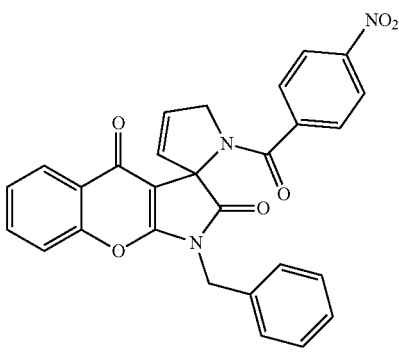
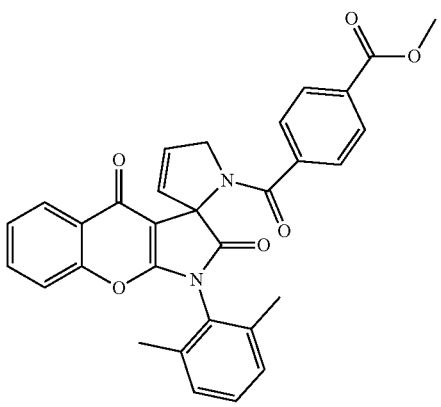
In a further aspect, the present application provides a method for preparing a compound of Formula Ia or a pharmaceutically acceptable salt thereof, comprising Step 1 and Step 2 below:
Step 1: performing a Ugi four-component reaction of Compounds 1, 2, 3 and 4 to obtain Compound 5;
Step 2: reacting Compound 5 to obtain the compound of Formula Ia;
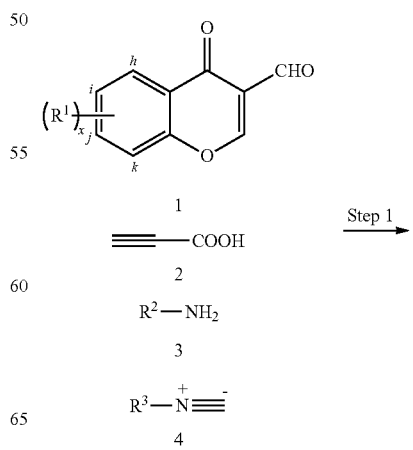

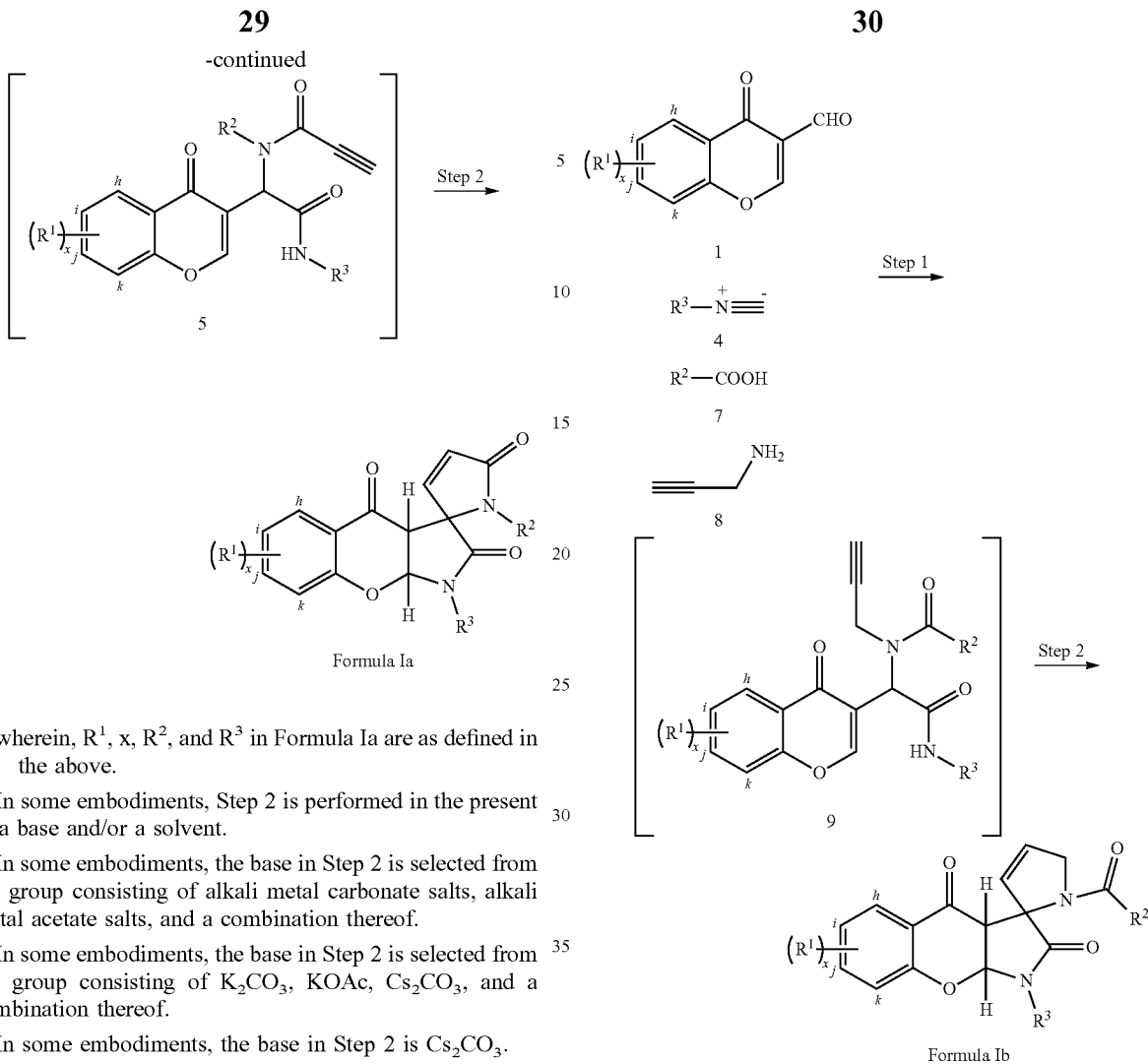

Formula Ia wherein, $R^1$, x, $R^2$, and $R^3$ in Formula Ia are as defined in the above.

In some embodiments, Step 2 is performed in the present of a base and/or a solvent.

In some embodiments, the base in Step 2 is selected from the group consisting of alkali metal carbonate salts, alkali metal acetate salts, and a combination thereof.

In some embodiments, the base in Step 2 is selected from the group consisting of $K_2CO_3$, KOAc, $Cs_2CO_3$, and a combination thereof.

In some embodiments, the base in Step 2 is $Cs_2CO_3$.

In some embodiments, the solvent in Step 2 is selected from the group consisting of MeCN, DMF, and a combination thereof.

In some embodiments, the solvent in Step 2 is MeCN.

In some embodiments, Step 2 is performed with 0.5-5 equiv. (e.g., 0.5, 1, 2, 3, 4, 5 equiv.), 1-3 equiv., or 2 equiv. of the base in the solvent.

In some embodiments, the reaction time of Step 2 is 1-10 h (e.g., 1 h, 2 h, 3 h, 4 h, 5 h, 6 h, 7 h, 8 h, 9 h, 10 h), 1-5 h or 3 h.

In some embodiments, Step 1 is performed in the present of a solvent.

In some embodiments, the solvent in Step 1 is 2,2,2-trifluoroethanol (TFE).

In some embodiments, Step 1 is performed at room temperature.

In still another aspect, the present application provides a method for preparing a compound of Formula Ib or a pharmaceutically acceptable salt thereof, comprising Step 1 and Step 2 below:

Step 1: performing a Ugi four-component reaction of Compounds 1, 4, 7 and 8 to obtain Compound 9;

Step 2: reacting Compound 9 to obtain the compound of Formula Ib;

Formula Ib wherein, $R^1$, x, $R^2$, and $R^3$ in Formula Ib are as defined in the above.

In some embodiments, Step 2 is performed in the present of a base and/or a solvent.

In some embodiments, the base in Step 2 is selected from the group consisting of $Cs_2CO_3$, 1,4-diazabicyclo[2.2.2]octane (DABCO), N,N-diisopropylethylamine (DIPEA), diisopropylamine (DIPA), trimethylamine ($Et_3N$) and a combination thereof.

In some embodiments, the base in Step 2 is DIPA.

In some embodiments, the solvent in Step 2 is selected from the group consisting of MeCN, MeOH, EtOH, and a combination thereof.

In some embodiments, the solvent in Step 2 is EtOH.

In some embodiments, the reaction time of Step 2 is 2-10 h (e.g., 2 h, 3 h, 4 h, 5 h, 6 h, 7 h, 8 h, 9 h, 10 h), 4-8 h or 6 h.

In some embodiments, the reaction temperature of Step 2 is 80° C.-200° C. (e.g., 80° C., 90° C., 100° C., 110° C., 120° C., 130° C., 140° C., 150° C., 160° C., 170° C., 180° C., 190° C., 200° C.), 100° C.-150° C., 120° C.-140° C., or 120° C.

In some embodiments, Step 2 is performed with 0.5-5 equiv. (e.g., 0.5, 1, 2, 3, 4, 5 equiv.), 1-3 equiv., or 2 equiv. of the base in the solvent.

In some embodiments, Step 1 is performed in the present of a solvent.

In some embodiments, the solvent in Step 1 is 2,2,2-trifluoroethanol (TFE).

In some embodiments, Step 1 is performed at room temperature.

In another aspect, the present application provides a method for preparing a compound of Formula Ic or a pharmaceutically acceptable salt thereof, comprising Step 1 and Step 2 below:

Step 1: performing a Ugi four-component reaction of Compounds 1, 4, 7 and 8 to obtain Compound 9;

Step 2: reacting Compound 9 to obtain the compound of Formula Ic;

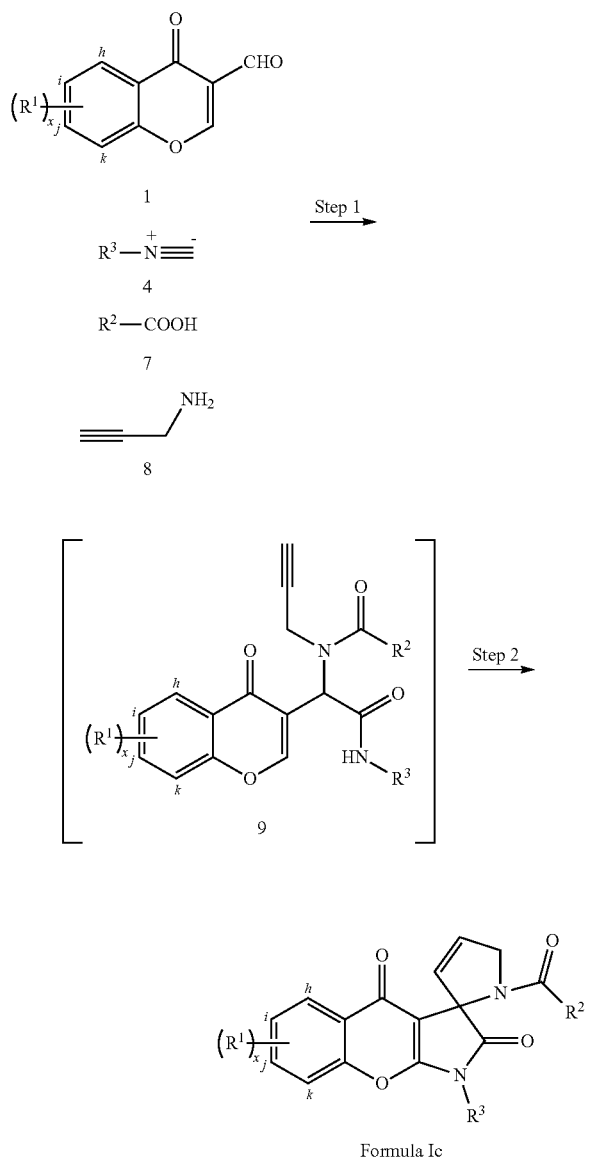

wherein, $R^1$, x, $R^2$, and $R^3$ in Formula Ic are as defined in the above.

In some embodiments, Step 2 is performed in the present of a base and/or a solvent.

In some embodiments, the base in Step 2 is selected from the group consisting of $Cs_2CO_3$, 1,4-diazabicyclo[2.2.2]octane (DABCO), N,N-diisopropylethylamine (DIPEA), diisopropylamine (DIPA), trimethylamine ($Et_3N$) and a combination thereof.

In some embodiments, the base in Step 2 is DIPA.

In some embodiments, the solvent in Step 2 is selected from the group consisting of DMF, EtOH, and a combination thereof.

In some embodiments, the solvent in Step 2 is DMF.

In some embodiments, the reaction time of Step 2 is 2-10 h (e.g., 2 h, 3 h, 4 h, 5 h, 6 h, 7 h, 8 h, 9 h, 10 h), 4-8 h or 6 h.

In some embodiments, the reaction temperature of Step 2 is 80° C.-200° C. (e.g., 80° C., 90° C., 100° C., 110° C., 120° C., 130° C., 140° C., 150° C., 160° C., 170° C., 180° C., 190° C., 200° C.), 100° C.-150° C., 120° C.-140° C., or 120° C.

In some embodiments, Step 2 is performed with 0.5-5 equiv. (e.g., 0.5, 1, 2, 3, 4, 5 equiv.), 1-3 equiv., or 2 equiv. of the base in the solvent.

In some embodiments, Step 1 is performed in the present of a solvent.

In some embodiments, the solvent in Step 1 is 2,2,2-trifluoroethanol (TFE).

In some embodiments, Step 1 is performed at room temperature.

In still another aspect, the present application provides a pharmaceutical composition comprising the compound of formula I or a pharmaceutically acceptable salt thereof according to the present application. In some embodiments, the pharmaceutical composition further comprises one or more pharmaceutically acceptable carriers or excipients.

In a further aspect, the present application provides a method for treating a cancer, comprising administering to a subject in need thereof a therapeutically effective amount of a compound of Formula I or a pharmaceutically acceptable salt thereof according to the present application.

In some embodiments, the cancer is pancreatic cancer.

Herein, series of diastereoselective chromone-spiro-γ-lactams are synthesized under mild reaction conditions and simple operation procedure with good yield, and their effect on cancers was investigated. A post-Ugi one-pot cascade reaction is developed for derivatizing diastereoselective chromanone spiro-γ-lactams with assistant of Michael-type addition to construct spiro-quaternary carbon center without the presence of a catalyst.

EXAMPLES

The purpose of the following specific examples is to facilitate those skilled in the art to more clearly understand and implement the present application. They should not be construed as limiting the scope of the present application, and they are merely exemplary illustrations and typical representatives of the present application.

Preparation Example 1: The Synthesis of Spiro-γ-Lactam Compound 6a

Optimization for Synthesis of Spiro-γ-Lactam Compound 6a

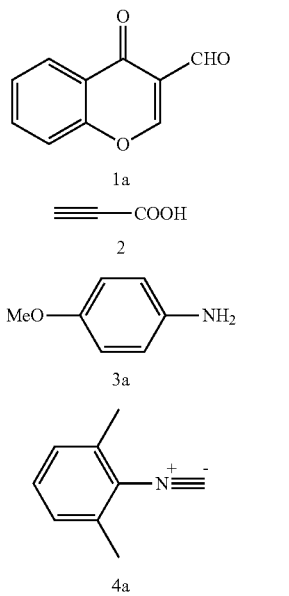

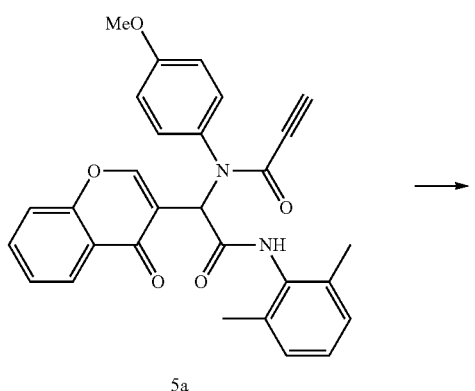

TABLE 1

| No. | base | Solvent | Time (h) | Yield (%)[a] |
|---|---|---|---|---|
| 1 | $K_2CO_3$ | MeCN | 2 | 25 |
| 2 | EtONa | MeCN | 2 | trace |
| 3 | NaOH | MeCN | 2 | complex |
| 4 | KOAc | MeCN | 2 | 17 |
| 5 | t-BuONa | MeCN | 2 | complex |
| 6 | DIPA | MeCN | 2 | NR |
| 7 | DIPEA | MeCN | 2 | NR |
| 8 | DBU | MeCN | 2 | NR |
| 9 | $Cs_2CO_3$ | MeCN | 2 | 65 |
| 10 | $Cs_2CO_3$ | MeCN | 3 | 73 |
| 11 | $Cs_2CO_3$ | MeCN | 4 | 59 |
| 12 | $Cs_2CO_3$ | MeOH | 3 | NR |
| 13 | $Cs_2CO_3$ | Toluene | 3 | trace |
| 14 | $Cs_2CO_3$ | THF | 3 | trace |
| 15 | $Cs_2CO_3$ | Dioxane | 3 | trace |
| 16 | $Cs_2CO_3$ | DMF | 3 | 54 |
| 17 | $Cs_2CO_3$ | DCE | 3 | trace |
| 18[b] | $Cs_2CO_3$ | MeCN | 3 | 55 |
| 19[c] | $Cs_2CO_3$ | MeCN | 3 | 48 |

[a] Reaction conditions (No. 1 to 17): substrate (0.02 mmol), base (2.0 equiv.), solvent (1.0 mL), stirring in the air at room temperature.
[b] 1.0 equiv. of $Cs_2CO_3$ (No. 18).
[c] 3.0 equiv. of $Cs_2CO_3$ (No. 19).

Initially, the highly functionable Ugi product which was constructed via U-4CR of chromone-3-carboxaldehyde 1a, propiolic acid 2, 4-methoxyaniline 3a and 2,6-dimethylphenyl isocyanide 4a in 2,2,2-trifluoroethanol (TFE) at room temperature (Table 1). The crude residue 5a was selected as model substrate with $K_2CO_3$ as base in solvent of methyl cyanide (MeCN). The reaction mixture was left open to air at room temperature. It was found that the reaction gave spiro-γ-lactam 6a in 25% which was confirmed by LC/MS, NMR and X-ray crystallography (Table 1, No. 1). A new scaffold diastereoselective spiro-γ-lactam was generated by formation of C—N bond between amide and olefin $sp^2$ and C—C bond to provide pyrroline.

After confirmed the structure of desired compound, optimization conditions were investigated, including organic bases, inorganic bases and solvents. Under the strong inorganic basic conditions, there was little anticipated product was observed (Table 1, No. 2-5). Among the organic bases, such as DIPA, DIPEA and DBU, there no targeted product was observed (Table 1, No. 6-8). Then, following investigating the inorganic bases, the excited results that $Cs_2CO_3$ shows better efficacy with 65% yield for this reaction (Table 1, No. 9). Prolonging reaction time from 2 h to 3 h, the highest yield was provided with 73% (Table 1, No. 10). However, continuing prolong the reaction time to 4 h, the low yield (59%) was obtained. The effect of solvents (such as MeOH, toluene, THF, dioxane, DMF and DCE) as well as different amounts of $Cs_2CO_3$ (Table 1, No. 18, 19) was employed, either lower yield or a trace amount of product was observed (Table 1, No. 12-17). From the optimization results, it is found that 2.0 equiv. of $Cs_2CO_3$ in MeCN could give the desired product with better yield (Table 1, No. 10).

Preparation Example 2: The Synthesis of Spiro-γ-Lactam Compounds 6a-6k

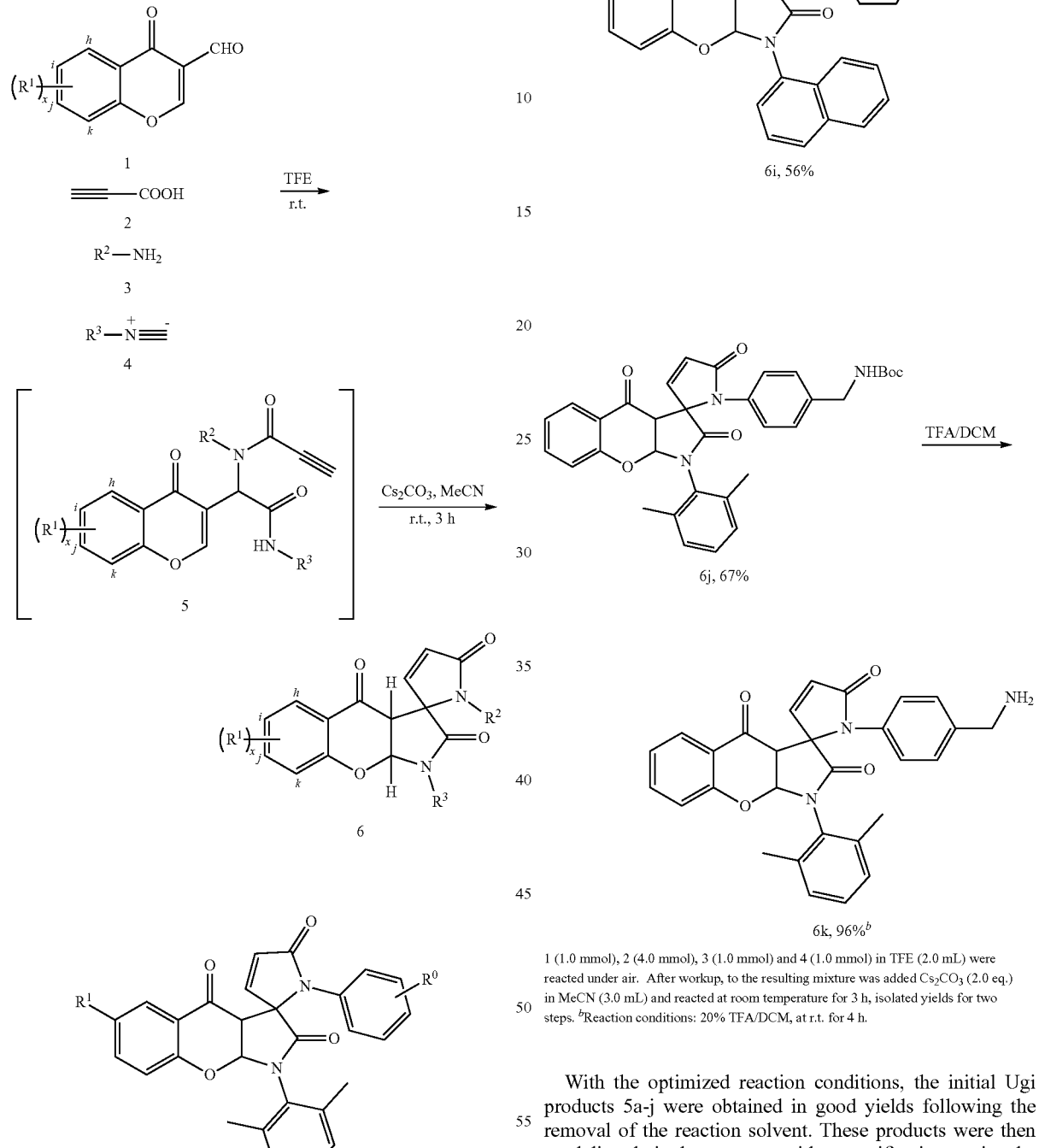

6a, 73%, $R^1$ = H, $R^0$ = 4-MeO;
6b, 65%, $R^1$ = Cl, $R^0$ = 4-MeO;
6c, 66%, $R^1$ = Br, $R^0$ = 4-MeO;
6d, 59%, $R^1$ = H, $R^0$ = 4-Br;
6e, 52%, $R^1$ = H, $R^0$ = 4-Cl;
6f, 70%, $R^1$ = H, $R^0$ = 3-Br;
6g, 68%, $R^1$ = H, $R^0$ = 3-F;
6h, 61%, $R^1$ = H, $R^0$ = 3-$CF_3$.

6i, 56%

6j, 67%

6k, 96%[b]

1 (1.0 mmol), 2 (4.0 mmol), 3 (1.0 mmol) and 4 (1.0 mmol) in TFE (2.0 mL) were reacted under air. After workup, to the resulting mixture was added $Cs_2CO_3$ (2.0 eq.) in MeCN (3.0 mL) and reacted at room temperature for 3 h, isolated yields for two steps. [b]Reaction conditions: 20% TFA/DCM, at r.t. for 4 h.

With the optimized reaction conditions, the initial Ugi products 5a-j were obtained in good yields following the removal of the reaction solvent. These products were then used directly in the next step without purification to give the desired chromone-spiro-γ-lactams 6a-j in 52-73% yields. Deprotected compound 6k from 6j was also obtained for the next screening. Importantly, the reaction can be only carried out with aromatic isocyanides, and aliphatic isocyanides were tested, the relative Ugi product 5 could be found and the following cyclization product could not be obtained. It is noteworthy that the product of Ugi adduct 5 did not require purification by column chromatography, with the crude product having no discernible impact on the overall yield of final products.

37

1-(2,6-dimethylphenyl)-1'-(4-methoxyphenyl)-3a,9a-dihydro-2H-spiro[chromeno[2,3-b]pyrrole-3,2'-pyrrole]-2,4,5'(1H,1'H)-trione

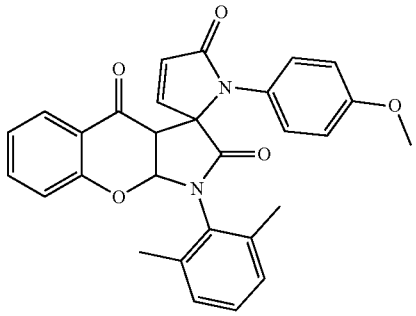 [SMILES: COc1ccc(N2C(=O)C=CC23C(=O)N(c2c(C)cccc2C)C2Oc4ccccc4C(=O)C23)cc1]

6a, 73%, $^1$H NMR (400 MHz, CDCl$_3$) δ 7.87 (dd, J=7.9, 1.5 Hz, 1H), 7.63-7.50 (m, 3H), 7.37 (d, J=8.3 Hz, 2H), 7.24 (dd, J=13.4, 7.7 Hz, 2H), 7.19-7.06 (m, 3H), 7.00 (d, J=8.3 Hz, 1H), 6.40 (d, J=5.9 Hz, 1H), 5.85 (d, J=5.1 Hz, 1H), 4.33 (d, J=5.2 Hz, 2H), 3.64 (d, J=5.1 Hz, 1H), 2.42 (s, 3H), 1.94 (s, 3H), 1.47 (s, 9H). $^{13}$C NMR (100 MHz, CDCl$_3$) δ 186.46, 170.59, 168.81, 159.75, 157.92, 141.32, 137.86, 137.42, 135.00, 133.37, 131.38, 129.51, 129.21, 128.89, 127.02, 123.59, 120.61, 118.63, 114.98, 88.33, 75.85, 55.52, 47.86, 18.55, 17.73.

38

6-bromo-1-(2,6-dimethylphenyl)-1'-(4-methoxyphenyl)-3a,9a-dihydro-2H-spiro[chromeno[2,3-b]pyrrole-3,2'-pyrrole]-2,4,5'(1H,1'H)-trione

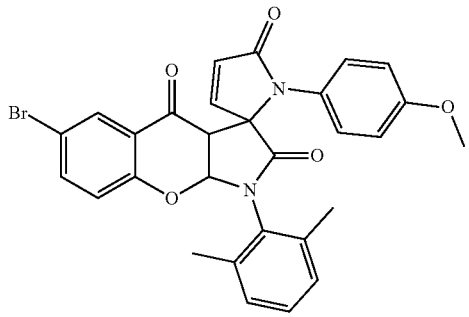

6c, 66%, $^1$H NMR (400 MHz, CDCl$_3$) δ 7.99 (d, J=2.4 Hz, 1H), 7.66 (dd, J=8.8, 2.5 Hz, 1H), 7.51 (d, J=8.9 Hz, 2H), 7.13 (dd, J=8.4, 4.4 Hz, 4H), 6.99 (d, J=8.9 Hz, 2H), 6.92 (d, J=8.8 Hz, 1H), 6.44 (d, J=6.0 Hz, 1H), 5.83 (d, J=5.1 Hz, 1H), 3.83 (s, 3H), 3.69 (d, J=5.1 Hz, 1H), 2.41 (s, 3H), 1.90 (s, 3H). $^{13}$C NMR (100 MHz, CDCl$_3$) δ 185.29, 168.47, 164.52, 159.96, 156.90, 140.93, 140.08, 137.77, 135.30, 131.13, 129.71, 128.96, 128.76, 128.32, 127.79, 120.61, 115.04, 88.51, 75.68, 55.54, 47.61, 18.75, 18.60.

6-chloro-1-(2,6-dimethylphenyl)-1'-(4-methoxyphenyl)-3a,9a-dihydro-2H-spiro[chromeno[2,3-b]pyrrole-3,2'-pyrrole]-2,4,5'(1H,1'H)-trione

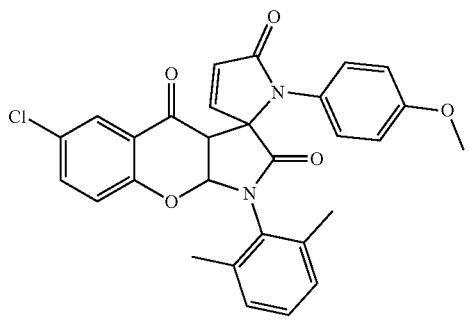 [SMILES: COc1ccc(N2C(=O)C=CC23C(=O)N(c2c(C)cccc2C)C2Oc4ccc(Cl)cc4C(=O)C23)cc1]

6b, 65%, $^1$H NMR (400 MHz, CDCl$_3$) δ 8.35 (s, 1H), 7.83 (d, J=2.6 Hz, 1H), 7.49 (d, J=8.8 Hz, 2H), 7.13 (s, 3H), 7.06 (t, J=4.5 Hz, 3H), 6.95 (s, 1H), 6.42 (d, J=6.0 Hz, 1H), 5.83 (d, J=5.1 Hz, 1H), 3.82 (s, 3H), 3.69 (d, J=5.1 Hz, 1H), 2.41 (s, 3H), 1.89 (s, 3H). $^{13}$C NMR (100 MHz, CDCl$_3$) δ 185.49, 168.59, 164.88, 159.40, 156.30, 137.27, 135.27, 131.09, 129.71, 129.29, 128.96, 128.73, 128.26, 127.73, 126.58, 120.35, 115.11, 88.45, 75.71, 55.61, 47.61, 18.73, 18.56.

1'-(4-bromophenyl)-1-(2,6-dimethylphenyl)-3a,9a-dihydro-2H-spiro[chromeno[2,3-b]pyrrole-3,2'-pyrrole]-2,4,5'(1H,1'H)-trione

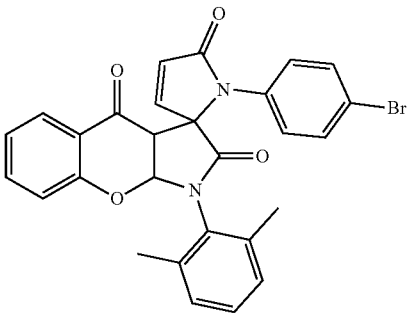 [SMILES: Cc1cccc(C)c1N1C(=O)C2(C=CC(=O)N2c2ccc(Br)cc2)C2C(=O)c3ccccc3OC21]

6d, 59%, $^1$H NMR (400 MHz, CDCl$_3$) δ 8.41 (s, 1H), 8.09 (d, J=11.9 Hz, 1H), 7.87 (dd, J=7.8, 1.2 Hz, 1H), 7.60 (d, J=8.6 Hz, 2H), 7.48 (d, J=8.6 Hz, 2H), 7.15-7.10 (m, 4H), 7.01 (d, J=8.3 Hz, 1H), 6.41 (d, J=6.0 Hz, 1H), 5.86 (d, J=5.0 Hz, 1H), 3.60 (d, J=5.0 Hz, 1H), 2.43 (s, 3H), 1.97 (s, 3H). $^{13}$C NMR (100 MHz, CDCl$_3$) δ 186.26, 170.21, 168.67, 164.69, 159.25, 157.86, 141.78, 137.79, 135.29, 134.87, 132.92, 131.13, 129.64, 129.30, 128.75, 128.30, 127.76, 123.74, 122.77, 120.58, 118.70, 88.17, 75.57, 47.89, 18.58, 17.91.

1'-(4-chlorophenyl)-1-(2,6-dimethylphenyl)-3a,9a-dihydro-2H-spiro[chromeno[2,3-b]pyrrole-3,2'-pyrrole]-2,4,5'(1H,1'H)-trione

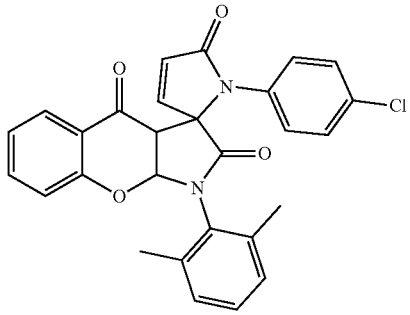 [SMILES: Cc1cccc(C)c1N1C(=O)C2(C=CC(=O)N2c2ccc(Cl)cc2)C2C(=O)c3ccccc3OC21]

6e, 52%, ¹H NMR (400 MHz, CDCl₃) δ 8.42 (s, 1H), 8.10 (d, J=11.9 Hz, 1H), 7.88 (dd, J=7.9, 1.4 Hz, 1H), 7.55 (d, J=8.7 Hz, 2H), 7.45 (d, J=8.6 Hz, 2H), 7.13 (dd, J=5.1, 2.6 Hz, 4H), 7.01 (d, J=8.3 Hz, 1H), 6.42 (d, J=6.0 Hz, 1H), 5.86 (d, J=5.1 Hz, 1H), 3.60 (d, J=5.1 Hz, 1H), 2.43 (s, 3H), 1.97 (s, 3H). ¹³C NMR (100 MHz, CDCl₃) δ 186.27, 170.01, 168.57, 159.27, 157.98, 141.73, 137.57, 135.29, 134.86, 133.30, 131.12, 129.94, 129.63, 129.30, 128.75, 128.31, 127.78, 123.73, 120.58, 118.70, 88.18, 75.62, 47.90, 18.75, 18.58.

1-(2,6-dimethylphenyl)-1'-(3-fluorophenyl)-3a,9a-dihydro-2H-spiro[chromeno[2,3-b]pyrrole-3,2'-pyrrole]-2,4,5'(1H,1'H)-trione

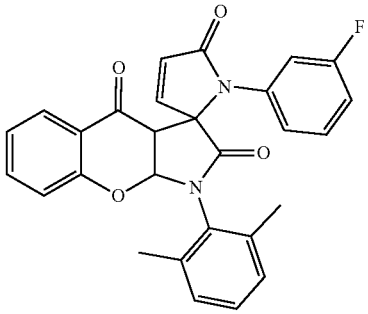

6g, 68%, ¹H NMR (400 MHz, CDCl₃) δ 7.87 (dd, J=7.9, 1.5 Hz, 1H), 7.65-7.54 (m, 1H), 7.46-7.34 (m, 3H), 7.29 (d, J=7.5 Hz, 1H), 7.19-7.06 (m, 5H), 7.01 (d, J=8.3 Hz, 1H), 6.41 (d, J=6.0 Hz, 1H), 5.87 (d, J=5.1 Hz, 1H), 3.63 (d, J=5.1 Hz, 1H), 2.43 (s, 3H), 1.98 (s, 3H). ¹³C NMR (100 MHz, CDCl₃) δ 186.27, 170.13, 168.63, 157.84, 141.85, 137.80, 134.93, 131.05, 130.77, 129.65, 129.28, 129.01, 127.25, 124.94, 123.74, 120.61, 118.72, 116.69, 88.20, 75.62, 47.84, 18.59, 17.68.

1'-(3-bromophenyl)-1-(2,6-dimethylphenyl)-3a,9a-dihydro-2H-spiro[chromeno[2,3-b]pyrrole-3,2'-pyrrole]-2,4,5'(1H,1'H)-trione

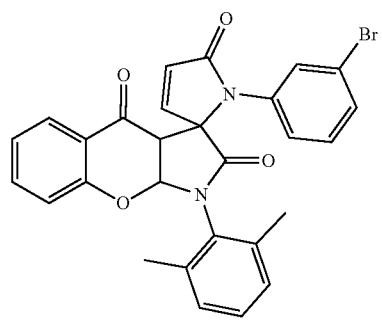 [SMILES: Cc1cccc(C)c1N1C(=O)C2(C=CC(=O)N2c2cccc(Br)c2)C2C(=O)c3ccccc3OC21]

6f, 70%, ¹H NMR (400 MHz, CDCl₃) δ 7.87 (dd, J=7.8, 1.3 Hz, 1H), 7.72 (s, 1H), 7.59 (dd, J=3.8, 2.9 Hz, 2H), 7.53 (dd, J=8.0, 0.8 Hz, 1H), 7.43-7.28 (m, 3H), 7.15 (dd, J=13.2, 5.1 Hz, 3H), 7.01 (d, J=7.9 Hz, 1H), 6.41 (d, J=5.9 Hz, 1H), 5.87 (d, J=5.1 Hz, 1H), 3.61 (d, J=5.0 Hz, 1H), 2.44 (s, 3H), 2.02 (s, 3H). ¹³C NMR (100 MHz, CDCl₃) δ 186.23, 170.12, 168.60, 157.84, 141.89, 137.81, 136.26, 135.02, 131.77, 131.02, 129.66, 129.27, 129.02, 128.13, 127.25, 123.75, 123.03, 120.63, 118.71, 88.22, 75.62, 47.82, 18.59, 17.74.

1-(2,6-dimethylphenyl)-1'-(3-(trifluoromethyl)phenyl)-3a,9a-dihydro-2H-spiro[chromeno[2,3-b]pyrrole-3,2'-pyrrole]-2,4,5'(1H,1'H)-trione

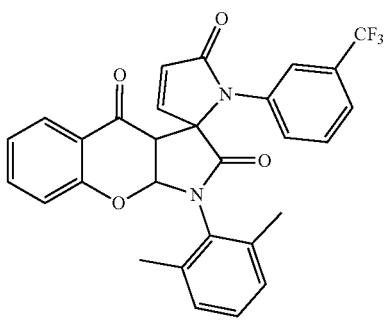 [SMILES: Cc1cccc(C)c1N1C(=O)C2(C=CC(=O)N2c2cccc(C(F)(F)F)c2)C2C(=O)c3ccccc3OC21]

6 h, 61%, ¹H NMR (400 MHz, CDCl₃) δ 7.92-7.81 (m, 3H), 7.68-7.58 (m, 3H), 7.33-7.27 (m, 2H), 7.16 (t, J=7.2 Hz, 3H), 7.02 (d, J=8.3 Hz, 1H), 6.43 (d, J=6.0 Hz, 1H), 5.86 (d, J=5.1 Hz, 1H), 3.55 (d, J=5.0 Hz, 1H), 2.44 (s, 3H), 1.96 (s, 3H). ¹³C NMR (100 MHz, CDCl₃) δ 186.18, 170.25, 168.57, 157.83, 142.08, 137.75, 137.64, 135.64, 134.95, 133.21, 130.95, 130.35, 129.69, 129.30, 129.01, 127.26, 125.74, 125.40, 123.79, 120.58, 118.73, 88.14, 75.59, 47.87, 18.60, 17.53.

Tert-butyl (4-(1-(2,6-dimethylphenyl)-2,4,5'-trioxo-1,3a,4,9a-tetrahydro-2H-spiro[chromeno[2,3-b]pyrrole-3,2'-pyrrol]-1'(5'H)-yl)benzyl)carbamate

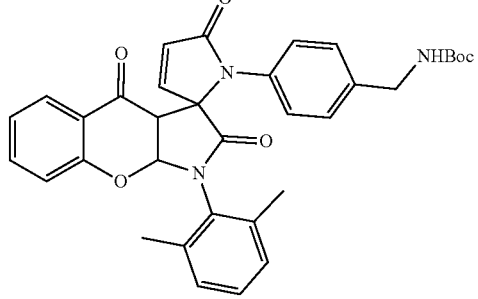

6j, 67%, ¹H NMR (400 MHz, CDCl₃) δ 7.87 (dd, J=7.9, 1.5 Hz, 1H), 7.63-7.50 (m, 3H), 7.37 (d, J=8.3 Hz, 2H), 7.24 (dd, J=13.4, 7.7 Hz, 2H), 7.19-7.06 (m, 3H), 7.00 (d, J=8.3 Hz, 1H), 6.40 (d, J=5.9 Hz, 1H), 5.85 (d, J=5.1 Hz, 1H), 5.02 (s, 1H), 4.33 (d, J=5.2 Hz, 2H), 3.64 (d, J=5.1 Hz, 1H), 2.42 (s, 3H), 1.94 (s, 3H), 1.47 (s, 9H). ¹³C NMR (100 MHz, CDCl₃) δ 186.35, 170.41, 168.78, 157.87, 141.63, 139.69, 137.80, 137.47, 134.99, 133.76, 131.18, 129.52, 129.22, 128.94, 127.22, 123.63, 120.61, 118.67, 88.22, 75.68, 60.39, 47.80, 28.42, 18.58, 17.81.

Preparation Example 3: The Synthesis of Spiro-γ-Lactam Compound 10a

Optimization for Synthesis of Spiro-γ-Lactam Compound 10a

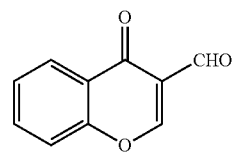

1a

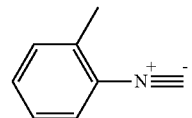

4a

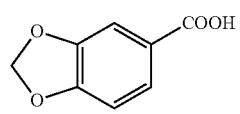

7a

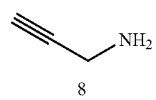

8

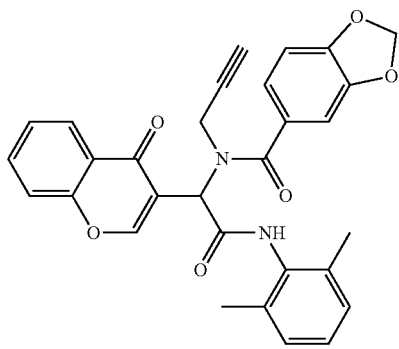

9a

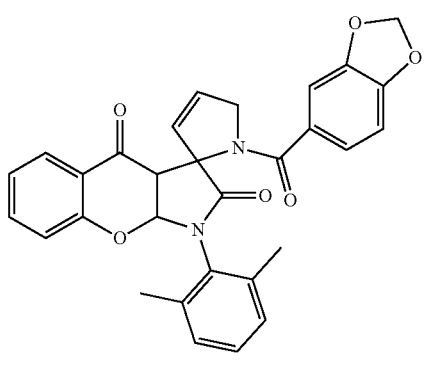

10a or

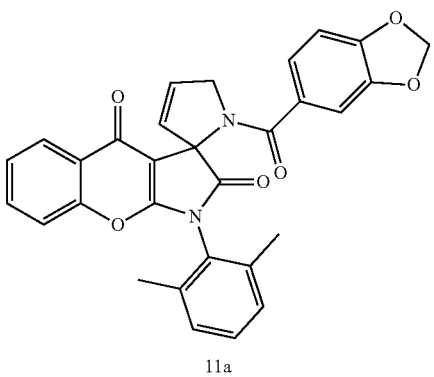

11a

TABLE 2

| No. | base | solvt. | temp. (° C.) | time (h) | Yield (%) 10a [a] | Yield (%) 11a [a] |
|---|---|---|---|---|---|---|
| 1 | Cs₂CO₃ | MeCN | rt | 2 | — | — |
| 2 | Cs₂CO₃ | MeCN | 80 | 2 | 13 | — |
| 3 | Cs₂CO₃ | MeOH | 80 | 2 | 19 | — |
| 4 | Cs₂CO₃ | EtOH | 80 | 2 | 26 | <5 |
| 5 | Cs₂CO₃ | DCE | 80 | 2 | — | — |
| 6 | Cs₂CO₃ | Toluene | 80 | 2 | — | — |

TABLE 2-continued

| No. | base | solvt. | temp. (° C.) | time (h) | Yield (%) 10a[a] | Yield (%) 11a[a] |
|---|---|---|---|---|---|---|
| 7 | Cs$_2$CO$_3$ | DMF | 80 | 2 | <10 | 24 |
| 8 | $^t$BuONa | EtOH | 80 | 2 | — | — |
| 9 | NaOH | EtOH | 80 | 2 | — | — |
| 10 | DABCO | EtOH | 80 | 2 | 35 | <5 |
| 11 | DIPEA | EtOH | 80 | 2 | 28 | <5 |
| 12 | DIPA | EtOH | 80 | 2 | 41 | — |
| 13 | Et$_3$N | EtOH | 80 | 2 | 30 | — |
| 14 | DIPA | EtOH | 100 | 2 | 46 | <10 |
| 15 | DIPA | EtOH | 120 | 2 | 53 | 15 |
| 16 | DIPA | EtOH | 120 | 4 | 66 | 12 |
| 17 | DIPA | EtOH | 120 | 6 | 76 | <10 |
| 18 | DIPA | EtOH | 120 | 8 | 55 | <10 |
| 19 | DIPA | EtOH | 140 | 6 | 62 | — |
| 20 | DIPA | DMF | 120 | 6 | 13 | 68 |
| 21 | DIPA | DMF | 120 | 8 | <10 | 52 |
| 22 | DIPA | DMF | 140 | 6 | — | 39 |

[a]Reaction conditions: substrate (0.02 mmol), base (2.0 equiv.), solvent (1.0 mL), stirring under air.

To expeditiously chemical diversity of biologically active spiro-γ-lactams via a post-Ugi reaction, the feasibility using this method to build increasingly elaborate molecular scaffolds was investigated. As shown in the above scheme, spiro-quaternary carbon center was formed by triple bond closing the 5-member ring. It was investigated that if the triple bond from other Ugi inputs still could from spiro-quaternary carbon. So, prop-2-yn-1-amine with a triple bond at the ending was selected as the source of amine part in Ugi starting material. Similarly to the synthesis of Ugi adduct 5, the U-4CR with chromone-3-carboxaldehyde 1a, 2,6-dimethylphenyl isocyanide 4a, carboxylic acid 7a, and prop-2-yn-1-amine 8 progressed smoothly to afford Ugi adduct 9a. Interesting, the targeted diastereoselective compound 10a was obtained and the structure was proved by X-ray crystallography of its substituted product 10k. The optimal synthesis condition was investigated herein (Table 2).

Based on the optimal conditions for compound 6, the use of Cs$_2$CO$_3$, $^t$BuONa and NaOH at different temperatures and solvents gave compound 10a up to 26% yields (Table 2, No. 1-9). However, the use of 1,4-diazabicyclo[2.2.2]octane (DABCO), N,N-diisopropylethylamine (DIPEA), diisopropylamine (DIPA), and trimethylamine (Et$_3$N) afforded the higher 41% yield (Table 2, No. 10-13). Further increase of the reaction temperature to 120° C. and prolong the reaction time to 6 h, the yield was obtained in 76% (Table 2, No. 17). However, further higher temperature and longer time decreased the yields (Table 2, No. 18-19). Then, to replace EtOH with DMF, another byproduct 11a was obtained with 6 h reaction time. It is noteworthy that the unexpected product was the oxidation formation of 10a and the structure was confirmed by LC/MS, NMR and its substituted product 11l was proved by X-ray crystallography (the Scheme below).

Preparation Example 4: The Synthesis of Spiro-γ-Lactam Compounds 10a-10k

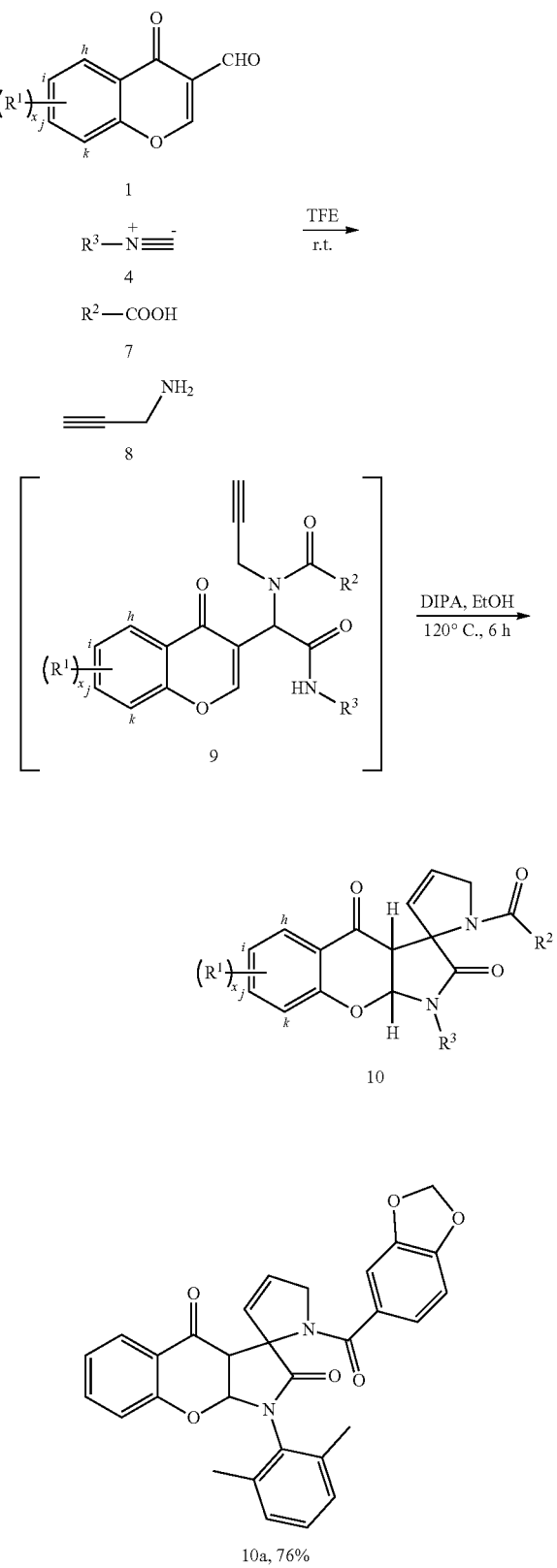

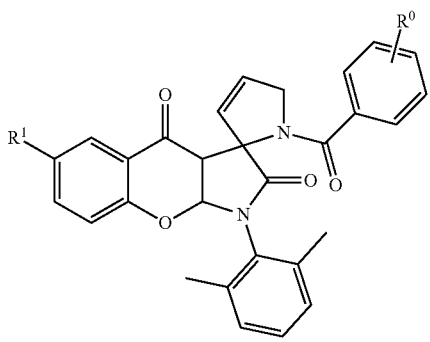

10b, 80%, R¹ = H, R⁰ = 4-NO₂;
10c, 70%, R¹ = Cl, R⁰ = 2-NO₂;
10d, 74%, R¹ = H, R⁰ = 2-Br;
10e, 65%, R¹ = Cl, R⁰ = 2-Br;
10f, 78%, R¹ = H, R⁰ = H;
10g, 72%, R¹ = Br, R⁰ = 2-Br.

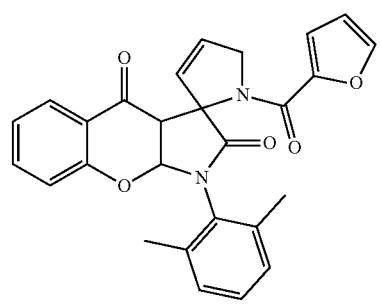

10h, 66%

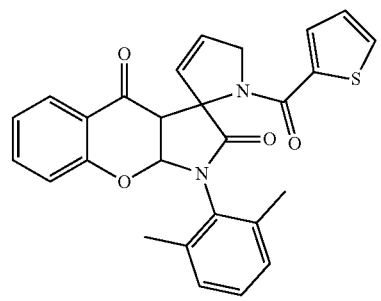

10i, 69%

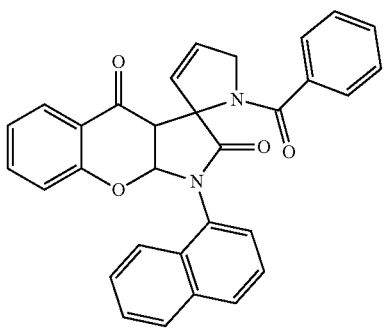

10j, 64%

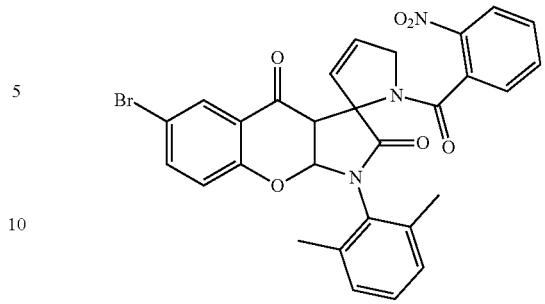

10k, 75%

1 (1.0 mmol), 4 (1.0 mmol), 7 (1.0 mmol) and 8 (1.0 mmol) in TFE (2.0 mL) were reacted under air. After workup, to the resulting mixture was added DIPA (2.0 eq.) in EtOH (3.0 mL), and reacted at 120° C. for 6 h, isolated yields for two steps.

Following the similar procedure of synthesizing compound 6, the crude Ugi product 9 was subjected to a standard work-up procedure (i.e., extraction and solvent evaporation), followed by cyclization cascade reaction under basic conditions to afford compound 10. Different starting materials were successfully employed under the optimized conditions for the construction of structurally diverse spiro-γ-lactam 10a-k with yields in the range of 64-80%. As the same of preparation of spiro-γ-lactam 6, only aromatic isocyanides could afford the diastereoselective spiro-quaternary carbon center and aliphatic isocyanides in Ugi inputs still failed to targeted products.

1'-(benzo[d][1,3]dioxole-5-carbonyl)-1-(2,6-dimethylphenyl)-1',3a,5',9a-tetrahydro-2H-spiro[chromeno[2,3-b]pyrrole-3,2'-pyrrole]-2,4(1H)-dione

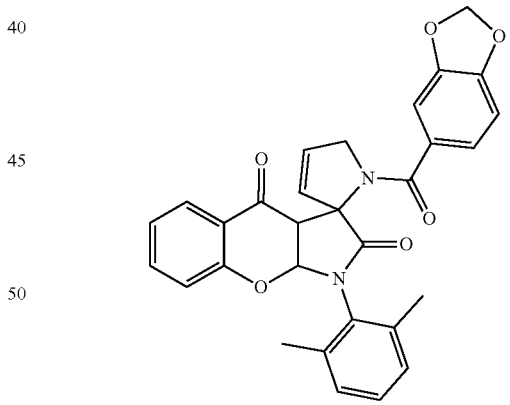

10a, 76%, ¹H NMR (400 MHz, CDCl₃) δ 7.89 (dd, J=7.8, 1.6 Hz, 1H), 7.57-7.51 (m, 1H), 7.24 (d, J=7.4 Hz, 1H), 7.22-7.14 (m, 3H), 7.14-7.09 (m, 2H), 6.97 (d, J=8.2 Hz, 1H), 6.85 (d, J=8.0 Hz, 1H), 6.04 (d, J=5.4 Hz, 1H), 6.01 (t, J=2.5 Hz, 2H), 5.99 (d, J=2.0 Hz, 1H), 5.76 (d, J=6.4 Hz, 1H), 4.67 (d, J=5.4 Hz, 1H), 4.48 (dd, J=9.6, 7.6 Hz, 1H), 4.34 (dd, J=9.5, 7.5 Hz, 1H), 2.48 (s, 3H), 2.41 (s, 3H). ¹³C NMR (100 MHz, CDCl₃) δ 189.91, 169.86, 168.85, 158.62, 149.16, 147.65, 138.00, 136.99, 130.94, 128.96, 128.61, 126.82, 125.38, 122.89, 121.49, 118.71, 108.28, 107.68, 101.44, 88.79, 76.28, 56.87, 48.90, 18.47, 17.67.

1-(2,6-dimethylphenyl)-1'-(4-nitrobenzoyl)-1',3a,5',9a-tetrahydro-2H-spiro[chromeno[2,3-b]pyrrole-3,2'-pyrrole]-2,4(1H)-dione

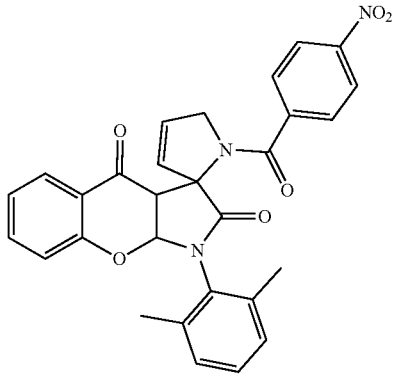 [SMILES: Cc1cccc(C)c1N1C(=O)C2(C=CCN2C(=O)c2ccc([N+](=O)[O-])cc2)C2C(=O)c3ccccc3OC21]

10b, 80%, ¹H NMR (400 MHz, CDCl₃) δ 8.33 (d, J=8.6 Hz, 2H), 7.90 (d, J=7.8 Hz, 1H), 7.80 (d, J=8.6 Hz, 2H), 7.57 (t, J=7.0 Hz, 1H), 7.24-7.17 (m, 2H), 7.17-7.09 (m, 2H), 7.00 (d, J=8.3 Hz, 1H), 6.06 (d, J=5.4 Hz, 1H), 6.00 (d, J=6.3 Hz, 1H), 5.81 (d, J=6.4 Hz, 1H), 4.71 (d, J=5.4 Hz, 1H), 4.39 (d, J=14.7 Hz, 1H), 4.24 (d, J=14.7 Hz, 1H), 2.47 (s, 3H), 2.42 (s, 3H). ¹³C NMR (100 MHz, CDCl₃) δ 189.77, 167.47, 158.60, 141.85, 137.92, 137.25, 136.50, 130.52, 129.14, 128.74, 127.81, 126.86, 125.54, 124.04, 123.11, 121.42, 118.80, 88.67, 56.67, 48.84, 29.70, 18.46, 17.60.

6-chloro-1-(2,6-dimethylphenyl)-1'-(2-nitrobenzoyl)-1',3a,5',9a-tetrahydro-2H-spiro[chromeno[2,3-b]pyrrole-3,2'-pyrrole]-2,4(1H)-dione

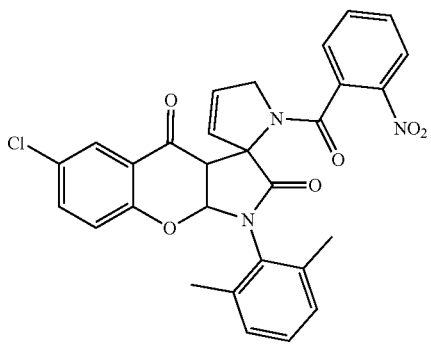 [SMILES: Cc1cccc(C)c1N1C(=O)C2(C=CCN2C(=O)c2ccccc2[N+](=O)[O-])C2C(=O)c3cc(Cl)ccc3OC21]

10c, 70%, ¹H NMR (400 MHz, CDCl₃) δ 8.27 (d, J=8.1 Hz, 1H), 7.86 (d, J=2.6 Hz, 1H), 7.77 (t, J=7.5 Hz, 1H), 7.63 (t, J=8.0 Hz, 2H), 7.48 (dd, J=8.8, 2.6 Hz, 1H), 7.26-7.14 (m, 3H), 6.96 (d, J=8.8 Hz, 1H), 6.07 (d, J=5.5 Hz, 1H), 6.01 (d, J=6.3 Hz, 1H), 5.76 (d, J=6.3 Hz, 1H), 4.90 (d, J=5.5 Hz, 1H), 4.17 (d, J=1.9 Hz, 2H), 2.45 (s, 3H), 2.41 (s, 3H). ¹³C NMR (100 MHz, CDCl₃) δ 188.35, 169.41, 165.95, 156.79, 144.75, 137.84, 136.73, 136.54, 134.79, 133.53, 132.09, 130.83, 130.43, 129.14, 128.68, 126.42, 125.34, 124.72, 122.44, 120.37, 89.00, 75.73, 55.58, 48.56, 18.44, 17.58.

1'-(2-bromobenzoyl)-1-(2,6-dimethylphenyl)-1',3a,5',9a-tetrahydro-2H-spiro[chromeno[2,3-b]pyrrole-3,2'-pyrrole]-2,4(1H)-dione

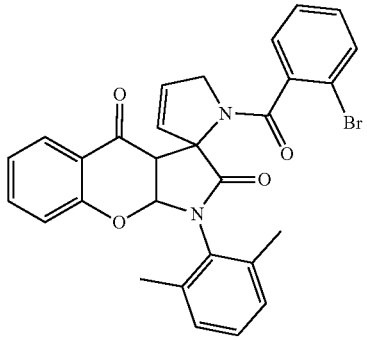 [SMILES: Cc1cccc(C)c1N1C(=O)C2(C=CCN2C(=O)c2ccccc2Br)C2C(=O)c3ccccc3OC21]

10d, 74%, ¹H NMR (400 MHz, CDCl₃) δ 7.89 (d, J=7.8 Hz, 1H), 7.62 (d, J=8.0 Hz, 1H), 7.55 (dd, J=11.3, 4.2 Hz, 1H), 7.46-7.36 (m, 2H), 7.29 (dd, J=9.3, 2.8 Hz, 1H), 7.26-7.16 (m, 3H), 7.12 (t, J=7.5 Hz, 1H), 6.98 (d, J=8.3 Hz, 1H), 6.07 (d, J=5.5 Hz, 1H), 5.99 (d, J=6.3 Hz, 1H), 5.77 (d, J=6.3 Hz, 1H), 4.86 (d, J=5.4 Hz, 1H), 4.21 (d, J=12.9 Hz, 2H), 2.48 (s, 3H), 2.42 (s, 3H). ¹³C NMR (100 MHz, CDCl₃) δ 189.60, 170.22, 169.70, 167.47, 158.50, 138.05, 137.95, 136.99, 133.72, 132.96, 130.88, 129.05, 128.64, 127.83, 126.86, 125.37, 122.99, 121.58, 118.72, 88.81, 75.71, 55.74, 48.72, 18.45, 17.71.

1'-(2-bromobenzoyl)-6-chloro-1-(2,6-dimethylphenyl)-1',3a,5',9a-tetrahydro-2H-spiro[chromeno[2,3-b]pyrrole-3,2'-pyrrole]-2,4(1H)-dione

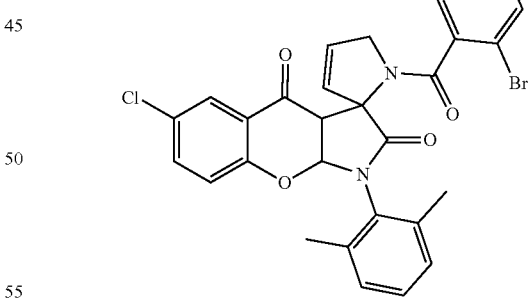

10e, 65%, ¹H NMR (400 MHz, CDCl₃) δ 7.84 (d, J=2.6 Hz, 1H), 7.62 (d, J=8.0 Hz, 1H), 7.48 (dd, J=8.8, 2.6 Hz, 1H), 7.44-7.36 (m, 2H), 7.29 (dd, J=10.0, 4.1 Hz, 1H), 7.22 (dd, J=19.6, 7.7 Hz, 3H), 6.95 (d, J=8.8 Hz, 1H), 6.06 (d, J=5.5 Hz, 1H), 6.01 (d, J=6.3 Hz, 1H), 5.73 (d, J=6.3 Hz, 1H), 4.88 (d, J=5.4 Hz, 1H), 4.19 (t, J=15.7 Hz, 2H), 2.48 (s, 3H), 2.40 (s, 3H). ¹³C NMR (100 MHz, CDCl₃) δ 188.51, 169.42, 167.51, 156.90, 137.94, 136.75, 133.59, 132.98, 131.17, 130.80, 129.12, 128.66, 127.83, 126.29, 125.08, 122.27, 120.37, 89.10, 75.64, 55.72, 48.46, 18.42, 17.68.

1'-benzoyl-1-(2,6-dimethylphenyl)-1',3a,5',9a-tetrahydro-2H-spiro[chromeno[2,3-b]pyrrole-3,2'-pyrrole]-2,4(1H)-dione

1-(2,6-dimethylphenyl)-1'-(furan-2-carbonyl)-1',3a,5',9a-tetrahydro-2H-spiro[chromeno[2,3-b]pyrrole-3,2'-pyrrole]-2,4(1H)-dione

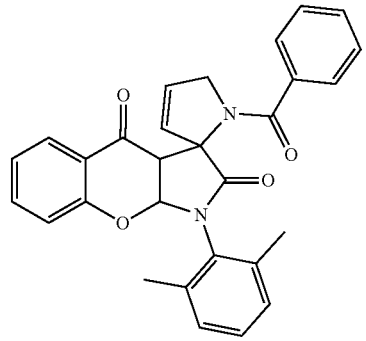 [SMILES: Cc1cccc(C)c1N1C(=O)C2(C=CCN2C(=O)c2ccccc2)C2C(=O)c3ccccc3OC21]

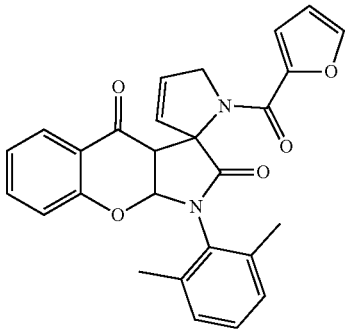 [SMILES: Cc1cccc(C)c1N1C(=O)C2(C=CCN2C(=O)c2ccco2)C2C(=O)c3ccccc3OC21]

10f, 78%, $^1$H NMR (400 MHz, CDCl$_3$) δ 7.89 (d, J=7.8 Hz, 1H), 7.65-7.58 (m, 2H), 7.57-7.51 (m, 1H), 7.28-7.07 (m, 7H), 6.98 (d, J=8.3 Hz, 1H), 6.05 (d, J=5.4 Hz, 1H), 5.98 (d, J=6.3 Hz, 1H), 5.77 (d, J=6.2 Hz, 1H), 4.73 (d, J=5.4 Hz, 1H), 4.21 (d, J=12.9 Hz, 2H), 2.48 (s, 3H), 2.42 (s, 3H). $^{13}$C NMR (100 MHz, CDCl$_3$) δ 189.92, 169.90, 169.63, 158.62, 137.99, 137.03, 136.71, 130.97, 130.14, 128.98, 128.62, 126.82, 125.36, 122.92, 118.72, 88.80, 76.17, 56.79, 48.92, 18.47, 17.66.

10 h, 66%, $^1$H NMR (400 MHz, CDCl$_3$) δ 7.87 (dd, J=7.8, 1.5 Hz, 1H), 7.57 (t, J=2.8 Hz, 1H), 7.55-7.50 (m, 1H), 7.23 (t, J=5.2 Hz, 2H), 7.21-7.15 (m, 2H), 7.09 (d, J=6.6 Hz, 1H), 6.96 (d, J=8.2 Hz, 1H), 6.53 (dd, J=3.4, 1.7 Hz, 1H), 6.11 (d, J=6.4 Hz, 1H), 6.04 (d, J=5.5 Hz, 1H), 5.77 (d, J=6.4 Hz, 1H), 4.92 (d, J=15.4 Hz, 1H), 4.85 (d, J=15.5 Hz, 1H), 4.76 (d, J=5.5 Hz, 1H), 2.50 (s, 3H), 2.40 (s, 3H). $^{13}$C NMR (100 MHz, CDCl$_3$) δ 189.84, 169.72, 158.53, 157.31, 147.82, 144.84, 138.03, 136.94, 131.09, 128.86, 128.62, 126.90, 124.73, 122.84, 121.55, 118.67, 117.68, 111.77, 88.70, 77.24, 55.68, 48.50, 18.53, 17.83.

6-bromo-1'-(2-bromobenzoyl)-1-(2,6-dimethylphenyl)-1',3a,5',9a-tetrahydro-2H-spiro[chromeno[2,3-b]pyrrole-3,2'-pyrrole]-2,4(1H)-dione

1-(2,6-dimethylphenyl)-1'-(thiophene-2-carbonyl)-1',3a,5',9a-tetrahydro-2H-spiro[chromeno[2,3-b]pyrrole-3,2'-pyrrole]-2,4(1H)-dione

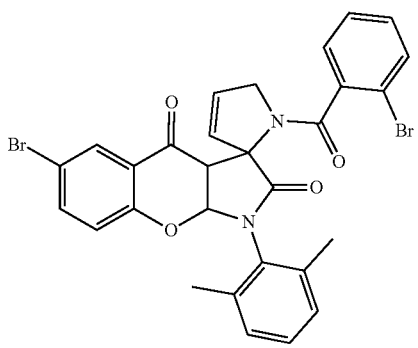

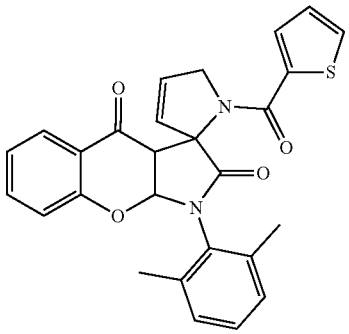 [SMILES: Cc1cccc(C)c1N1C(=O)C2(C=CCN2C(=O)c2cccs2)C2C(=O)c3ccccc3OC21]

10g, 72%, $^1$H NMR (400 MHz, CDCl$_3$) δ 7.99 (d, J=2.4 Hz, 1H), 7.67-7.58 (m, 2H), 7.40 (d, J=7.2 Hz, 2H), 7.33-7.26 (m, 2H), 7.20 (dd, J=17.1, 9.9 Hz, 2H), 6.89 (d, J=8.8 Hz, 1H), 6.06 (d, J=5.5 Hz, 1H), 6.05-5.96 (m, 1H), 5.72 (d, J=6.3 Hz, 1H), 4.88 (d, J=5.4 Hz, 1H), 4.19 (t, J=15.5 Hz, 2H), 2.47 (s, 3H), 2.40 (s, 3H). $^{13}$C NMR (100 MHz, CDCl$_3$) δ 188.37, 167.52, 157.37, 139.57, 137.93, 136.66, 133.57, 132.98, 131.20, 130.81, 129.41, 129.13, 128.66, 127.84, 125.05, 122.68, 120.68, 118.66, 115.75, 89.07, 75.63, 55.71, 48.43, 18.42, 17.68.

10i, 69%, $^1$H NMR (400 MHz, CDCl$_3$) δ 7.87 (dd, J=7.8, 1.5 Hz, 1H), 7.69 (d, J=3.7 Hz, 1H), 7.58-7.49 (m, 2H), 7.24 (d, J=7.4 Hz, 1H), 7.21-7.15 (m, 2H), 7.15-7.06 (m, 2H), 6.97 (d, J=8.3 Hz, 1H), 6.11 (d, J=6.3 Hz, 1H), 6.05 (d, J=5.5 Hz, 1H), 5.80 (d, J=6.4 Hz, 1H), 4.80 (d, J=2.0 Hz, 2H), 4.75 (d, J=5.5 Hz, 1H), 2.50 (s, 3H), 2.40 (s, 3H). $^{13}$C NMR (100 MHz, CDCl$_3$) δ 189.86, 169.62, 161.32, 158.55, 138.03, 137.89, 136.97, 136.72, 133.78, 130.86, 130.65, 128.92, 128.61, 127.33, 126.88, 125.40, 122.88, 121.54, 118.70, 88.68, 77.22, 60.38, 56.33, 18.53, 17.86.

1'-benzoyl-6-chloro-1-(naphthalen-1-yl)-1',3a, 5',9a-tetrahydro-2H-spiro[chromeno[2,3-b]pyrrole-3,2'-pyrrole]-2,4(1H)-dione

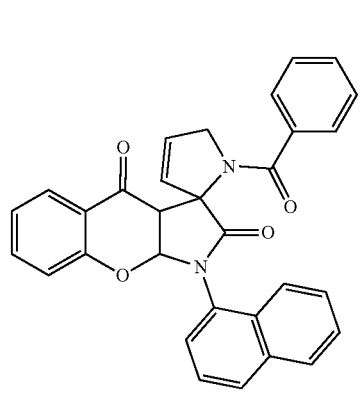 [SMILES: O=C1c2ccccc2OC2C1C1(C=CCN1C(=O)c1ccccc1)C(=O)N2c1cccc2ccccc12]

10j, 64%, $^1$H NMR (400 MHz, CDCl$_3$) δ 7.98-7.89 (m, 3H), 7.79 (d, J=7.3 Hz, 1H), 7.71-7.62 (m, 3H), 7.56 (ddd, J=11.3, 10.1, 5.3 Hz, 4H), 7.49-7.43 (m, 3H), 7.13 (t, J=7.5 Hz, 1H), 7.05 (d, J=8.2 Hz, 1H), 6.11 (d, J=5.0 Hz, 1H), 6.00 (d, J=6.3 Hz, 1H), 5.83 (d, J=6.2 Hz, 1H), 4.86 (d, J=5.2 Hz, 1H), 4.48 (d, J=15.0 Hz, 1H), 4.30 (d, J=15.0 Hz, 1H). $^{13}$C NMR (100 MHz, CDCl$_3$) δ 190.00, 171.06, 169.72, 158.68, 137.04, 136.18, 134.55, 130.87, 130.21, 129.56, 128.60, 128.21, 126.85, 126.76, 125.55, 125.34, 123.40, 123.01, 121.57, 118.85, 76.23, 56.89, 49.36.

6-bromo-1-(2,6-dimethylphenyl)-1'-(2-nitrobenzoyl)-1',3a,5',9a-tetrahydro-2H-spiro[chromeno[2,3-b]pyrrole-3,2'-pyrrole]-2,4(1H)-dione

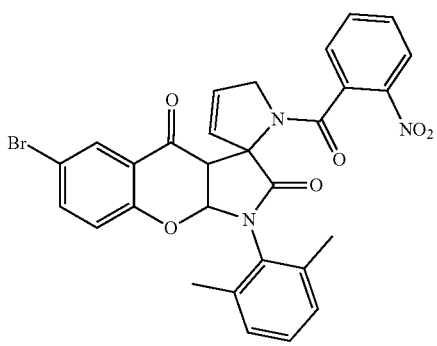 [SMILES: Cc1cccc(C)c1N1C(=O)C2(C=CCN2C(=O)c2ccccc2[N+](=O)[O-])C2C(=O)c3cc(Br)ccc3OC21]

10k, 75%, $^1$H NMR (400 MHz, CDCl$_3$) δ 8.26 (d, J=8.2 Hz, 1H), 8.01 (d, J=2.5 Hz, 1H), 7.77 (t, J=7.5 Hz, 1H), 7.62 (dd, J=10.7, 4.1 Hz, 3H), 7.26-7.15 (m, 3H), 6.90 (d, J=8.8 Hz, 1H), 6.07 (d, J=5.5 Hz, 1H), 6.00 (d, J=6.3 Hz, 1H), 5.75 (d, J=6.3 Hz, 1H), 4.90 (d, J=5.5 Hz, 1H), 4.17 (d, J=2.2 Hz, 2H), 2.44 (s, 3H), 2.41 (s, 3H). $^{13}$C NMR (100 MHz, CDCl$_3$) δ 188.19, 169.39, 165.95, 157.27, 144.78, 139.52, 137.84, 136.55, 134.76, 133.53, 132.09, 130.83, 129.53, 129.14, 128.68, 128.52, 125.34, 124.71, 122.85, 120.67, 115.83, 88.99, 75.74, 55.58, 48.53, 18.43, 17.57.

Preparation Example 5: The Synthesis of Compounds 11a-11m

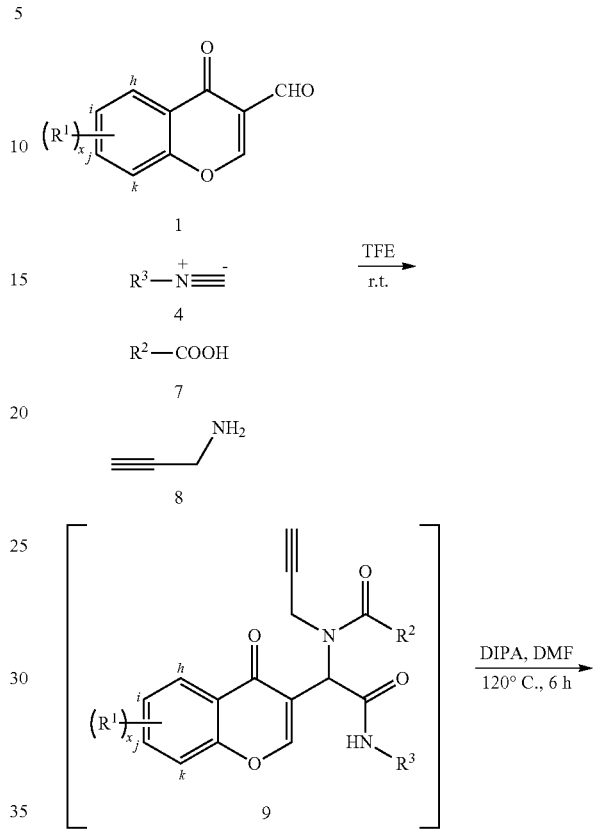

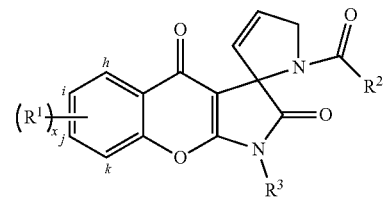

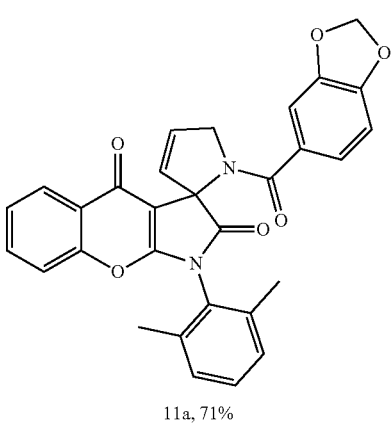

11a, 71%

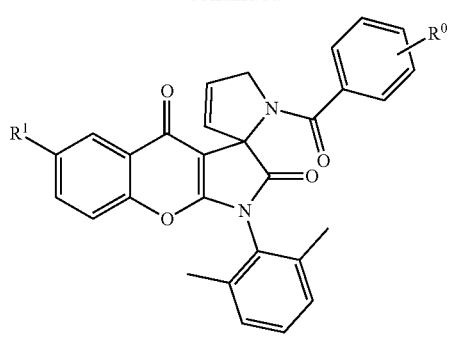

11b, 69%, R¹ = H, R⁰ = 4-NO₂;
11c, 70%, R¹ = H, R⁰ = H;
11d, 72%, R¹ = H, R⁰ = 3-I;
11e, 67%, R¹ = H, R⁰ = 2-Br;
11f, 71%, R¹ = H, R⁰ = 4-Cl;
11g, 76%, R¹ = Cl, R⁰ = 4-NO₂.

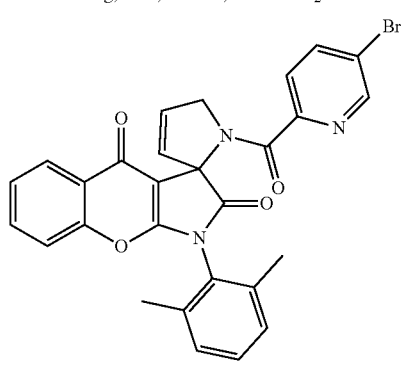

11h, 59%

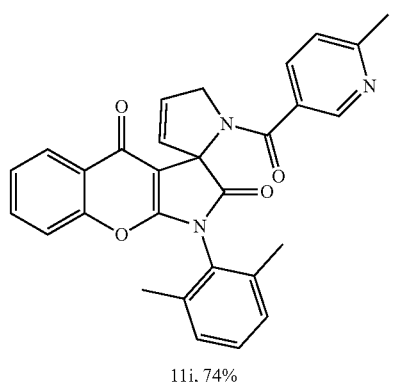

11i, 74%

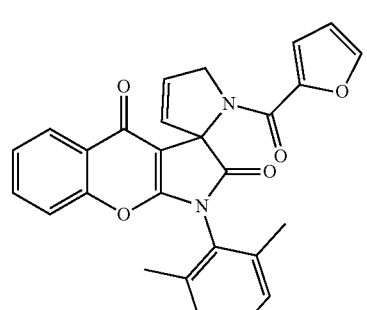

11j, 72%

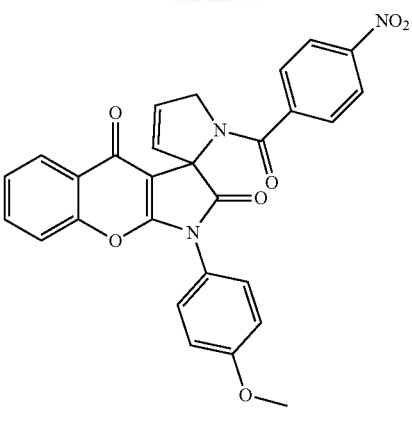

11k 68%

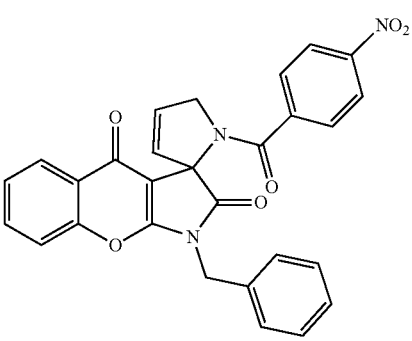

11l, 78%

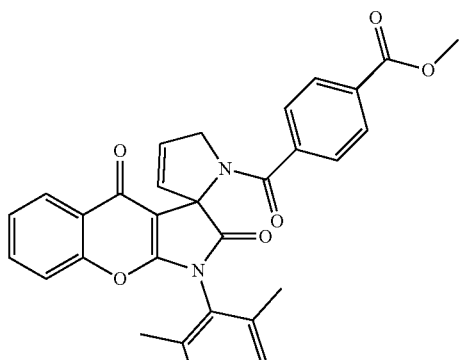

11m, 73%

Only changing solvent form EtOH to DMF, another chromone derivative was obtained. From the final compounds, this reaction show high tolerance of substituents. Acids with electron-donating group and electron-withdrawing group on phenyl ring all afford the corresponding product 11a-m with yield ranging from 59% to 76%. It indicates the reactivity of amide will effect the yield of final products via C—N bond formation. Different kinds of heterocycles in acid part were successfully introduced to this U-4CR. It is noteworthy that the product of Ugi adduct 9 still did not require purification by column chromatography, and crude product having no discernible impact on the overall yield of final products.

1'-(benzo[d][1,3]dioxole-5-carbonyl)-1-(2,6-dimethylphenyl)-1',5'-dihydro-2H-spiro[chromeno[2,3-b]pyrrole-3,2'-pyrrole]-2,4(1H)-dione

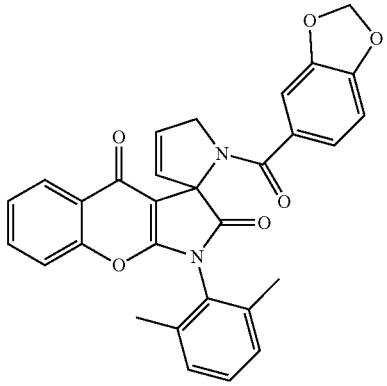 [SMILES: Cc1cccc(C)c1N1C(=O)C2(C=CCN2C(=O)c2ccc3c(c2)OCO3)c2c1oc1ccccc1c2=O]

11a, 71%, $^1$H NMR (400 MHz, CDCl$_3$) δ 8.23 (dd, J=7.9, 1.4 Hz, 1H), 7.61-7.55 (m, 1H), 7.44 (t, J=7.5 Hz, 1H), 7.35 (t, J=7.4 Hz, 2H), 7.27 (s, 1H), 7.22 (d, J=7.5 Hz, 1H), 7.14 (dd, J=8.0, 1.4 Hz, 1H), 7.08 (d, J=1.3 Hz, 1H), 6.81 (d, J=8.0 Hz, 1H), 6.32 (d, J=6.2 Hz, 1H), 5.99 (s, 2H), 5.65 (d, J=6.2 Hz, 1H), 4.86 (d, J=14.7 Hz, 1H), 4.49 (d, J=14.6 Hz, 1H), 2.52 (s, 3H), 2.23 (s, 3H). $^{13}$C NMR (100 MHz, CDCl$_3$) δ 171.92, 170.89, 167.77, 162.03, 154.27, 149.28, 147.56, 138.87, 136.50, 132.63, 131.16, 129.86, 129.24, 128.83, 128.34, 126.09, 125.90, 125.66, 125.12, 122.00, 117.68, 101.44, 56.66, 18.12.

1-(2,6-dimethylphenyl)-1'-(4-nitrobenzoyl)-1',5'-dihydro-2H-spiro[chromeno[2,3-b]pyrrole-3,2'-pyrrole]-2,4(1H)-dione

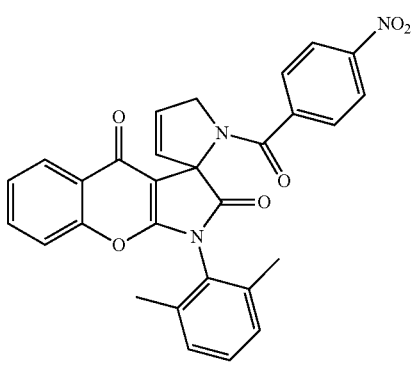 [SMILES: Cc1cccc(C)c1N1C(=O)C2(C=CCN2C(=O)c2ccc([N+](=O)[O-])cc2)c2c1oc1ccccc1c2=O]

11b, 69%, $^1$H NMR (400 MHz, CDCl$_3$) δ 8.28 (d, J=8.6 Hz, 2H), 8.24 (dd, J=7.9, 1.5 Hz, 1H), 7.76 (d, J=8.6 Hz, 2H), 7.64-7.56 (m, 1H), 7.47 (t, J=7.5 Hz, 1H), 7.39-7.33 (m, 2H), 7.29 (s, 1H), 7.24 (d, J=7.5 Hz, 1H), 6.42-6.26 (m, 1H), 5.69 (dt, J=6.0, 2.1 Hz, 1H), 4.85-4.67 (m, 1H), 4.39 (dt, J=14.4, 2.0 Hz, 1H), 2.50 (s, 3H), 2.24 (s, 3H). $^{13}$C NMR (100 MHz, CDCl$_3$) δ 170.90, 166.40, 162.08, 154.32, 148.81, 141.14, 138.66, 136.43, 132.84, 130.67, 130.03, 129.29, 128.86, 128.46, 128.22, 126.27, 125.90, 125.54, 125.23, 123.88, 117.77, 97.88, 74.28, 56.43, 18.02.

1'-benzoyl-1-(2,6-dimethylphenyl)-1',5'-dihydro-2H-spiro[chromeno[2,3-b]pyrrole-3,2'-pyrrole]-2,4(1H)-dione

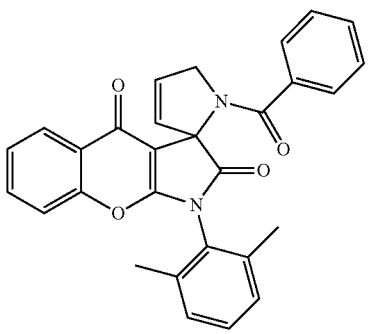 [SMILES: Cc1cccc(C)c1N1C(=O)C2(C=CCN2C(=O)c2ccccc2)c2c1oc1ccccc1c2=O]

11c, 70%, $^1$H NMR (400 MHz, CDCl$_3$) δ 8.25 (dd, J=7.9, 1.5 Hz, 1H), 7.63-7.55 (m, 3H), 7.46 (dd, J=12.6, 5.0 Hz, 2H), 7.41 (d, J=7.5 Hz, 2H), 7.38-7.32 (m, 2H), 7.28 (s, 1H), 7.23 (d, J=7.5 Hz, 1H), 6.31 (d, J=6.2 Hz, 1H), 5.73-5.58 (m, 1H), 4.90-4.76 (m, 1H), 4.53-4.35 (m, 1H), 2.51 (s, 3H), 2.23 (s, 3H). $^{13}$C NMR (100 MHz, CDCl$_3$) δ 171.86, 171.16, 168.94, 162.41, 154.28, 138.83, 136.43, 134.99, 132.84, 131.28, 130.39, 129.95, 129.28, 128.48, 127.05, 126.25, 126.00, 125.43, 124.96, 117.71, 74.19, 56.63, 18.10.

1-(2,6-dimethylphenyl)-1'-(3-iodobenzoyl)-1',5'-dihydro-2H-spiro[chromeno[2,3-b]pyrrole-3,2'-pyrrole]-2,4(1H)-dione

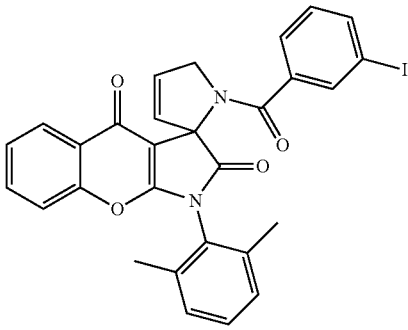 [SMILES: Cc1cccc(C)c1N1C(=O)C2(C=CCN2C(=O)c2cccc(I)c2)c2c1oc1ccccc1c2=O]

11d, 72%, $^1$H NMR (400 MHz, CDCl$_3$) δ 8.37 (d, J=7.7 Hz, 1H), 8.03 (s, 1H), 7.90 (d, J=7.6 Hz, 1H), 7.79-7.62 (m, 2H), 7.59 (d, J=7.1 Hz, 1H), 7.47 (d, J=7.6 Hz, 2H), 7.40 (dd, J=5.4, 2.6 Hz, 2H), 7.23 (s, 1H), 6.44 (s, 1H), 5.80 (s, 1H), 4.91 (d, J=13.9 Hz, 1H), 4.57 (d, J=14.1 Hz, 1H), 2.63 (s, 3H), 2.36 (s, 3H). $^{13}$C NMR (100 MHz, CDCl$_3$) δ 170.84, 166.70, 164.78, 162.01, 159.28, 154.30, 135.71, 135.28, 130.95, 130.13, 129.92, 129.26, 128.74, 128.38, 127.74, 126.17, 125.13, 117.71, 98.10, 94.07, 74.23, 56.56, 18.09.

1'-(2-bromobenzoyl)-1-(2,6-dimethylphenyl)-1',5'-dihydro-2H-spiro[chromeno[2,3-b]pyrrole-3,2'-pyrrole]-2,4(1H)-dione

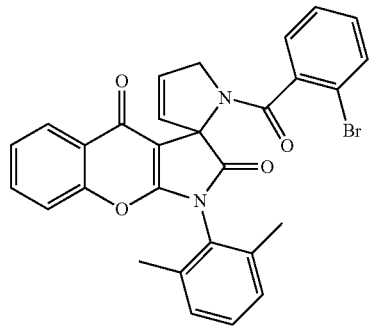 [SMILES: Cc1cccc(C)c1N1C(=O)C2(C=CCN2C(=O)c2ccccc2Br)c2c1oc1ccccc1c2=O]

11e, 67%, ¹H NMR (400 MHz, CDCl₃) δ 8.25 (dd, J=7.9, 1.5 Hz, 1H), 7.58 (d, J=7.9 Hz, 2H), 7.45 (t, J=7.5 Hz, 1H), 7.38-7.31 (m, 4H), 7.23 (dd, J=13.6, 4.6 Hz, 3H), 6.29 (d, J=6.2 Hz, 1H), 5.67 (d, J=6.2 Hz, 1H), 4.53 (d, J=14.6 Hz, 1H), 4.33 (d, J=14.6 Hz, 1H), 2.51 (s, 3H), 2.23 (s, 3H). ¹³C NMR (100 MHz, CDCl₃) δ 171.48, 170.62, 166.41, 162.00, 154.30, 138.86, 137.50, 136.43, 132.95, 132.63, 130.97, 129.88, 129.26, 128.32, 127.96, 126.09, 125.76, 125.10, 118.75, 117.72, 98.03, 73.67, 55.64, 18.20.

1'-(4-chlorobenzoyl)-1-(2,6-dimethylphenyl)-1',5'-dihydro-2H-spiro[chromeno[2,3-b]pyrrole-3,2'-pyrrole]-2,4(1H)-dione

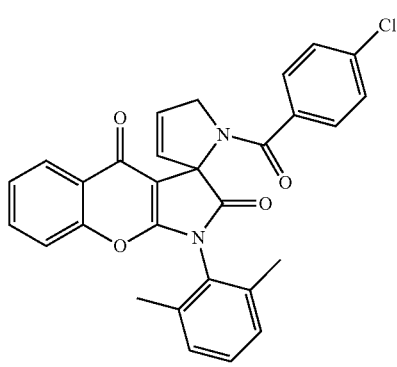 [SMILES: Cc1cccc(C)c1N1C(=O)C2(C=CCN2C(=O)c2ccc(Cl)cc2)c2c1oc1ccccc1c2=O]

11f, 71%, ¹H NMR (400 MHz, CDCl₃) δ 8.22 (dd, J=7.9, 1.5 Hz, 1H), 7.61-7.56 (m, 1H), 7.53 (d, J=8.4 Hz, 2H), 7.44 (t, J=7.5 Hz, 1H), 7.36 (dd, J=15.1, 8.1 Hz, 4H), 7.27 (d, J=2.3 Hz, 1H), 7.22 (d, J=7.5 Hz, 1H), 6.30 (d, J=6.2 Hz, 1H), 5.66 (d, J=6.2 Hz, 1H), 4.79 (d, J=14.6 Hz, 1H), 4.42 (d, J=14.5 Hz, 1H), 2.51 (s, 3H), 2.23 (s, 3H). ¹³C NMR (100 MHz, CDCl₃) δ 171.79, 170.89, 167.47, 162.04, 154.28, 138.76, 136.47, 133.58, 132.74, 131.00, 129.94, 129.26, 128.77, 128.40, 126.17, 125.88, 125.15, 117.72, 98.12, 74.24, 56.55, 18.11.

6-chloro-1-(2,6-dimethylphenyl)-1'-(4-nitrobenzoyl)-1',5'-dihydro-2H-spiro[chromeno[2,3-b]pyrrole-3,2'-pyrrole]-2,4(1H)-dione

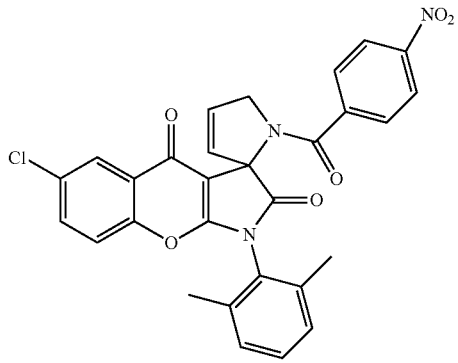 [SMILES: Cc1cccc(C)c1N1C(=O)C2(C=CCN2C(=O)c2ccc([N+](=O)[O-])cc2)c2c1oc1ccc(Cl)cc1c2=O]

11g, 76%, ¹H NMR (400 MHz, CDCl₃) δ 8.26 (d, J=1.9 Hz, 2H), 8.17 (d, J=2.5 Hz, 1H), 7.96 (d, J=8.7 Hz, 2H), 7.74 (d, J=8.6 Hz, 2H), 7.34 (dd, J=12.1, 8.3 Hz, 2H), 7.23 (d, J=7.6 Hz, 1H), 6.32 (d, J=6.2 Hz, 1H), 5.68 (d, J=6.2 Hz, 1H), 4.75 (d, J=14.4 Hz, 1H), 4.39 (d, J=14.4 Hz, 1H), 2.48 (s, 3H), 2.24 (s, 3H). ¹³C NMR (100 MHz, CDCl₃) δ 171.42, 166.49, 164.89, 159.51, 152.61, 148.84, 140.95, 135.27, 132.90, 130.93, 130.16, 129.34, 128.74, 128.32, 127.78, 123.92, 119.35, 97.97, 74.23, 56.44, 18.09.

1'-(5-bromopicolinoyl)-1-(2,6-dimethylphenyl)-1',5'-dihydro-2H-spiro[chromeno[2,3-b]pyrrole-3,2'-pyrrole]-2,4(1H)-dione

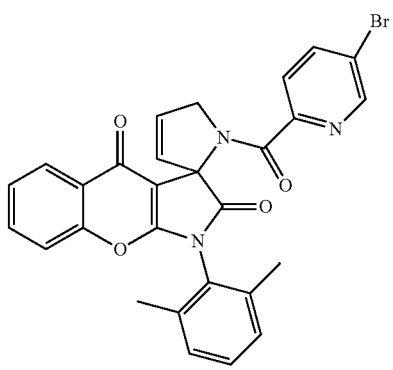 [SMILES: Cc1cccc(C)c1N1C(=O)C2(C=CCN2C(=O)c2ccc(Br)cn2)c2c1oc1ccccc1c2=O]

11 h, 59%, ¹H NMR (400 MHz, CDCl₃) δ 8.81-8.72 (m, 2H), 8.24 (d, J=7.8 Hz, 1H), 8.06 (s, 1H), 7.60 (t, J=7.7 Hz, 1H), 7.46 (t, J=7.5 Hz, 1H), 7.39-7.33 (m, 2H), 7.29 (s, 1H), 7.23 (d, J=7.5 Hz, 1H), 6.33 (d, J=6.2 Hz, 1H), 5.69 (d, J=6.2 Hz, 1H), 4.84 (d, J=14.3 Hz, 1H), 4.50 (d, J=14.2 Hz, 1H), 2.50 (s, 3H), 2.24 (s, 3H). ¹³C NMR (100 MHz, CDCl₃) δ 171.44, 170.80, 164.35, 162.04, 154.31, 152.49, 146.04, 138.66, 137.42, 136.43, 132.81, 132.35, 130.62, 130.00, 129.29, 128.44, 126.25, 125.95, 125.54, 125.26, 117.74, 97.82, 74.43, 56.49, 18.00.

1-(2,6-dimethylphenyl)-1'-(6-methylnicotinoyl)-1',5'-dihydro-2H-spiro[chromeno[2,3-b]pyrrole-3,2'-pyrrole]-2,4(1H)-dione

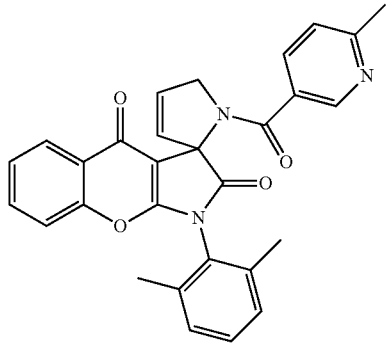 [SMILES: Cc1ccc(C(=O)N2CC=CC23C(=O)N(c2c(C)cccc2C)c2oc4ccccc4c(=O)c23)cn1]

11i, 74%, ¹H NMR (400 MHz, CDCl₃) δ 8.75 (s, 1H), 8.23 (d, J=7.9 Hz, 1H), 7.82 (dd, J=8.0, 2.0 Hz, 1H), 7.59 (t, J=7.8 Hz, 1H), 7.45 (t, J=7.5 Hz, 1H), 7.35 (t, J=7.3 Hz, 2H), 7.27 (t, J=3.5 Hz, 1H), 7.24-7.17 (m, 2H), 6.32 (d, J=6.2 Hz, 1H), 5.68 (d, J=6.2 Hz, 1H), 4.85 (d, J=14.4 Hz, 1H), 4.50 (d, J=14.3 Hz, 1H), 2.59 (s, 3H), 2.52 (s, 3H), 2.24 (s, 3H). ¹³C NMR (100 MHz, CDCl₃) δ 171.71, 170.83, 166.28, 162.54, 162.00, 160.64, 154.29, 147.60, 138.74, 136.46, 135.39, 132.72, 130.91, 129.93, 129.26, 128.95, 128.40, 126.17, 125.91, 125.60, 125.20, 122.78, 117.71, 98.07, 74.37, 56.50, 24.52, 18.11.

1-(2,6-dimethylphenyl)-1'-(furan-2-carbonyl)-1',5'-dihydro-2H-spiro[chromeno[2,3-b]pyrrole-3,2'-pyrrole]-2,4(1H)-dione

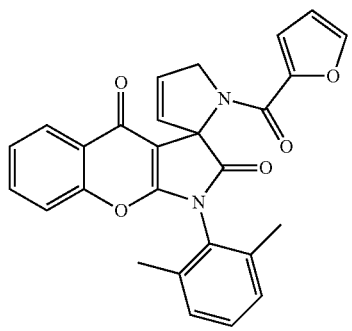 [SMILES: Cc1cccc(C)c1N1C(=O)C2(C=CCN2C(=O)c2ccco2)c2c1oc1ccccc1c2=O]

11j, 72%, ¹H NMR (400 MHz, CDCl₃) δ 8.18 (dd, J=7.9, 1.3 Hz, 1H), 7.58-7.53 (m, 2H), 7.41 (dd, J=10.0, 5.0 Hz, 1H), 7.32 (dd, J=7.9, 4.0 Hz, 2H), 7.22 (t, J=8.8 Hz, 2H), 7.13 (d, J=3.5 Hz, 1H), 6.49 (dd, J=3.4, 1.6 Hz, 1H), 6.43 (d, J=6.2 Hz, 1H), 5.66 (d, J=6.2 Hz, 1H), 5.16 (d, J=15.1 Hz, 1H), 5.06 (d, J=15.1 Hz, 1H), 2.53 (s, 3H), 2.23 (s, 3H). ¹³C NMR (100 MHz, CDCl₃) δ 171.93, 170.68, 162.57, 161.86, 156.39, 154.27, 147.23, 144.89, 138.86, 136.42, 132.56, 131.37, 129.84, 129.19, 128.34, 126.05, 124.32, 117.60, 111.71, 98.27, 75.11, 55.44, 18.11.

1-(4-methoxyphenyl)-1'-(4-nitrobenzoyl)-1',5'-dihydro-2H-spiro[chromeno[2,3-b]pyrrole-3,2'-pyrrole]-2,4(1H)-dione

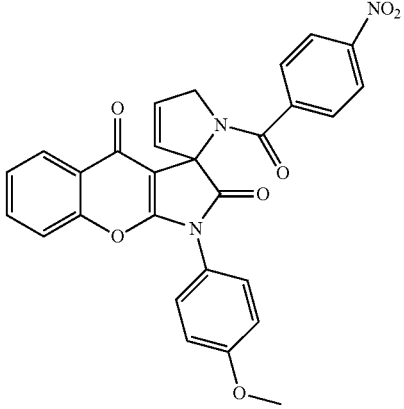 [SMILES: COc1ccc(N2C(=O)C3(C=CCN3C(=O)c3ccc([N+](=O)[O-])cc3)c3c2oc2ccccc2c3=O)cc1]

11k, 68%, ¹H NMR (400 MHz, CDCl₃) δ 8.28 (d, J=8.7 Hz, 2H), 8.22 (dd, J=7.9, 1.4 Hz, 1H), 7.75 (d, J=8.6 Hz, 2H), 7.62 (dd, J=11.4, 4.4 Hz, 1H), 7.50 (t, J=6.2 Hz, 2H), 7.45 (d, J=7.5 Hz, 1H), 7.39 (d, J=8.4 Hz, 1H), 7.08 (d, J=8.9 Hz, 2H), 6.31 (d, J=6.2 Hz, 1H), 5.75 (d, J=6.3 Hz, 1H), 4.78 (d, J=14.3 Hz, 1H), 4.38 (d, J=14.3 Hz, 1H), 3.90 (s, 3H). ¹³C NMR (100 MHz, CDCl₃) δ 171.16, 166.49, 162.73, 160.16, 154.19, 148.88, 140.90, 132.90, 130.78, 128.40, 126.23, 125.81, 124.97, 123.85, 117.80, 114.90, 114.38, 56.39, 55.61.

1-benzyl-1'-(4-nitrobenzoyl)-1',5'-dihydro-2H-spiro[chromeno[2,3-b]pyrrole-3,2'-pyrrole]-2,4(1H)-dione

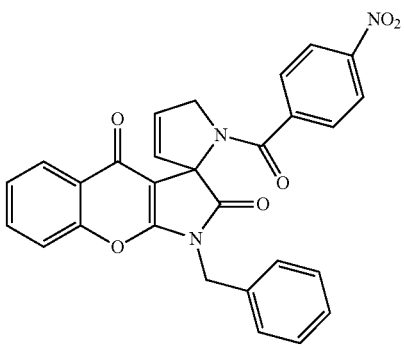 [SMILES: O=C(c1ccc([N+](=O)[O-])cc1)N1CC=CC12C(=O)N(Cc1ccccc1)c1oc3ccccc3c(=O)c12]

11l, 78%, ¹H NMR (400 MHz, CDCl₃) δ 8.27 (d, J=8.6 Hz, 2H), 8.19 (d, J=7.7 Hz, 1H), 7.74 (d, J=8.6 Hz, 2H), 7.63 (dd, J=11.3, 4.1 Hz, 1H), 7.52 (d, J=7.4 Hz, 2H), 7.47-7.37 (m, 4H), 7.34 (d, J=7.4 Hz, 1H), 6.27 (d, J=6.2 Hz, 1H), 5.60 (dd, J=3.9, 2.3 Hz, 1H), 5.14-4.98 (m, 2H), 4.75 (d, J=14.3 Hz, 1H), 4.36 (d, J=14.3 Hz, 1H). ¹³C NMR (100 MHz, CDCl₃) δ 172.86, 170.59, 166.29, 162.75, 154.15, 148.83, 140.98, 135.00, 132.78, 130.51, 128.97, 128.30, 127.95, 126.24, 125.90, 125.05, 123.82, 117.59, 97.57, 74.38, 56.40, 43.93.

Methyl 4-(1-(2,6-dimethylphenyl)-2,4-dioxo-1,1',4,5'-tetrahydro-2H spiro[chromeno[2,3-b]pyrrole-3,2'-pyrrole]-1'-carbonyl)benzoate

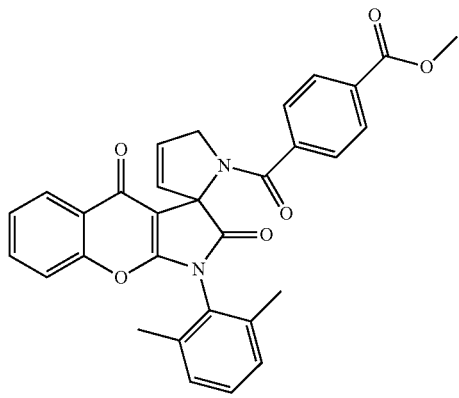 [SMILES: COC(=O)c1ccc(C(=O)N2CC=CC23C(=O)N(c2c(C)cccc2C)c2oc4ccccc4c(=O)c23)cc1]

11m, 73%, $^1$H NMR (400 MHz, CDCl3) δ 8.22 (dd, J=7.9, 1.4 Hz, 1H), 8.07 (dd, J=14.4, 5.6 Hz, 2H), 7.66-7.59 (m, 2H), 7.59-7.52 (m, 1H), 7.43 (t, J=7.5 Hz, 1H), 7.33 (dd, J=8.0, 5.0 Hz, 2H), 7.24 (t, J=3.5 Hz, 1H), 7.20 (d, J=7.5 Hz, 1H), 6.28 (d, J=6.2 Hz, 1H), 5.65 (d, J=6.2 Hz, 1H), 4.75 (d, J=14.6 Hz, 1H), 4.37 (d, J=14.5 Hz, 1H), 2.49 (s, 3H), 2.21 (s, 3H). $^{13}$C NMR (100 MHz, CDCl3) δ 171.68, 170.88, 167.60, 166.30, 162.00, 154.23, 139.29, 138.70, 136.41, 132.73, 131.61, 130.95, 129.91, 129.48, 128.87, 128.36, 127.04, 126.16, 125.86, 125.04, 117.69, 98.04, 74.12, 56.42, 52.33, 18.09, 18.08.

Example 1: Bioactivity Assays

Figure 1B:
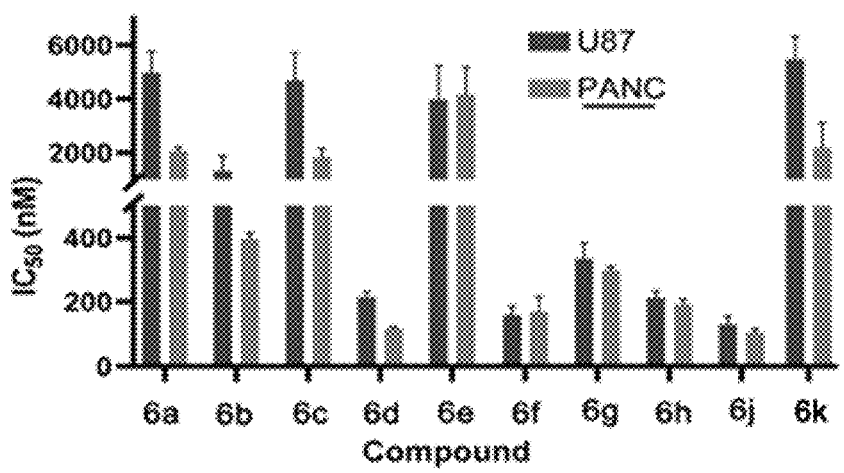

To evaluate potentials for developing a drug leading from the synthesized compounds, the MTT assay was used to measure cancer cell viability upon the drug treatment. Two cancer cell lines (PANC and U87) were selected, which are some of the representing solid tumor cell lines in the National Cancer Institute's 60 human tumor cell lines panel (see FIG. 1A). It is indicated that the compounds of Formula I according to the present application exhibited excellent anticancer activities. For example, Compound 6j exhibited excellent anticancer activities in the human pancreatic cell lines PANC with IC$_{50}$=92 nM (see FIG. 1B).

In conclusion, the C—C/C—N formation on a chromone core in one-pot post-Ugi reaction was succeeded in the present application. Under the mild reaction condition and simple operation procedure, two series of diastereoselective chromone-spiro-γ-lactams were synthesized in good yield. The synthesized compounds were screened and the compounds of Formula I according to the present application such as compound 6j showed excellent anticancer activities.

The preceding description of the disclosed embodiments is provided to enable any person skilled in the art to make or use the present application. Various modifications to these embodiments will be readily apparent to those skilled in the art, and the generic principles defined herein may be applied to other embodiments without departing from the scope of the invention. Thus, the present application is not intended to be limited to the embodiments shown herein but is to be accorded the widest scope consistent with the principles and novel features disclosed herein. Further, any reference to claim elements in the singular, for example, using the articles "a," "an," or "the," is not to be construed as limiting the element to the singular.

What is claimed is:
1. A compound of Formula I or a pharmaceutically acceptable salt thereof,

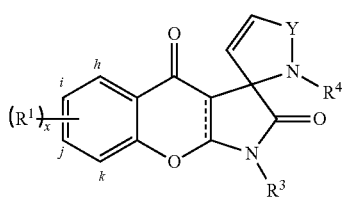

Formula I each $R^1$ is independently selected from the group consisting of H and halo, and $R^1$ is on at least one position selected from h-, i-, j- and k-positions;
x is a integer selected from 1, 2, 3 or 4;
$R^3$ is selected from the group consisting of optionally substituted alkyl and optionally substituted aryl;
═════ represents a single or double bond;
Y is selected from the group consisting of C═O and CH$_2$;
$R^4$ is selected from the group consisting of $R^2$ and —C(═O)—$R^2$;
with the proviso that when Y is C═O, $R^4$ is $R^2$; and when Y is CH$_2$, $R^4$ is —C(═O)—$R^2$;
and with the further proviso that when ═════ represents a double bond, Y is CH$_2$, and $R^4$ is —C(═O)—$R^2$;
$R^2$ is selected from the group consisting of optionally substituted aryl and optionally substituted heteroaryl.
2. The compound according to claim 1, wherein
$R^1$ is on at least one position selected from i- and j-positions;
optionally, each $R^1$ is independently selected from the group consisting of H, Cl and Br.
3. The compound according to claim 1, wherein,
$R^3$ is selected from the group consisting of alkyl and aryl, each of which is independently optionally substituted with one or more substituents selected from alkyl, alkoxy, and aryl;
optionally, $R^3$ is selected from the group consisting of $C_{1-6}$ alkyl and $C_{6-20}$ aryl, each of which is independently optionally substituted with one or more substituents selected from $C_{1-6}$ alkyl, $C_{1-6}$ alkoxy, and $C_{6-20}$ aryl;
optionally, $R^3$ is selected from the group consisting of $C_{1-6}$ alkyl and $C_{6-15}$ aryl, each of which is independently optionally substituted with one or more substituents selected from $C_{1-6}$ alkyl, $C_{1-6}$ alkoxy, and $C_{6-15}$ aryl;
optionally, $R^3$ is selected from the group consisting of $C_{1-6}$ alkyl and $C_{6-12}$ aryl, each of which is independently optionally substituted with one or more substituents selected from $C_{1-6}$ alkyl, $C_{1-6}$ alkoxy, and $C_{6-12}$ aryl;
optionally, $R^3$ is selected from the group consisting of: alkyl optionally substituted with aryl; and aryl optionally substituted with one or more substituents selected from alkyl and alkoxy;
optionally, said aryl in the definition of $R^3$ is selected from the group consisting of phenyl and naphthyl;

optionally, R³ is selected from the group consisting of benzyl, 2,6-dimethylphenyl, 4-methoxyphenyl and naphthyl.

4. The compound according to claim 1, wherein,

R² is selected from the group consisting of aryl and heteroaryl, each of which is independently optionally substituted with one or more substituents selected from: halo; alkoxy; nitro; alkoxycarbonyl; and alkyl optionally substituted with one or more substituents selected from halo and NR'R", wherein R' and R" are each independently selected from the group consisting of H and Boc;

optionally, R² is selected from the group consisting of $C_{6-20}$ aryl and 5- to 20-membered heteroaryl, each of which is independently optionally substituted with one or more substituents selected from: halo; $C_{1-6}$ alkoxy; nitro; $C_{1-6}$ alkoxycarbonyl; and $C_{1-6}$ alkyl optionally substituted with one or more substituents selected from halo and NR'R", wherein R' and R" are each independently selected from the group consisting of H and Boc;

optionally, R² is selected from the group consisting of $C_{6-15}$ aryl and 5- to 15-membered heteroaryl, each of which is independently optionally substituted with one or more substituents selected from: halo; $C_{1-6}$ alkoxy; nitro; $C_{1-6}$ alkoxycarbonyl; and $C_{1-6}$ alkyl optionally substituted with one or more substituents selected from halo and NR'R", wherein R' and R" are each independently selected from the group consisting of H and Boc;

optionally, R² is selected from the group consisting of $C_{6-12}$ aryl and 5- to 12-membered heteroaryl, each of which is independently optionally substituted with one or more substituents selected from: halo; $C_{1-6}$ alkoxy; nitro; $C_{1-6}$ alkoxycarbonyl; and $C_{1-6}$ alkyl optionally substituted with one or more substituents selected from halo and NR'R", wherein R' and R" are each independently selected from the group consisting of H and Boc;

optionally, said aryl in the definition of R² is selected from the group consisting of phenyl and 1,3-benzodioxolyl;

optionally, said heteroaryl in the definition of R² is selected from the group consisting of furyl, thienyl and pyridyl;

optionally, R² is selected from the group consisting of 1,3-benzodioxolyl; furyl; thienyl; pyridyl optionally substituted with halo or $C_{1-4}$ alkyl; and phenyl optionally substituted with one or more substituents selected from the group consisting of halo, $C_{1-6}$ alkoxy, nitro, $C_{1-6}$ alkoxycarbonyl, and $C_{1-6}$ alkyl optionally substituted with one or more substituents selected from halo and NR'R", wherein R' and R" are each independently selected from the group consisting of H and Boc;

optionally, R² is selected from the group consisting of 1,3-benzodioxolyl; furyl; thienyl; pyridyl optionally substituted with Br or methyl; and phenyl optionally substituted with F, Cl, Br, I, methoxy, nitro, methoxycarbonyl, $CF_3$, —$CH_2NH_2$ or —$CH_2NHBoc$.

5. The compound according to claim 1, said Formula I is Formula Ia:

6. The compound according to claim 5, in said Formula Ia, R³ is optionally substituted aryl;

optionally, R³ is aryl optionally substituted with one or more substituents selected from alkyl;

optionally, R³ is $C_{6-20}$ aryl optionally substituted with one or more substituents selected from $C_{1-6}$ alkyl;

optionally, R³ is $C_{6-15}$ aryl optionally substituted with one or more substituents selected from $C_{1-6}$ alkyl;

optionally, R³ is $C_{6-12}$ aryl optionally substituted with one or more substituents selected from $C_{1-6}$ alkyl;

optionally, R³ is selected from the group consisting of phenyl and naphthyl, each of which is optionally substituted with one or more substituents selected from $C_{1-4}$ alkyl;

optionally, R³ is selected from the group consisting of phenyl and naphthyl, each of which is optionally substituted with one or more methyl groups;

optionally, R³ is selected from the group consisting of 2,6-dimethylphenyl and naphthyl.

7. The compound according to claim 5, in said Formula Ia, R² is optionally substituted aryl;

optionally, R² is aryl optionally substituted with one or more substituents selected from: halo; alkoxy; and alkyl optionally substituted with one or more substituents selected from halo and NR'R", wherein R' and R" are each independently selected from the group consisting of H and Boc;

optionally, R² is $C_{6-20}$ aryl optionally substituted with one or more substituents selected from: halo; $C_{1-6}$ alkoxy; and $C_{1-6}$ alkyl optionally substituted with one or more substituents selected from halo and NR'R", wherein R' and R" are each independently selected from the group consisting of H and Boc;

optionally, R² is $C_{6-15}$ aryl optionally substituted with one or more substituents selected from: halo; $C_{1-6}$ alkoxy; and $C_{1-6}$ alkyl optionally substituted with one or more substituents selected from halo and NR'R", wherein R' and R" are each independently selected from the group consisting of H and Boc;

optionally, R² is $C_{6-12}$ aryl optionally substituted with one or more substituents selected from: halo; $C_{1-6}$ alkoxy; and $C_{1-6}$ alkyl optionally substituted with one or more substituents selected from halo and NR'R", wherein R' and R" are each independently selected from the group consisting of H and Boc;

optionally, R² is phenyl optionally substituted with one or more substituents selected from: F; Cl; Br; $C_{1-4}$ alkoxy; and $C_{1-4}$ alkyl optionally substituted with one or more substituents selected from F and NR'R", wherein R' and R" are each independently selected from the group consisting of H and Boc;

optionally, R² is phenyl optionally substituted with one or more substituents selected from the group consisting of F, Cl, Br, methoxy, —$CF_3$, —$CH_2NH_2$ or —$CH_2NHBoc$.

8. The compound according to claim 1, said Formula I is Formula Ib or Ic:

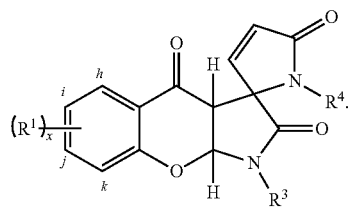

Formula Ia

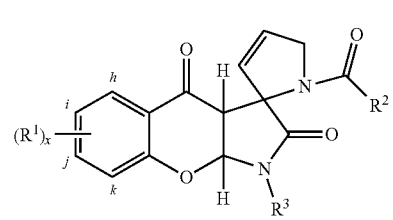

Formula Ib

-continued

Formula Ic

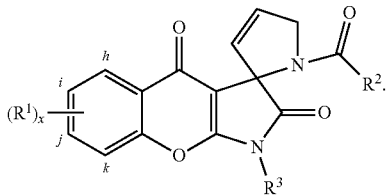

9. The compound according to claim 8, in said Formula Ib, $R^3$ is optionally substituted aryl;

optionally, $R^3$ is aryl optionally substituted with one or more substituents selected from alkyl;

optionally, $R^3$ is $C_{6-20}$ aryl optionally substituted with one or more substituents selected from $C_{1-6}$ alkyl;

optionally, $R^3$ is $C_{6-15}$ aryl optionally substituted with one or more substituents selected from $C_{1-6}$ alkyl;

optionally, $R^3$ is $C_{6-12}$ aryl optionally substituted with one or more substituents selected from $C_{1-6}$ alkyl;

optionally, $R^3$ is selected from the group consisting of phenyl and naphthyl, each of which is optionally substituted with one or more substituents selected from $C_{1-4}$ alkyl;

optionally, $R^3$ is selected from the group consisting of phenyl and naphthyl, each of which is optionally substituted with one or more methyl groups;

optionally, $R^3$ is selected from the group consisting of 2,6-dimethylphenyl and naphthyl.

10. The compound according to claim 8, in said Formula Ib, $R^2$ is selected from the group consisting of aryl and heteroaryl, each of which is independently optionally substituted with one or more substituents selected from the group consisting of halo and nitro;

optionally, $R^2$ is selected from the group consisting of $C_{6-20}$ aryl and 5- to 20-membered heteroaryl, each of which is independently optionally substituted with one or more substituents selected from the group consisting of halo and nitro;

optionally, $R^2$ is selected from the group consisting of $C_{6-15}$ aryl and 5- to 15-membered heteroaryl, each of which is independently optionally substituted with one or more substituents selected from the group consisting of halo and nitro;

optionally, $R^2$ is selected from the group consisting of $C_{6-12}$ aryl and 5- to 12-membered heteroaryl, each of which is independently optionally substituted with one or more substituents selected from the group consisting of halo and nitro;

optionally, said aryl in the definition of $R^2$ is selected from the group consisting of phenyl and 1,3-benzodioxolyl;

optionally, said heteroaryl in the definition of $R^2$ is selected from the group consisting of furyl, thienyl and pyridyl;

optionally, $R^2$ is selected from the group consisting of 1,3-benzodioxolyl; furyl; thienyl; and phenyl optionally substituted with one or more substituents selected from the group consisting of halo and nitro;

optionally, $R^2$ is selected from the group consisting of 1,3-benzodioxolyl, furyl, thienyl, 4-nitrophenyl, 2-nitrophenyl, and 2-bromophenyl.

11. The compound according to claim 8, in said Formula Ic, $R^3$ is selected from the group consisting of alkyl and aryl, each of which is independently optionally substituted with one or more substituents selected from alkyl, alkoxy, and aryl;

optionally, $R^3$ is selected from the group consisting of $C_{1-6}$ alkyl and $C_{6-20}$ aryl, each of which is independently optionally substituted with one or more substituents selected from $C_{1-6}$ alkyl, $C_{1-6}$ alkoxy, and $C_6$-20 aryl;

optionally, $R^3$ is selected from the group consisting of $C_{1-6}$ alkyl and $C_{6-15}$ aryl, each of which is independently optionally substituted with one or more substituents selected from $C_{1-6}$ alkyl, $C_{1-6}$ alkoxy, and $C_{6-15}$ aryl;

optionally, $R^3$ is selected from the group consisting of $C_{1-6}$ alkyl and $C_{6-12}$ aryl, each of which is independently optionally substituted with one or more substituents selected from $C_{1-6}$ alkyl, $C_{1-6}$ alkoxy, and $C_{6-12}$ aryl;

optionally, $R^3$ is selected from the group consisting of: alkyl optionally substituted with aryl; and aryl optionally substituted with one or more substituents selected from alkyl and alkoxy;

optionally, $R^3$ is selected from the group consisting of: $C_{1-4}$ alkyl optionally substituted with $C_{6-12}$ aryl; and $C_{6-12}$ aryl optionally substituted with one or more substituents selected from $C_{1-4}$ alkyl and $C_{1-4}$ alkoxy;

optionally, said aryl in the definition of $R^3$ is selected from the group consisting of phenyl and naphthyl;

optionally, said aryl in the definition of $R^3$ is phenyl;

optionally, $R^3$ is selected from the group consisting of benzyl, 2,6-dimethylphenyl, and 4-methoxylphenyl.

12. The compound according to claim 8, in said Formula Ic, $R^2$ is selected from the group consisting of aryl and heteroaryl, each of which is independently optionally substituted with one or more substituents selected from the group consisting of halo, nitro, alkoxycarbonyl, and alkyl;

optionally, $R^2$ is selected from the group consisting of $C_{6-20}$ aryl and 5- to 20-membered heteroaryl, each of which is independently optionally substituted with one or more substituents selected from the group consisting of halo, nitro, $C_{1-6}$ alkoxycarbonyl, and $C_{1-6}$ alkyl;

optionally, $R^2$ is selected from the group consisting of $C_{6-15}$ aryl and 5- to 15-membered heteroaryl, each of which is independently optionally substituted with one or more substituents selected from the group consisting of halo, nitro, $C_{1-6}$ alkoxycarbonyl, and $C_{1-6}$ alkyl;

optionally, $R^2$ is selected from the group consisting of $C_{6-12}$ aryl and 5- to 12-membered heteroaryl, each of which is independently optionally substituted with one or more substituents selected from the group consisting of halo, nitro, $C_{1-6}$ alkoxycarbonyl, and $C_{1-6}$ alkyl;

optionally, said aryl in the definition of $R^2$ is selected from the group consisting of phenyl and 1,3-benzodioxolyl;

optionally, said heteroaryl in the definition of $R^2$ is selected from the group consisting of furyl, thienyl and pyridyl;

optionally, $R^2$ is selected from the group consisting of 1,3-benzodioxolyl; furyl; pyridyl optionally substituted with halo or $C_{1-4}$ alkyl; and phenyl optionally substituted with one or more substituents selected from the group consisting of halo, nitro, and $C_{1-4}$ alkoxycarbonyl;

optionally, $R^2$ is selected from the group consisting of 1,3-benzodioxolyl, furyl, 4-bromopyridyl, 4-methylpyridyl, 4-nitrophenyl, 4-chlorophenyl, 2-bromophenyl, 3-iodophenyl, 4-methoxylcarbonylphenyl.
13. A compound selected from the following structures:
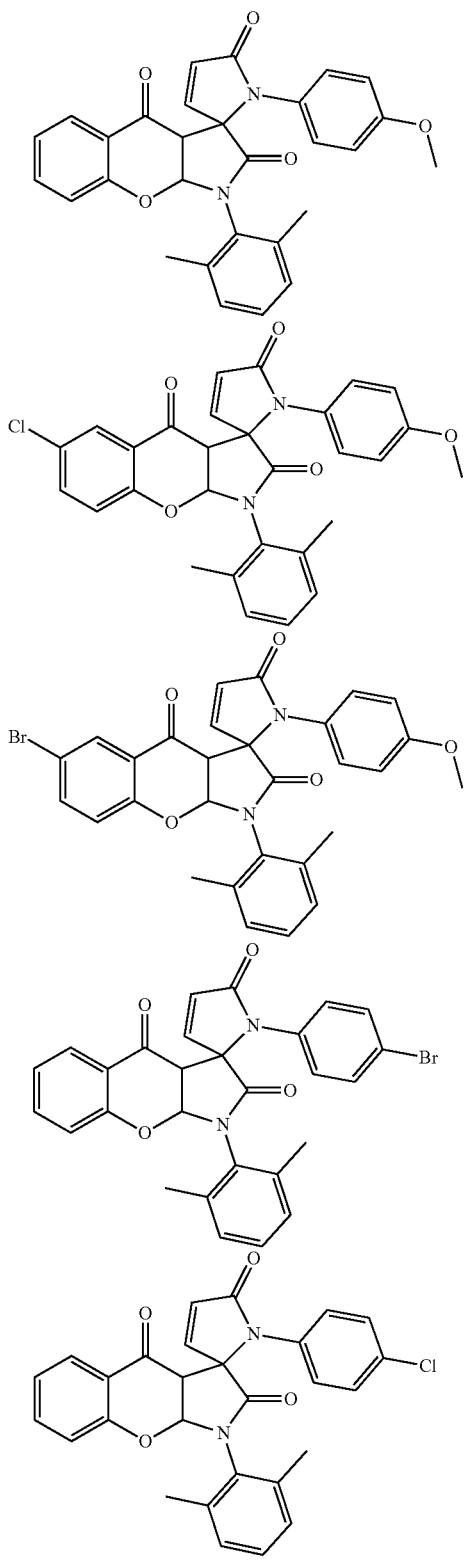
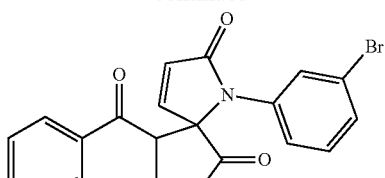
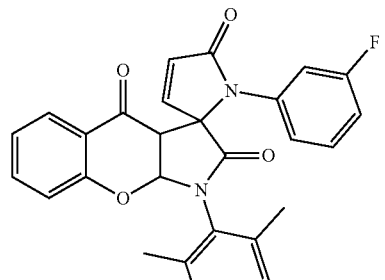
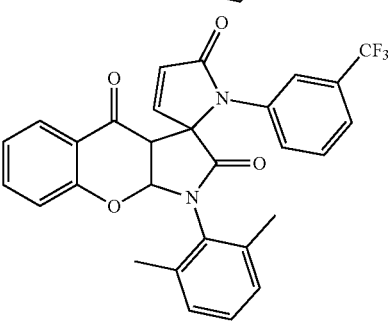
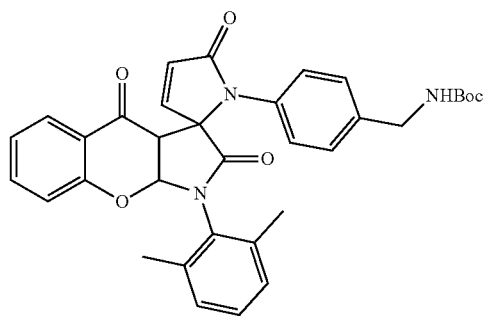
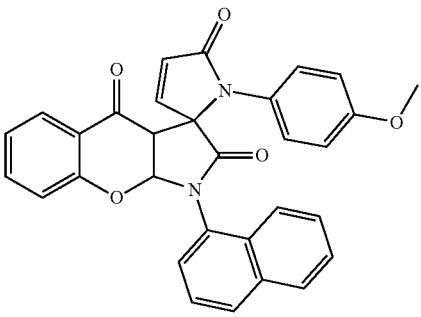

-continued
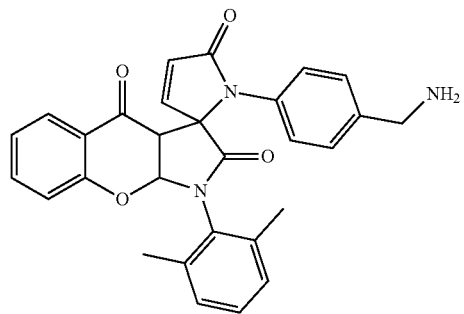
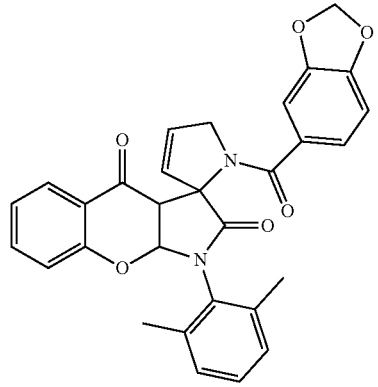
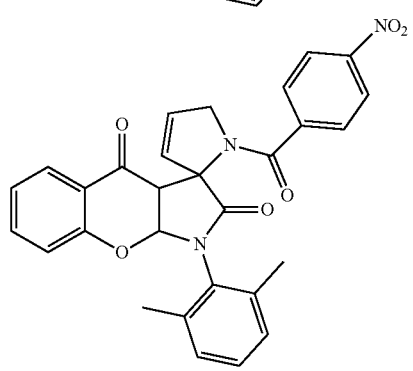
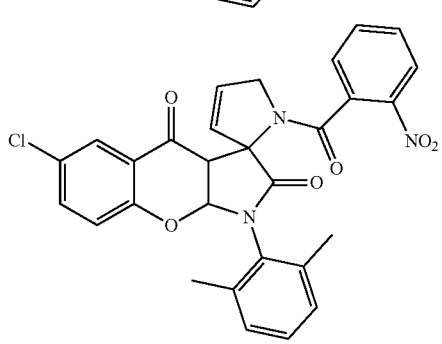
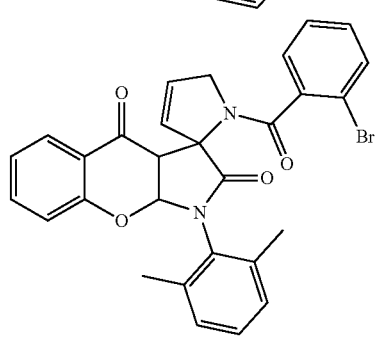
-continued
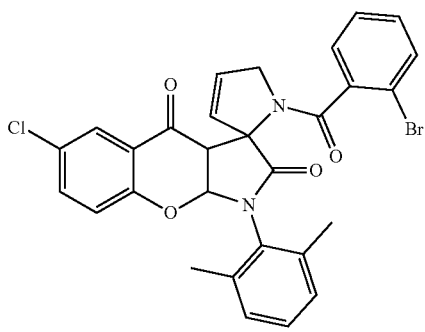
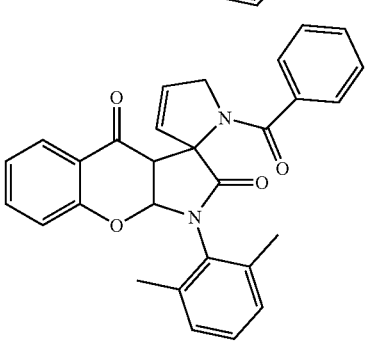
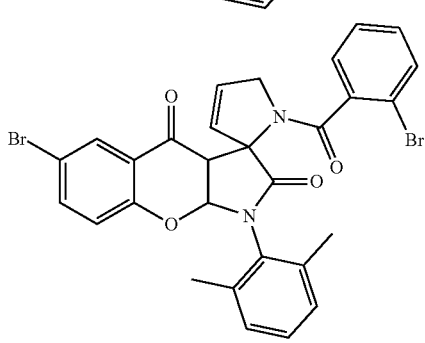
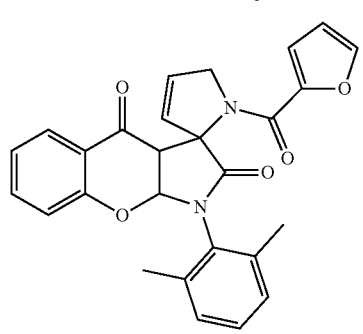
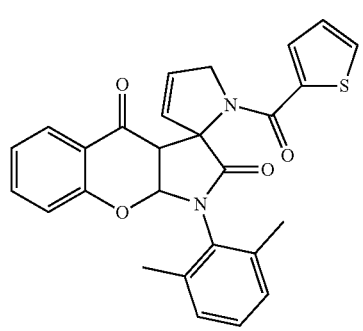

-continued
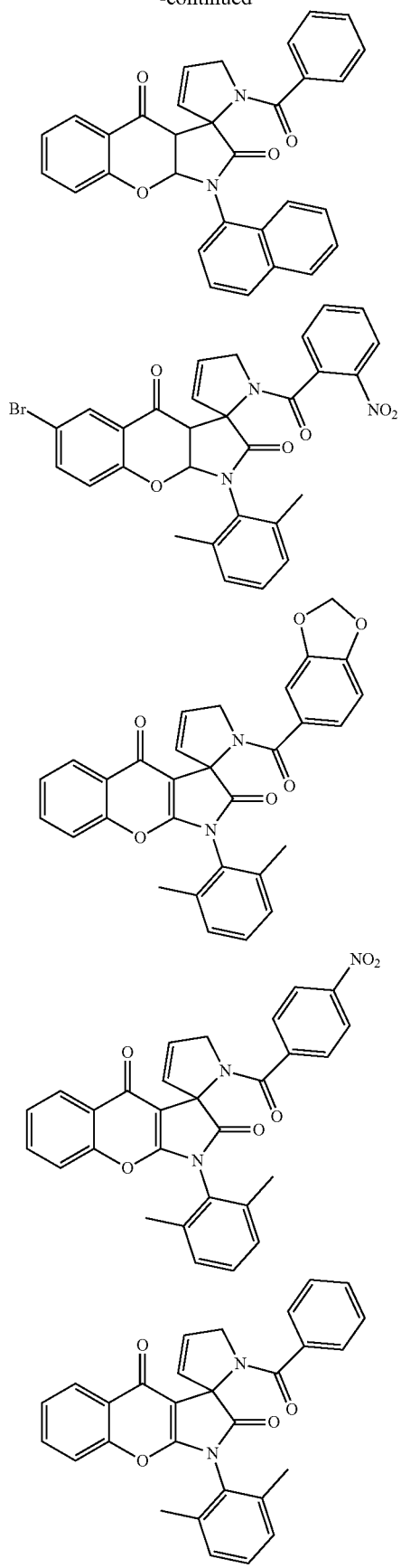
-continued
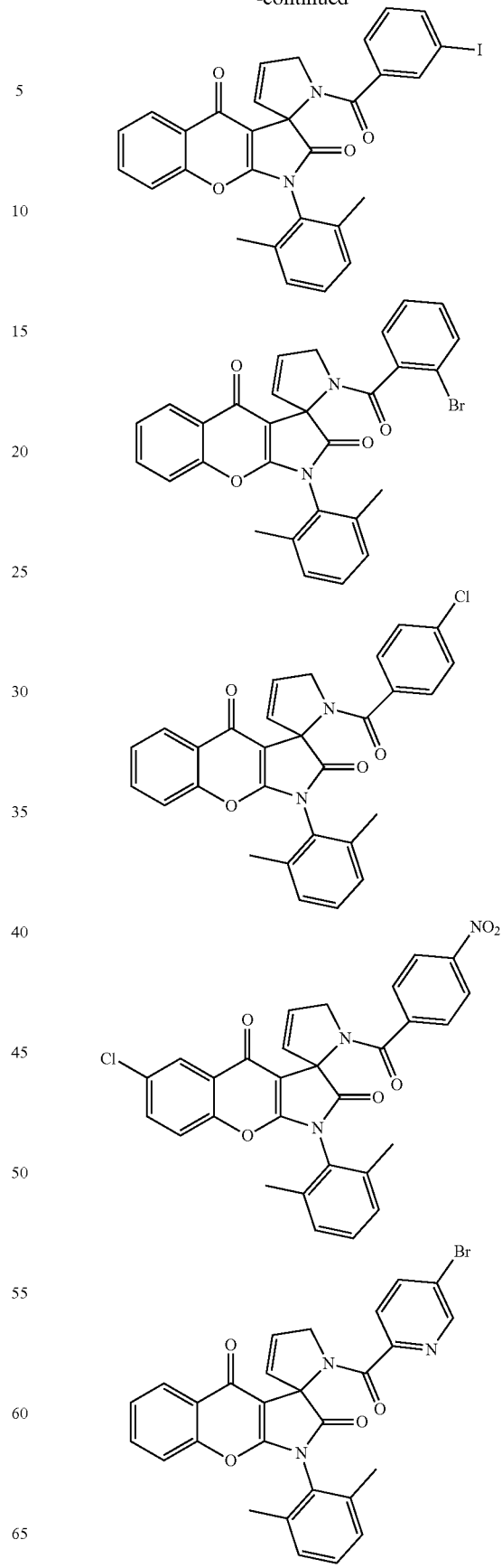

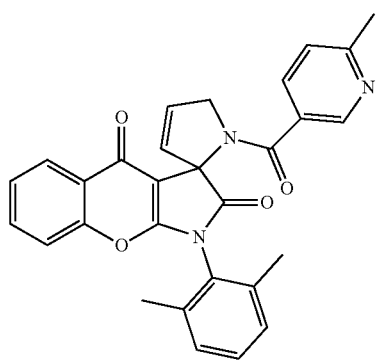
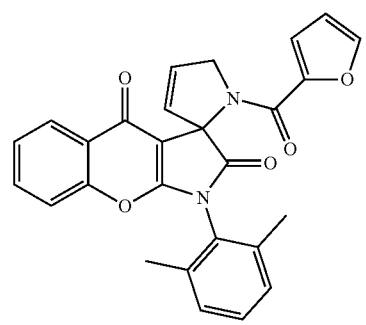
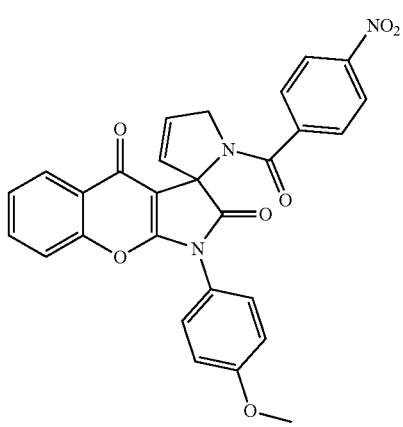
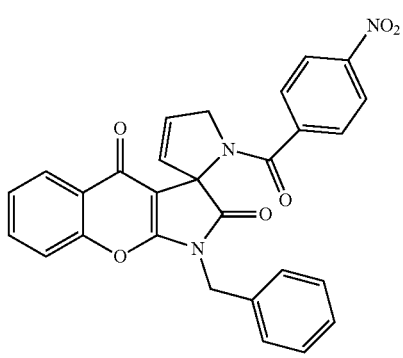
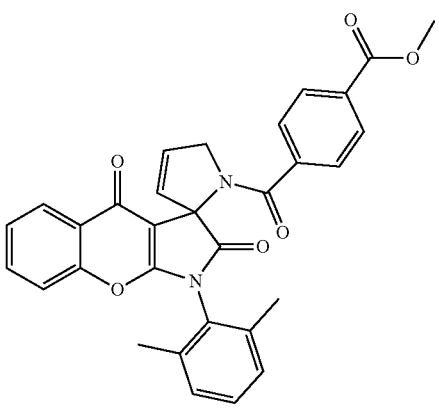
14. A method for preparing a compound of Formula Ia or a pharmaceutically acceptable salt thereof according to claim 6, comprising Step 1 and Step 2 below:
Step 1: performing a Ugi four-component reaction of Compounds 1, 2, 3 and 4 to obtain Compound 5;
Step 2: reacting Compound 5 to obtain the compound of Formula Ia;
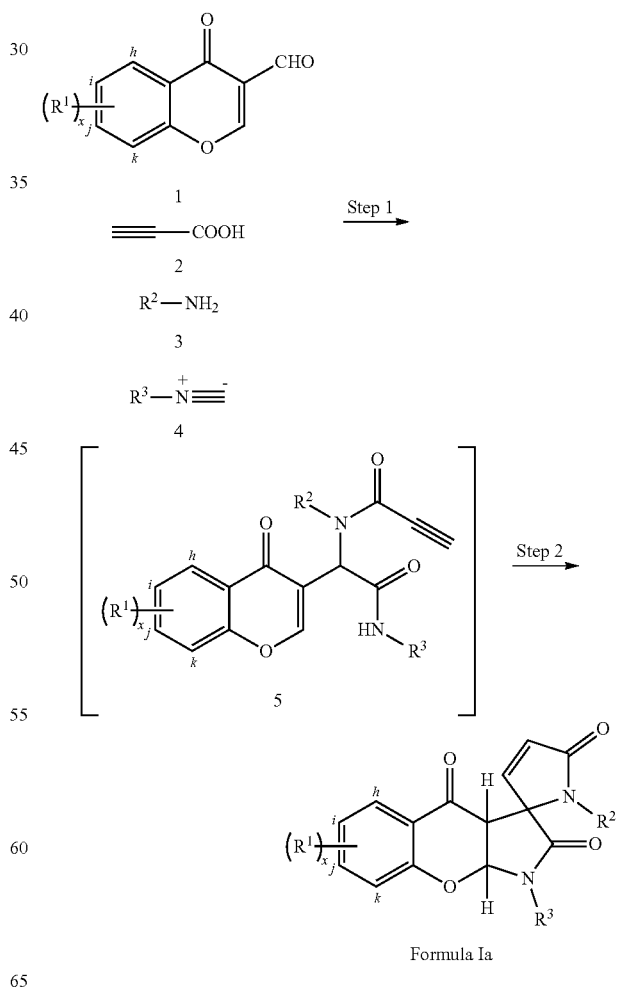
wherein $R^1$, x, $R^2$, and $R^3$ are as defined in claim 6.

15. The method according to claim 14, wherein,

Step 2 is performed in the present of a base and/or a solvent;

optionally, the base in Step 2 is selected from the group consisting of alkali metal carbonate salts, alkali metal acetate salts, and a combination thereof;

optionally, the base in Step 2 is selected from the group consisting of $K_2CO_3$, KOAc, $Cs_2CO_3$, and a combination thereof;

optionally, the base in Step 2 is $Cs_2CO_3$;

optionally, the solvent in Step 2 is selected from the group consisting of MeCN, DMF, and a combination thereof;

optionally, the solvent in Step 2 is MeCN;

optionally, the reaction time of Step 2 is 1-10 h, 1-5 h or 3 h;

optionally, Step 1 is performed in the present of a solvent;

optionally, the solvent in Step 1 is 2,2,2-trifluoroethanol (TFE);

optionally, Step 1 is performed at room temperature.

16. A method for preparing a compound of Formula Ib or a pharmaceutically acceptable salt thereof according to claim 9, comprising Step 1 and Step 2 below:

Step 1: performing a Ugi four-component reaction of Compounds 1, 4, 7 and 8 to obtain Compound 9;

Step 2: reacting Compound 9 to obtain the compound of Formula Ib;

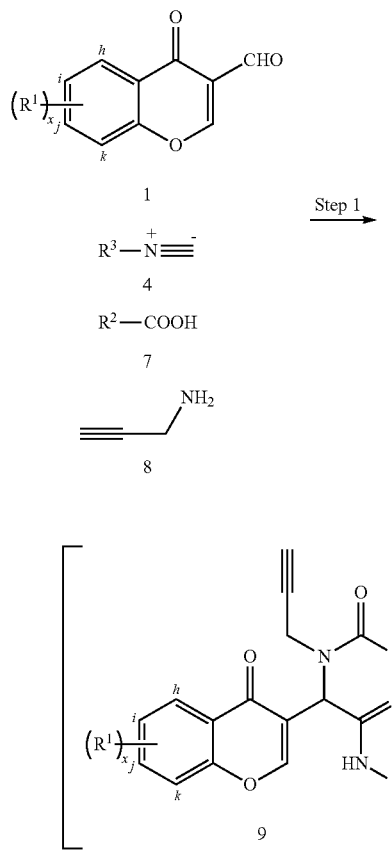

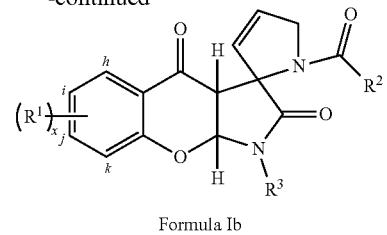

Formula Ib wherein $R^1$, x, $R^2$, and $R^3$ are as defined in claim 9.

17. The method according to claim 16, wherein,

Step 2 is performed in the present of a base and/or a solvent;

optionally, the base in Step 2 is selected from the group consisting of $Cs_2CO_3$, 1,4-diazabicyclo[2.2.2]octane (DABCO), N,N-diisopropylethylamine (DIPEA), diisopropylamine (DIPA), trimethylamine ($Et_3N$) and a combination thereof;

optionally, the base in Step 2 is DIPA;

optionally, the solvent in Step 2 is selected from the group consisting of MeCN, MeOH, EtOH, and a combination thereof;

optionally, the solvent in Step 2 is EtOH;

optionally, the reaction time of Step 2 is 2-10 h, 4-8 h or 6 h;

optionally, the reaction temperature of Step 2 is 80° C.-200° C., 100° C.-150° C., 120° C.-140° C., or 120° C.;

optionally, Step 1 is performed in the present of a solvent;

optionally, the solvent in Step 1 is 2,2,2-trifluoroethanol (TFE);

optionally, Step 1 is performed at room temperature.

18. A method for preparing a compound of Formula Ic or a pharmaceutically acceptable salt thereof according to claim 5, comprising Step 1 and Step 2 below:

Step 1: performing a Ugi four-component reaction of Compounds 1, 4, 7 and 8 to obtain Compound 9;

Step 2: reacting Compound 9 to obtain the compound of Formula Ic;

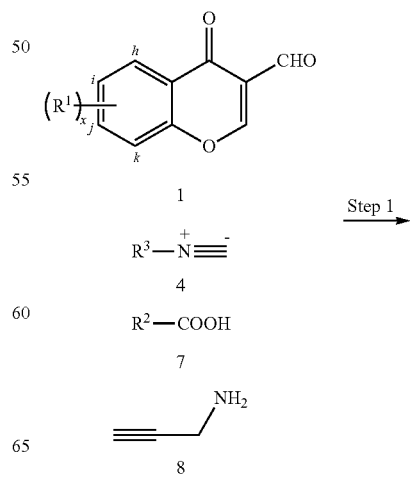

-continued

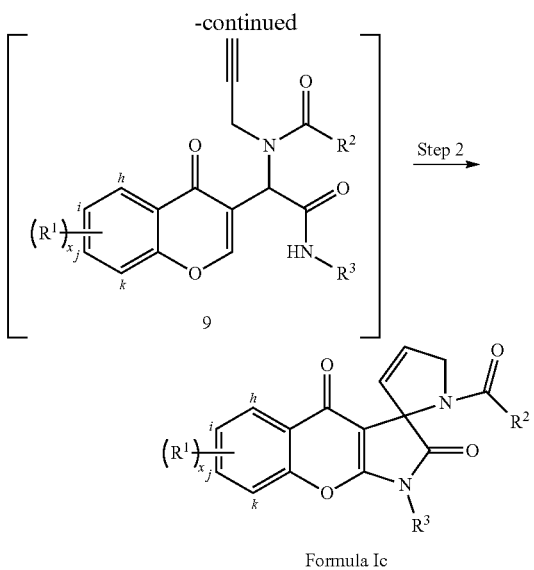

Formula Ic wherein R¹, x, R², and R³ are as defined in claim 5.

19. The method according to claim 18, wherein,

Step 2 is performed in the present of a base and/or a solvent;

optionally, the base in Step 2 is selected from the group consisting of $Cs_2CO_3$, 1,4-diazabicyclo[2.2.2]octane (DABCO), N,N-diisopropylethylamine (DIPEA), diisopropylamine (DIPA), trimethylamine ($Et_3N$) and a combination thereof;

optionally, the base in Step 2 is DIPA;

optionally, the solvent in Step 2 is selected from the group consisting of DMF, EtOH, and a combination thereof;

optionally, the solvent in Step 2 is DMF;

optionally, the reaction time of Step 2 is 2-10 h, 4-8 h or 6 h;

optionally, the reaction temperature of Step 2 is 80° C.-200° C., 100° C.-150° C., 120° C.-140° C., or 120° C.;

optionally, Step 1 is performed in the present of a solvent;

optionally, the solvent in Step 1 is 2,2,2-trifluoroethanol (TFE);

optionally, Step 1 is performed at room temperature.

20. A pharmaceutical composition comprising a compound of Formula I or a pharmaceutically acceptable salt thereof according to claim 1.

21. A method for treating a cancer, comprising administering to a subject in need thereof a therapeutically effective amount of a compound of Formula I or a pharmaceutically acceptable salt thereof according to claim 1;

wherein, the cancer is pancreatic cancer.

* * * * *